(12) United States Patent
Rottlander et al.

(10) Patent No.: US 11,548,849 B2
(45) Date of Patent: Jan. 10, 2023

(54) ALCOHOL DERIVATIVES AS KV7 POTASSIUM CHANNEL OPENERS

(71) Applicant: H. Lundbeck A/S, Valby (DK)

(72) Inventors: Mario Rottlander, Greve (DK); Xiaofang Wang, Shanghai (CN); Debasis Das, Shanghai (CN); Jian Hong, Shanghai (CN); Shu Hui Chen, Calabasas, CA (US); Anette Graven Sams, Vaerlose (DK); Krestian Larsen, Ringsted (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/943,872

(22) Filed: Jul. 30, 2020

(65) Prior Publication Data
US 2021/0032196 A1  Feb. 4, 2021

(30) Foreign Application Priority Data

Aug. 2, 2019 (EP) .................................... 19189750

(51) Int. Cl.
*C07C 235/08* (2006.01)
*C07C 255/44* (2006.01)

(52) U.S. Cl.
CPC .......... *C07C 235/08* (2013.01); *C07C 255/44* (2013.01); *C07C 2601/02* (2017.05); *C07C 2601/04* (2017.05); *C07C 2601/08* (2017.05); *C07C 2601/16* (2017.05)

(58) Field of Classification Search
CPC . C07C 235/08; C07C 255/44; C07C 2601/02; C07C 2601/04; C07C 2601/08; C07C 2601/16; C07C 235/26; C07C 2601/14; H02M 1/0009; H02M 1/44; H05B 6/04
See application file for complete search history.

(56) References Cited

U.S. PATENT DOCUMENTS

| | | | |
|---|---|---|---|
| 10,590,067 | B2 | 3/2020 | Rottlander et al. |
| 2016/0075663 | A1 | 3/2016 | Resnick et al. |
| 2019/0256456 | A1 | 8/2019 | Rottlander et al. |
| 2020/0172474 | A1 | 6/2020 | Rottlander et al. |

FOREIGN PATENT DOCUMENTS

| | | | |
|---|---|---|---|
| CN | 105663136 A | | 6/2016 |
| JP | 2017/95366 A | | 6/2017 |
| TW | 200920350 A | | 5/2009 |
| WO | WO 01/092526 A1 | | 12/2001 |
| WO | WO 01/096540 A2 | | 12/2001 |
| WO | WO 2006/033844 A2 | | 3/2006 |
| WO | WO 2007/090409 A1 | | 8/2007 |
| WO | WO 2007/104717 A1 | | 9/2007 |
| WO | WO 2009/015667 A1 | | 2/2009 |
| WO | WO 2010/060955 A1 | | 6/2010 |
| WO | WO 2014/145852 A2 | | 9/2014 |
| WO | WO 2019/161877 A1 | | 8/2019 |

OTHER PUBLICATIONS

Meanwell (Fluorine and Fluorinated Motifs in the Design and Application of Bioisosteres for Drug Design, J. Med. Chem., 61, pp. 5822-5880, Published Feb. 2018) (Year: 2018).*
Chemical Catalog. (Chemcats: Aurora Fine Chemicals. N-1-(3-difluoromethoxyphenyl) ethyl-1-cyclohexane acetamide. Feb. 13, 2017. Abstract. 1 page, as cited in the IDS filed Apr. 8, 2022) (Year: 2017).*
International Search Report and Written Opinion for International Application No. PCT/EP2020/071520 dated Sep. 14, 2020.
Bialer et al., Progress report on new antiepileptic drugs: a summary of the Sixth Eilat Conference (EILAT VI). Epilepsy Res. Sep. 2002;51(1-2):31-71. doi: 10.1016/s0920-1211(02)00106-7.
Blom et al., From pan-reactive KV7 channel opener to subtype selective opener/inhibitor by addition of a methyl group. PLoS One. Jun. 23, 2014;9(6):e100209. doi: 10.1371/journal.pone.0100209.
Christie M., Molecular and functional diversity of K+ channels. Clin Exp Pharmacol Physiol. Dec. 1995;22(12):944-51. doi: 10.1111/j.1440-1681.1995.tb02331.x.
Cooper et al., Colocalization and coassembly of two human brain M-type potassium channel subunits that are mutated in epilepsy. Proc Natl Acad Sci U S A. Apr. 25, 2000;97(9):4914-9. doi: 10.1073/pnas.090092797.
Dalby-Brown et al., K(v)7 channels: function, pharmacology and channel modulators. Curr Top Med Chem. 2006;6(10):999-1023. doi: 10.2174/156802606777323728.
Delmas et al., Pathways modulating neural KCNQ/M (Kv7) potassium channels. Nat Rev Neurosci. Nov. 2005;6(11):850-62. doi: 10.1038/nrn1785.
Durley et al., Chiral N,N-disubstituted trifluoro-3-amino-2-propanols are potent inhibitors of cholesteryl ester transfer protein. J Med Chem. Aug. 29, 2002;45(18):3891-904. doi: 10.1021/jm020038h.
Friedman et al., KCNQ channel openers reverse depressive symptoms via an active resilience mechanism. Nat Commun. May 24, 2016;7:11671. doi: 10.1038/ncomms11671.

(Continued)

*Primary Examiner* — Yevgeny Valenrod
*Assistant Examiner* — Blaine G Doletski
(74) *Attorney, Agent, or Firm* — Wolf, Greenfield & Sacks, P.C.

(57) ABSTRACT

The present invention provides novel compounds (e.g., compounds of Formula I) which activate the Kv7 potassium channels. Separate aspects of the invention are directed to pharmaceutical compositions comprising said compounds and uses of the compounds to treat disorders responsive to the activation of Kv7 potassium channels.

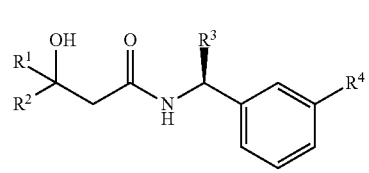

Formula I

9 Claims, No Drawings

(56) References Cited

OTHER PUBLICATIONS

Goldstein et al., Localization of KCNQ and KCNE channel subunits in the central and peripheral nervous system of the rat. Society for Neuroscience. 2003; Abstract.
Greene et al., Modulation of Kv7 channels and excitability in the brain. Cell Mol Life Sci. Feb. 2017;74(3):495-508. doi: 10.1007/s00018-016-2359-y. Epub Sep. 19, 2016.
Hansen et al., The KCNQ channel opener retigabine inhibits the activity of mesencephalic dopaminergic systems of the rat. J Pharmacol Exp Ther. Sep. 2006;318(3):1006-19. doi: 10.1124/jpet.106.106757. Epub Jun. 14, 2006.
Korsgaard et al., Anxiolytic effects of Maxipost (BMS-204352) and retigabine via activation of neuronal Kv7 channels. J Pharmacol Exp Ther. Jul. 2005;314(1):282-92. doi: 10.1124/jpet.105.083923. Epub Apr. 6, 2005.
Koyama et al., Characterization of M-current in ventral tegmental area dopamine neurons. J Neurophysiol. Aug. 2006;96(2):535-43. doi: 10.1152/jn.00574.2005. Epub Jan. 4, 2006.
Li et al., Selective targeting of M-type potassium Kv 7.4 channels demonstrates their key role in the regulation of dopaminergic neuronal excitability and depression-like behaviour. Br J Pharmacol. Dec. 2017;174(23):4277-4294. doi: 10.1111/bph.14026. Epub Oct. 19, 2017.
Marrion et al.,Control of M-current. Annu Rev Physiol. 1997;59:483-504. doi: 10.1146/annurev.physiol.59.1.483.
Noda et al., KCN channels in glial cells. Society for Neuroscience. 2003; Abstract.
Rogawski, M.A., KCNQ2/KCNQ3 K+ channels and the molecular pathogenesis of epilepsy: implications for therapy. Trends Neurosci. Sep. 2000;23(9):393-8. doi: 10.1016/s0166-2236(00)01629-5.
Rostock et al., D-23129: a new anticonvulsant with a broad spectrum activity in animal models of epileptic seizures. Epilepsy Res. Apr. 1996;23(3):211-23. doi: 10.1016/0920-1211(95)00101-8.
Saganich et al., Differential expression of genes encoding subthreshold-operating voltage-gated K+ channels in brain. J Neurosci. Jul. 1, 2001;21(13):4609-24. doi: 10.1523/JNEUROSCI.21-13-04609.2001.
Schroder et al., KCNQ4 channel activation by BMS-204352 and retigabine. Neuropharmacology. Jun. 2001;40(7):888-98. doi: 10.1016/s0028-3908(01)00029-6. Erratum in: Neuropharmacology. Mar. 2003;44(4):553.
Sotty et al., Antipsychotic-like effect of retigabine [N-(2-Amino-4-(fluorobenzylamino)-phenyl)carbamic acid ester], a KCNQ potassium channel opener, via modulation of mesolimbic dopaminergic neurotransmission. J Pharmacol Exp Ther. Mar. 2009;328(3):951-62. doi: 10.1124/jpet.108.146944. Epub Dec. 19, 2008.
Wickenden et al., KCNQ channel expression in rat DRG following nerve ligation. Society for Neuroscience. 2002; Abstract.
Wickenden et al., Retigabine, a novel anti-convulsant, enhances activation of KCNQ2/Q3 potassium channels. Mol Pharmacol. Sep. 2000;58(3):591-600. doi: 10.1124/mol.58.3.591.
Wuttke et al.,. The new anticonvulsant retigabine favors voltage-dependent opening of the Kv7.2 (KCNQ2) channel by binding to its activation gate. Mol Pharmacol. Apr. 2005;67(4):1009-17. doi: 10.1124/mol. 104.010793. Epub Jan. 20, 2005.
PCT/EP2020/071520, dated Sep. 14, 2020, International Search Report and Written Opinion.
International Search Report and Written Opinion for Application No. PCT/EP2018/054057 dated Sep. 12, 2018.
CAS Registry File RN 2061854-53-1, STN Entry Date: Jan. 30, 2017.
CAS Registry File RN 2071323-29-8, STN Entry Date: Feb. 16, 2017.
[No Author Listed] Medication treatment for autism. NICHD Eunice Kennedy Shriver National Institute of Child Health and Human Development. Apr. 19, 2021. http://www.nichd.nih.gov/health/topics/autism/conditioninfo/treatments/medication-treatment. Last accessed Sep. 2, 2021.
[No Author Listed] What causes autism? NICHD Eunice Kennedy Shriver National Institute of Child Health and Human Development. Jan. 31, 2017. http://www.nichd.nih.gov/health/topics/autism/conditioninfo/causes. Last accessed Sep. 2, 2021.
Gati et al., Towards therapeutic applications of arthropod venom k(+)-channel blockers in CNS neurologic diseases involving memory acquisition and storage. J Toxicol. 2012;2012:756358. Epub Jun. 4, 2012.
Humphries et al., Neuronal and cardiovascular potassium channels as therapeutic drug targets: promise and pitfalls. J Biomol Screen. 2015 Oct;20(9):1055-73. Epub Aug. 24, 2015.
Weaver et al., A thallium-sensitive, fluorescence-based assay for detecting and characterizing potassium channel modulators in mammalian cells. J Biomol Screen. Dec. 2004;9(8):671-7.
Wulff et al., Voltage-gated potassium channels as therapeutic targets. Nat Rev Drug Discov. Dec. 2009;8(12):982-1001.
Gunthorpe et al., The mechanism of action of retigabine (ezogabine), a first-in-class K+ channel opener for the treatment of epilepsy. Epilepsia. Mar. 2012;53(3):412-24. Epub Jan. 5, 2012.
International Preliminary Report on Patentability for Application No. PCT/EP2018/054057 dated Aug. 7, 2020.
[No Author Listed], Chemical Catalog. Chemcats: Aurora Fine Chemicals. Butanamide, 3-hydroxy-3-methyl-N- (1(S)-1-(3-trifluoromethoxyphenyl] ethyl], Apr. 2, 2018. Abstract. 1 page.
[No Author Listed], Chemical Catalog. Chemcats: Aurora Fine Chemicals. N-1-(3-difluoromethoxyphenyl) ethyl-1-cyclohexane acetamide. Feb. 13, 2017. Abstract. 1 page.
[No Author], CAS Registry File RN 2071998-86-0, STN Entry Date: Feb. 17, 2017.
Allen et al., Genetic potassium channel-associated epilepsies: Clinical review of the Kv family. Eur J Paediatr Neurol. Jan. 2020;24:105-116. Epub Dec. 14, 2019.
Dencker et al., Antimanic efficacy of retigabine in a proposed mouse model of bipolar disorder. Behav Brain Res. Feb. 11, 2010;207(1):78-83. doi: 10.1016/j.bbr.2009.09.040. Epub Oct. 6, 2009.
Wang et al., KCNQ2 and KCNQ3 Potassium Channel Subunits: Molecular Correlates of the M-Channel. Science. Dec. 4, 1998;282(5395):1890-3.
U.S. Appl. No. 17/631,762, filed Jan. 31, 2022, Pending.
International Search Report and Written Opinion for International Application No. PCT/EP2020/071514 dated Oct. 12, 2020.
International Preliminary Report on Patentability for Application No. PCT/EP2020/071514, dated Feb. 17, 2022.
International Preliminary Report on Patentability for Application No. PCT/EP2020/071520, dated Feb. 17, 2022.

* cited by examiner

ALCOHOL DERIVATIVES AS KV7 POTASSIUM CHANNEL OPENERS

CROSS-REFERENCE TO RELATED APPLICATION

This application claims priority to European Application No. 19189750.3, filed Aug. 2, 2019, the entire contents of the aforementioned application is hereby incorporated herein by reference.

FIELD OF THE INVENTION

The present invention relates to novel compounds which activate the Kv7 potassium channels. Separate aspects of the invention are directed to pharmaceutical compositions comprising said compounds and uses of the compounds to treat disorders responsive to the activation of Kv7 potassium channels.

BACKGROUND OF THE INVENTION

Voltage-dependent potassium (Kv) channels conduct potassium ions ($K^+$) across cell membranes in response to changes in the membrane potential and can thereby regulate cellular excitability by modulating (increasing or decreasing) the electrical activity of the cell. Functional Kv channels exist as multimeric structures formed by the association of four alpha and four beta subunits. The alpha subunits comprise six transmembrane domains, a pore-forming loop and a voltage-sensor and are arranged symmetrically around a central pore. The beta or auxiliary subunits interact with the alpha subunits and can modify the properties of the channel complex to include, but not be limited to, alterations in the channel's electrophysiological or biophysical properties, expression levels or expression patterns.

Nine Kv channel alpha subunit families have been identified and are termed Kv1-Kv9. As such, there is an enormous diversity in Kv channel function that arises as a consequence of the multiplicity of sub-families, the formation of both homomeric and heteromeric subunits within sub-families and the additional effects of association with beta subunits (Christie, 25 Clinical and Experimental Pharmacology and Physiology, 1995, 22, 944-951).

The Kv7 channel family consists of at least five members which include one or more of the following mammalian channels: Kv7.1, Kv7.2, Kv7.3, Kv7.4, Kv7.5 and any mammalian or non-mammalian equivalent or variant (including splice variants) thereof. Alternatively, the members of this family are termed by the gene name KCNQ1, KCNQ2, KCNQ3, KCNQ4 and KCNQ5 respectively (Dalby-Brown, et al., Current Topics in Medicinal Chemistry, 2006, 6, 9991023).

As mentioned above, the neuronal Kv7 potassium channels play roles in controlling neuronal excitation. Kv7 channels, in particular Kv7.2/Kv7.3 heterodimers, underlie the M-current (Wang et al Science. 1998 Dec. 4; 282(5395): 1890-3). The M-current has a characteristic time- and voltage-dependence that results in stabilisation of the membrane potential in response to multiple excitatory stimuli.

In this way, the M-current is involved in controlling neuronal excitability (Delmas & Brown, Nature, 2005, 6, 850-862). The M-current is a non-inactivating potassium current found in many neuronal cell types. In each cell type, it is dominant in controlling membrane excitability by being the only sustained current in the range of action potential initiation (Marrion, Annual Review Physiology 1997, 59, 483-504).

Retigabine (N-(2-amino-4-(4-fluorobenzylamino)-phenyl) carbamic acid ethyl ester) is a compound which binds to the Kv7 potassium channels (Wuttke, et al., Molecular Pharmacology, 2005, 67, 1009-1017). Retigabine activates $K^+$ current in neuronal cells and the pharmacology of this induced current displays concordance with the published pharmacology of the M-channel that has been correlated to the Kv7.2/3 $K^+$ channel heteromultimer which suggests that activation of Kv7.2/3 channels is responsible for at least some of the anticonvulsant activity of this agent (Wickenden, et al., Molecular Pharmacology 2000, 58, 591-600). Retigabine is effective in reducing the incidence of seizures in epileptic patients (Bialer, et al., Epilepsy Research 2002, 51, 31-71). Retigabine has a broad spectrum and potent anticonvulsant properties. It is active after oral and intraperitoneal administration in rats and mice in a range of anticonvulsant tests (Rostock, et al., Epilepsy Research 1996, 23, 211-223).

The five members of this family of ion channels differ in their expression patterns. The expression of Kv7.1 is restricted to the heart, peripheral epithelial and smooth muscle, whereas the expression of Kv7.2, Kv7.3, Kv7.4 and Kv7.5 appear to be dominant in the nervous system which includes the hippocampus, cortex, ventral tegmental area, and dorsal root ganglion neurons (for a review see Greene & Hoshi, Cellular and Molecular Life Sciences, 2017, 74(3), 495-508).

The KCNQ2 and KCNQ3 genes appear to be mutated in an inherited form of epilepsy known as benign familial neonatal convulsions (Rogawski, Trends in Neurosciences 2000, 23, 393-398). The proteins encoded by the KCNQ2 and KCNQ3 genes are localised in the pyramidal neurons of the human cortex and hippocampus, regions of the brain associated with seizure generation and propagation (Cooper et al., Proceedings National Academy of Science USA 2000, 97, 4914-4919).

Furthermore, mRNA for Kv7.3 and 5, in addition to that for Kv7.2, are expressed in astrocytes and glial cells. Thus Kv7.2, Kv7.3 and Kv7.5 channels may help modulate synaptic activity in the CNS and contribute to the neuroprotective effects of KCNQ channel openers (Noda, et al., Society for Neuroscience Abstracts 2003, 53.9), which would be relevant for the treatment of neurodegenerative disorders such as but not limited to Alzheimer's disease, Parkinson's disease and Huntington's chorea.

mRNA for Kv7.2 and Kv7.3 subunits are found in brain regions associated with anxiety and emotional behaviours such as depression and bipolar disorder e.g. hippocampus, ventral tegmental area and amygdala (Saganich, et al. Journal of Neuroscience 2001, 21, 4609-4624; Friedman et al., Nat Commun. 2016; 7: 11671), and retigabine is reportedly active in animal models of anxiety-like behaviour (Korsgaard et al J Pharmacol Exp Ther. 2005 July; 314(1): 282-92. Epub 2005 Apr. 6). As such Kv7 channels are relevant for the treatment of emotional related disorders such as but not limited to bipolar depression, major depressive disorder, anxiety, suicide, panic attacks, social phobia.

Kv7.2/3 channels have also been reported to be upregulated in models of neuropathic pain (Wickenden, et al., Society for Neuroscience Abstracts 2002, 454.7), and potassium channel modulators have been hypothesised to be active in both neuropathic pain and epilepsy (Schroder, et al., Neuropharmacology 2001, 40, 888-898). In addition to a role in neuropathic pain, the expression of mRNA for Kv7.2-5 in the trigeminal and dorsal root ganglia and in the trigeminal nucleus caudalis implies that openers of these channels may also affect the sensory processing of migraine pain (Goldstein, et al. Society for Neuroscience Abstracts 2003, 53.8). Taken together, this evidence points to the relevance of KCNQ channel openers for the treatment of chronic pain and neuropathy related disorders.

WO 07/90409 relates to the use of Kv7 channel openers for the treatment of schizophrenia. Kv7 channel openers modulate the function of the dopaminergic system (Friedman et al., Nat Commun. 2016; Scotty et al J Pharmacol Exp Ther. 2009 March; 328(3):951-62. doi: 10.1124/jpet.108.146944. Epub 2008 Dec. 19; Koyama et al., J Neurophysiol. 2006 August; 96(2):535-43. Epub 2006 Jan. 4; Li et al Br J Pharmacol. 2017 December; 174(23):4277-4294. doi: 10.1111/bph.14026. Epub 2017 Oct. 19; Hansen et al J Pharmacol Exp Ther. 2006 September; 318(3):1006-19. Epub 2006 Jun. 14) which would be relevant for the treatment of psychiatric disorders such as but not limited to psychosis, mania, stress-related disorders, acute stress reactions, attention deficit/hyperactivity disorder, posttraumatic stress disorder, obsessive compulsive disorder, impulsivity disorders, personality disorders, schizotypical disorder, aggression, autism spectrum disorders. WO 01/96540 discloses the use of modulators of the M-current formed by expression of KCNQ2 and KCNQ3 genes for insomnia, while WO 01/092526 discloses that modulators of Kv7.5 can be utilized for the treatment of sleep disorders. WO 09/015667 discloses the use of Kv7 openers in the treatment of sexual dysfunction.

Although patients suffering from the above-mentioned disorders may have available treatment options, many of these options lack the desired efficacy and are accompanied by undesired side effects. Therefore, an unmet need exists for novel therapies for the treatment of said disorders.

In an attempt to identify new therapies, the inventors have identified a series of novel compounds as represented by Formula I. Accordingly, the present invention provides novel compounds as medicaments for the treatment of disorders which are modulated by the KCNQ potassium channels.

SUMMARY OF THE INVENTION

The present invention relates to a compound of Formula I

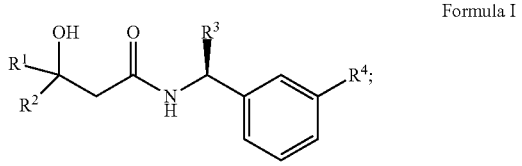

Formula I wherein
R1 is selected from the group consisting of $C_1$-$C_6$ alkyl, $CF_3$, $CH_2CF_3$, $CF_2CHF_2$, $C_3$-$C_8$ cycloalkyl, wherein said $C_3$-$C_8$ cycloalkyl may be substituted with 1 or 2 $C_1$-$C_3$ alkyl, F, $CHF_2$ or $CF_3$, and
R2 is H, $C_1$-$C_6$ alkyl or $CF_3$; or
R1 and R2 combine (together with the carbon atoms they are attached) to form $C_3$-$C_5$ cycloalkyl optionally substituted with 1 or 2 F, $CHF_2$ or $CF_3$; and R3 is $C_1$-$C_3$ alkyl or $CH_2O$—$C_{1-3}$ alkyl, said $C_1$-$C_3$ alkyl or $CH_2O$—$C_{1-3}$ alkyl substituted with C≡N, 3 F or $C_3$-$C_5$ cycloalkyl;
R4 is selected from the group consisting of $OCF_3$, or $OCHF_2$.

According to another aspect of the invention, the invention relates to novel compounds as of present invention.

The invention also concerns a pharmaceutical composition comprising a compound according to the invention and a pharmaceutically acceptable carrier or excipient.

Furthermore, the invention concerns a method of treating a patient as described in the claims and embodiments and includes treatments of patients suffering from epilepsy, a bipolar disorder, migraine and schizophrenia comprising administering to the subject a therapeutically effective amount of the compound according to the invention.

DETAILED DESCRIPTION OF THE INVENTION

According to an embodiment, the compound of Formula I may have an R4 group which is $OCF_3$ or $OCHF_2$.

According to another embodiment the compound according to Formula I may have an R3 group is selected from the group comprising CH2-O—$CF_3$, CH2-O-cyclopropyl, CH2-C≡N.

According to a further embodiment, the compound according to Formula I may have an R1 group which is $C_3$-$C_4$ cycloalkyl, optionally substituted with 1 or 2 $C_1$-$C_3$ alkyl, F, $CHF_2$ or $CF_3$.

In yet another embodiment the compound according to any Formula I may have an R1 group and an R2 group, which combine to form cyclobutyl optionally substituted with 1 or 2 F, and R4 is $OCF_3$ or $OCHF_2$.

According to a specific embodiment of the invention the compound according to the invention is selected from the group consisting of:
(S)—N—((R)-2-cyclopropoxy-1-(3-(difluoromethoxy) phenyl)ethyl)-3-hydroxy-4,4-dimethylpentanamide;
(S)—N—((R)-1-(3-(difluoromethoxy)phenyl)-2-(trifluoromethoxy)ethyl)-3-hydroxy-4,4-dimethylpentanamide;
(S)—N—((R)-1-(3-(trifluoromethoxy)phenyl)-2-(trifluoromethoxy)ethyl)-3-hydroxy-4,4-dimethylpentanamide;
(S)—N—((S)-2-cyano-1-(3-(trifluoromethoxy)phenyl) ethyl)-3-hydroxy-4,4-dimethylpentanamide;
(S)—N—((S)-3-cyano-1-(3-(trifluoromethoxy)phenyl) propyl)-3-hydroxy-4,4-dimethylpentanamide;
(R)—N-(2-cyclopropoxy-1-(3-(trifluoromethoxy) phenyl) ethyl)-2-(3,3-difluoro-1-hydroxycyclobutyl)acetamide;
(R)—N-(2-cyclopropoxy-1-(3-(difluoromethoxy) phenyl) ethyl)-2-(3,3-difluoro-1-hydroxycyclobutyl)acetamide;
(R)-2-(3,3-difluoro-1-hydroxycyclobutyl)-N-(1-(3-(difluoromethoxy)phenyl)-2-(trifluoromethoxy)ethyl)acetamide; or
(S)—N-(2-cyano-1-(3-(trifluoromethoxy) phenyl)ethyl)-2-(3,3-difluoro-1-hydroxycyclobutyl)acetamide or a pharmaceutically acceptable salt of any of these compounds.

Another aspect of the invention relates to a compound selected from the group consisting of:
(R)—N—((R)-2-(difluoromethoxy)-1-(3-(difluoromethoxy) phenyl)ethyl)-3-hydroxy-4,4-dimethylpentanamide;
(S)—N—((R)-2-(difluoromethoxy)-1-(3-(difluoromethoxy) phenyl)ethyl)-3-hydroxy-4,4-dimethylpentanamide;
(S)-3-hydroxy-4,4-dimethyl-N—((S)-1-(3-(2,2,2-trifluoroethoxy)phenyl)ethyl) pentanamide;
R)-3-hydroxy-4,4-dimethyl-N—((S)-1-(3-(2,2,2-trifluoroethoxy) phenyl)ethyl)pentanamide;

(R)—N—((R)-2-(difluoromethoxy)-1-(3-(difluoromethoxy)phenyl)ethyl)-3-hydroxy-3-(1-(trifluoro-methyl)cyclopropyl)propanamide;

(S)—N—((R)-2-(difluoromethoxy)-1-(3-(difluoromethoxy)phenyl)ethyl)-3-hydroxy-3-(1-(trifluoro-methyl)cyclopropyl)propanamide;

(R)—N—((R)-2-(difluoromethoxy)-1-(3-(trifluoromethoxy)phenyl)ethyl)-3-hydroxy-3-(1-(trifluoromethyl)cyclopropyl)propanamide;

(S)—N—((R)-2-(difluoromethoxy)-1-(3-(trifluoromethoxy)phenyl) ethyl)-3-hydroxy-3-(1-(trifluoromethyl)cyclopropyl) propanamide;

(R)-3-(3,3-difluorocyclobutyl)-N—((R)-2-(difluoromethoxy)-1-(3-(difluoromethoxy)phenyl)ethyl)-3-hydroxypropanamide;

(S)-3-(3,3-difluorocyclobutyl)-N—((R)-2-(difluoromethoxy)-1-(3-(difluoromethoxy)phenyl)ethyl)-3-hydroxypropanamide (R)-3-(3,3-difluorocyclobutyl)-N—((R)-2-(difluoromethoxy)-1-(3-(trifluoromethoxy)phenyl) ethyl)-3-hydroxypropanamide;

(S)-3-(3,3-difluorocyclobutyl)-N—((R)-2-(difluoromethoxy)-1-(3-(trifluoromethoxy)phenyl)ethyl)-3-hydroxypropanamide;

(S)-3-(3,3-difluorocyclobutyl)-N—((S)-1-(3-(difluoromethoxy)phenyl)butyl)-3-hydroxypropanamide;

(R)-3-(3,3-difluorocyclobutyl)-N—((S)-1-(3-(difluoromethoxy) phenyl)butyl)-3-hydroxypropanamide;

(S)—N—((R)-2-(difluoromethoxy)-1-(3-(difluoromethoxy)phenyl)ethyl)-3-(1-ethylcyclopropyl)-3-hydroxypropanamide;

(R)—N—((R)-2-(difluoromethoxy)-1-(3-(difluoromethoxy)phenyl) ethyl)-3-(1-ethylcyclopropyl)-3-hydroxypropanamide;

(S)—N—((S)-1-(3-(difluoromethoxy)phenyl)butyl)-3-hydroxy-4,4-dimethylpentanamide;

(S)—N—((S)-1-(3-(difluoromethoxy)phenyl)-4,4-difluorobutyl)-3-hydroxy-4,4-dimethylpentanamide;

(S)—N—((S)-1-(3-(difluoromethoxy)phenyl)-3,3-difluoropropyl)-3-hydroxy-4,4-dimethylpentanamide;

(S)—N—((S)-1-(3-(difluoromethoxy) phenyl)ethyl)-3-hydroxy-4,4-dimethylpentanamide;

(R)-2-(3,3-difluoro-1-hydroxycyclobutyl)-N-(2-(difluoromethoxy)-1-(3-(difluoromethoxy)phenyl) ethyl)acetamide;

(R)-2-(3,3-difluoro-1-hydroxycyclobutyl)-N-(2-(difluoromethoxy)-1-(3-(trifluoromethoxy)phenyl)ethyl)acetamide;

(S)-2-(3,3-difluoro-1-hydroxycyclobutyl)-N-(1-(3-(difluoromethoxy)phenyl)butyl)acetamide;

(S)-2-(3,3-difluoro-1-hydroxycyclobutyl)-N-(1-(3-(difluoromethoxy)phenyl)-4,4-difluorobutyl)acetamide;

(S)-2-(3,3-difluoro-1-hydroxycyclobutyl)-N-(1-(3-(trifluoromethoxy) phenyl)propyl)acetamide;

(S)—N-(3,3-difluoro-1-(3-(trifluoromethoxy)phenyl)propyl)-2-(3,3-difluoro-1-hydroxycyclobutyl)acetamide;

(S)—N—((R)-2-(difluoromethoxy)-1-(3-(difluoromethoxy)phenyl)ethyl)-3-hydroxy-4,4-dimethylpentanamide;

(R)—N—((R)-2-(difluoromethoxy)-1-(3-(difluoromethoxy)phenyl)ethyl)-3-(1-fluorocyclopropyl)-3-hydroxybutanamide;

(S)—N—((R)-2-(difluoromethoxy)-1-(3-(difluoromethoxy)phenyl) ethyl)-3-(1-fluorocyclopropyl)-3-hydroxybutanamide;

(S)—N—((R)-2-(difluoromethoxy)-1-(3-(trifluoromethoxy)phenyl)ethyl)-3-(1-fluorocyclopropyl)-3-hydroxybutanamide;

(R)—N—((R)-2-(difluoromethoxy)-1-(3-(trifluoromethoxy)phenyl) ethyl)-3-(1-fluorocyclopropyl)-3-hydroxybutanamide;

(R)-3-cyclopropyl-N—((R)-2-(difluoromethoxy)-1-(3-(trifluoromethoxy)phenyl) ethyl)-3-hydroxybutanamide;

(S)-3-cyclopropyl-N—((R)-2-(difluoromethoxy)-1-(3-(trifluoromethoxy) phenyl)ethyl)-3-hydroxybutanamide;

(R)—N—((R)-2-(difluoromethoxy)-1-(3-(difluoromethoxy)phenyl)ethyl)-5,5,5-trifluoro-3-hydroxy-3-methylpentanamide;

(S)—N—((R)-2-(difluoromethoxy)-1-(3-(difluoromethoxy)phenyl)ethyl)-5,5,5-trifluoro-3-hydroxy-3-methylpentanamide;

(R)—N—((R)-2-(difluoromethoxy)-1-(3-(difluoromethoxy)phenyl)ethyl)-3-hydroxy-3,5-dimethylhexanamide;

(S)—N—((R)-2-(difluoromethoxy)-1-(3-(difluoromethoxy)phenyl)ethyl)-3-hydroxy-3,5-dimethylhexanamide;

(S)—N—((R)-2-(difluoromethoxy)-1-(3-(difluoromethoxy)phenyl)ethyl)-3-hydroxy-3,4-dimethylpentanamide;

(R)—N—((R)-2-(difluoromethoxy)-1-(3-(difluoromethoxy)phenyl)ethyl)-3-hydroxy-3,4-dimethylpentanamide;

(S)—N—((R)-2-(difluoromethoxy)-1-(3-(difluoromethoxy)phenyl)ethyl)-3-(3,3-dimethylcyclobutyl)-3-hydroxypropanamide;

(R)—N—((R)-2-(difluoromethoxy)-1-(3-(difluoromethoxy)phenyl)ethyl)-3-(3,3-dimethylcyclobutyl)-3-hydroxypropanamide;

(S)-3-cyclopentyl-N—((R)-2-(difluoromethoxy)-1-(3-(difluoromethoxy)phenyl)ethyl)-3-hydroxypropanamide;

(R)-3-cyclopentyl-N—((R)-2-(difluoromethoxy)-1-(3-(difluoromethoxy)phenyl)ethyl)-3-hydroxypropanamide;

(R)-3-(1-fluorocyclopropyl)-3-hydroxy-N—((R)-2-methoxy-1-(3-(trifluoromethoxy)phenyl)ethyl)butanamide;

and (S)-3-(1-fluorocyclopropyl)-3-hydroxy-N—((R)-2-methoxy-1-(3-(trifluoromethoxy)phenyl)ethyl)butanamide or a pharmaceutically acceptable salt of any of these compounds.

Reference to compounds encompassed by the present invention includes racemic mixtures as well as optically pure isomers of the compounds for which this is relevant, as well as tautomeric forms the compounds for which this is relevant. Furthermore, the compounds of the present invention may potentially exist in polymorphic and amorphic forms, or as unsolvated as well as solvated forms with pharmaceutically acceptable solvents such as water, ethanol and the like.

The present invention also includes isotopelabeled forms of the compounds of the invention, such as Deuterium. The compound may also incorporate positron-emitting isotopes for medical imaging and positron-emitting tomography (PET) studies for determining the distribution of receptors. Suitable positron-emitting isotopes that can be incorporated in compounds of the invention are 11C, 13N, 15O, and 18F. Isotopically-labeled compounds of the invention can generally be prepared by conventional techniques known to those skilled in the art or by processes analogous to those described in the accompanying Examples using appropriate isotopically-labeled reagent in place of non-isotopically-labeled reagent.

The compound according to the invention may be in a pharmaceutical composition comprising the compound and a pharmaceutically acceptable excipient or carrier.

In one embodiment, the invention relates to a compound according to the invention for use in therapy.

In another embodiment the invention relates to a method of treating a patient in the need thereof suffering from epilepsy, bipolar disorder, migraine or schizophrenia comprising administering to the subject a therapeutically effective amount of a compound according to the invention In yet another embodiment the invention relates to a method of treating a patient in the need thereof suffering from psychosis, mania, stress-related disorders, acute stress reactions, bipolar depression, major depressive disorder, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntington's chorea, sclerosis, multiple sclerosis, Alzheimer's disease comprising administering to the subject a therapeutically effective amount of a compound according to the invention According to an embodiment the compound of the invention is used in therapy.

The use of a compound according to the invention is for the treatment of epilepsy, bipolar disorder, migraine or schizophrenia or in another embodiment for the treatment of psychosis, mania, stress-related disorders, acute stress reactions, bipolar depression, major depressive disorder, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntington's chorea, sclerosis, multiple sclerosis, Alzheimer's disease.

In another embodiment, the compound of the invention is for the manufacture of a medicament for treating epilepsy, Fragile X syndrome, Angelman syndrome, bipolar disorder, migraine or schizophrenia or in another embodiment for the manufacture of a medicament for treating psychosis, mania, stress-related disorders, acute stress reactions, bipolar depression, major depressive disorder, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntington's chorea, sclerosis, multiple sclerosis, Alzheimer's disease.

In the present context, "optionally substituted" means that the indicated moiety may or may not be substituted, and when substituted is mono- or di-substituted. It is understood that where no substituents are indicated for an "optionally substituted" moiety, then the position is held by a hydrogen atom.

A given range may interchangeably be indicated with "-" (dash) or "to", e.g. the term "$C_{1-3}$ alkyl" is equivalent to "$C_1$ to $C_3$ alkyl".

The terms "$C_1$-$C_3$ alkyl" and "$C_1$-$C_6$ alkyl" refer to an unbranched or branched saturated hydrocarbon having from one up to six carbon atoms, inclusive. Examples of such groups include, but are not limited to, methyl, ethyl, 1-propyl, 2-propyl, 1-butyl, 2-butyl and t-butyl.

The term "$C_1$-$C_3$ alkoxy" refers to a moiety of the formula —OR, wherein R indicates $C_1$-$C_3$ alkyl as defined above.

The terms "$C_3$-$C_4$ cycloalkyl", "$C_3$-$C_5$ cycloalkyl", "$C_3$-$C_8$ cycloalkyl" or "cyclopropyl" refers to a saturated monocyclic ring. Examples of such groups includes cyclopropyl, cyclobutyl, cyclopentyl, cyclohexyl, cycloheptyl and cyclooctyl.

Administration Routes:

Pharmaceutical compositions comprising a compound of the present invention defined above, may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients:

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound according to the invention, such as one of the compounds disclosed in the Experimental Section herein. The present invention also provides a process for making a pharmaceutical composition comprising a compound according to the invention. The pharmaceutical compositions according to the invention may be formulated with pharmaceutically acceptable excipients in accordance with conventional techniques such as those disclosed in Remington, "The Science and Practice of Pharmacy", $22^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is a requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the gender, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

Isomeric and Tautomeric Forms:

When compounds of the present invention contain one or more chiral atoms, reference to the compounds will, unless otherwise specified, cover the enantiomerically or diastereomerically pure compound as well as mixtures of the enantiomers or diastereomers in any ratio.

MDL Enhanced Stereo representation is used to describe unknown stereochemistry of the compounds of the invention. Hence, the label "or1" on a chiral carbon atom is used to indicate that the absolute stereoconformation at this atom is not known; e.g. the stereoconformation at this carbon atom is either (S) or (R).

Furthermore, the chiral bond from a carbon atom labelled "or", using upward wedge or downward wedge, are equal representations; e.g. the two drawings have the same meaning, the meaning being that the absolute stereoconformation at the "or1" labelled carbon atom is not known and can be (S) or (R).

Thus, the use of upward wedge bonds and downward wedge bonds from atoms labelled "or1", are merely intended to provide a visual cue that the drawings represent different stereoisomers, in which the conformation at the "or1" labelled carbon atom is not known.

Furthermore, some of the compounds of the present invention may exist in different tautomeric forms and it is intended that any tautomeric forms that the compounds are able to form are included within the scope of the present invention.

Therapeutically Effective Amount:

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Use in Epilepsy, Epileptic Syndromes, Epileptic Symptoms or Seizures

In another embodiment the invention relates to a method of treating a patient in the need thereof suffering from epilepsy, epileptic syndromes, epileptic symptoms, treatment resistant or refractory epilepsy, or seizures comprising administering to the subject a therapeutically effective amount of a compound according to the invention.

In yet another embodiment the invention relates a method of treating a patient in the need thereof suffering from Focal (partial) epilepsy with simple partial seizures, Focal (partial) epilepsy with complex partial seizures, Generalized idiopathic epilepsy, Grand mal seizures, Status epilepticus, neonatal seizures, KCNQ epileptic encephalopathy (KCNQ2EE) and Benign Familial Neonatal Convulsions and other epileptic syndromes (such as severe myoclonic epilepsy in infancy, epilepsy with continuous spike waves during slow-wave sleep, West syndrome, Lennox-Gastaut syndrome, Dravet syndrome and Early myoclonic encephalopathy Ohtahara syndrome, or seizures related to stress, hormonal changes, drugs (such as such as amphetamines or cocaine), alcohol, infection, or metabolic disturbances (such as hyponatraemia) or for use in the treatment epileptic symptoms as part of neurogenerative disorders, such as Alzheimer's disease, Lewy body disease, Huntington's disease juvenile form, fronto-temporal lobar degeneration comprising administering to the subject a therapeutically effective amount of a compound of the invention.

The use of a compound according to the invention is for the treatment of epilepsy, including the use in the treatment of Focal (partial) epilepsy with simple partial seizures, Focal (partial) epilepsy with complex partial seizures, Generalized idiopathic epilepsy, Grand mal seizures, Status epilepticus, neonatal seizures, KCNQ epileptic encephalopathy (KCNQ2EE) and Benign Familial Neonatal Convulsions and other epileptic syndromes (such as severe myoclonic epilepsy in infancy, epilepsy with continuous spike waves during slow-wave sleep, West syndrome, Lennox-Gastaut syndrome, Dravet syndrome and Early myoclonic encephalopathy Ohtahara syndrome), or seizures related to stress, hormonal changes, drugs, alcohol, infection, traumatic brain injury, stroke, brain cancers, autism spectrum disorders or metabolic disturbances (such as hyponatraemia), or for use in the epileptic symptoms as part of neurogenerative disorders, such as Alzheimer's disease, Lewy body disease, Huntington's disease juvenile form, fronto-temporal lobar degeneration.

In another embodiment, the compound of the invention is for the manufacture of a medicament for treating epilepsy, epileptic syndromes, epileptic symptoms, treatment resistant or refractory epilepsy, or seizures including Focal (partial) epilepsy with simple partial seizures, Focal (partial) epilepsy with complex partial seizures, Generalized idiopathic epilepsy, Grand mal seizures, Status epilepticus, neonatal seizures, KCNQ epileptic encephalopathy (KCNQ2EE) and Benign Familial Neonatal Convulsions and other epileptic syndromes (such as severe myoclonic epilepsy in infancy, epilepsy with continuous spike waves during slow-wave sleep, West syndrome, Lennox-Gastaut syndrome, Dravet syndrome and Early myoclonic encephalopathy Ohtahara syndrome, or seizures related to stress, hormonal changes, drugs, alcohol, infection, traumatic brain injury, stroke, brain cancers, autism spectrum disorders or metabolic disturbances (such as hyponatraemia) or for use in the treatment epileptic symptoms as part of neurogenerative disorders, such as Alzheimer's disease, Lewy body disease, Huntington's disease juvenile form, fronto-temporal lobar degeneration.

The classification of epilepsy can be based on ICD-10 (2016, published by WHO) and is described in section G40 and G41, and is included in the treatment of epilepsy according to the invention
G40.0 Localization-related (focal)(partial) idiopathic epilepsy and epileptic syndromes with seizures of localized onset
G40.1 Localization-related (focal)(partial) symptomatic epilepsy and epileptic syndromes with simple partial seizures
G40.2 Localization-related (focal)(partial) symptomatic epilepsy and epileptic syndromes with complex partial seizures
G40.3 Generalized idiopathic epilepsy and epileptic syndromes
G40.4 Other generalized epilepsy and epileptic syndromes
G40.5 Special epileptic syndromes
G40.6 Grand mal seizures, unspecified (with or without petit mal)
G40.7 Petit mal, unspecified, without grand mal seizures
G40.8 Other epilepsy
G40.9 Epilepsy, unspecified
G41 Status epilepticus
Treatment of Seizures A seizure is a sudden, uncontrolled electrical disturbance in the brain. It can cause changes in behavior, movements or feelings, and in levels of consciousness. If a person has two or more seizures or a tendency to have recurrent seizures this is diagnosed as epilepsy.

There are many types of seizures, which range in severity. Seizure types vary by where and how they arise in the brain. Most seizures last from 30 seconds to two minutes.

Focal Seizures
Focal seizures result from abnormal electrical activity in one area of the brain. Focal seizures can occur with or without loss of consciousness:
  Focal seizures with impaired awareness. These seizures involve a change or loss of consciousness or awareness. The person may stare into space and not respond normally to the environment or perform repetitive movements, such as hand rubbing, chewing, swallowing or walking in circles.
  Focal seizures without loss of consciousness. These seizures may alter emotions or change the way things look, smell, feel, taste or sound, but the person doesn't lose consciousness. These seizures may also result in the involuntary jerking of a body part, such as an arm or leg, and spontaneous sensory symptoms such as tingling, dizziness and flashing lights.
Generalized Seizures
Seizures that appear to involve all areas of the brain are called generalized seizures. Different types of generalized seizures include:
  Absence seizures. Absence seizures, previously known as petit mal seizures, often occur in children and are characterized by staring into space or by subtle body movements, such as eye blinking or lip smacking. These seizures may occur in clusters and cause a brief loss of awareness.
  Tonic seizures. Tonic seizures cause stiffening of your muscles. These seizures usually affect muscles in the back, arms and legs.
  Atonic seizures. Atonic seizures, also known as drop seizures, cause a loss of muscle control, which may cause suddenly collapse or fall down.
  Clonic seizures. Clonic seizures are associated with repeated or rhythmic, jerking muscle movements. These seizures usually affect the neck, face and arms.
  Myoclonic seizures. Myoclonic seizures usually appear as sudden brief jerks or twitches of your arms and legs.
  Tonic-clonic seizures. Tonic-clonic seizures, previously known as grand mal seizures, are the most dramatic type of epileptic seizure and can cause an abrupt loss of consciousness, body stiffening and shaking, and sometimes loss of bladder control or biting the tongue.
Many times, seizures may be associated or caused by:
High fever, which can be associated with an infection such as meningitis
Lack of sleep
Low blood sodium (hyponatremia), which can happen with diuretic therapy
Medications, such as certain pain relievers, antidepressants or smoking cessation therapies, that lower the seizure threshold
Head trauma that causes an area of bleeding in the brain
Stroke
Brain tumor
Drugs, such as amphetamines or cocaine
Alcohol Headings and sub-headings are used herein for convenience only and should not be construed as limiting the invention in any way.

The use of any and all examples, or exemplary language (including "for instance", "for example", "e.g.", and "as such") in the present specification is intended merely to better illustrate the invention and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Experimental Section

Biological Evaluation:
Cell Culture

A synthesized cDNA fragment encoding human Kv7.3 and human Kv7.2 separated by a P2A sequence was inserted into the pcDNA5/FRT/TO vector using the BamHI and XhoI restriction sites. The construct was then transfected into HEK Flp-In 293 cells using Lipofectamine2000. The transfected cells were grown for 48 hours in DMEM containing 10% (v/v) FBS and 1% PenStrep and subsequently maintained under selection in DMEM containing 10% (v/v) FBS, 1% PenStrep and 200 ug/mL Hygromycin B at 37° C. in a humidified atmosphere of 5% $CO_2$. The resultant stable hKv7.2/hKv7.3 cell line (HEK-hKv7.2/hKv7.3) was functionally tested with automated whole cell patch-clamp and displayed a typical Kv7-current which was sensitive to XE991 and potentiated by Retigabine.

Thallium Influx Assay

The thallium influx assay for potassium channel activation was performed analogously to a published procedure (C. D. Weaver, et al., J Biomol Screen 2004, 9, 671-677) using the FLIPR Potassium Assay kit (Molecular Devices). HEK-hKv7.2/hKv7.3 cells were plated onto 96-well, black-walled, clear-bottomed culture plates (Corning, Acton, Mass., USA) at a density of 80,000 cells/well (100 µl/well) if the cells were assayed the following day, or 40,000 cells/well (100 µl/well) if the cells were assayed two days after seeding.

On the assay day, the medium was removed after which 50 uL/well of test compound diluted to 2× final concentration in HBSS containing 20 mM HEPES, and 50 uL/well of 2× dye load buffer were added. The cells were then incubated for 60 min at room temperature in the dark. Chloride-free stimulation buffer containing $Tl^+$ and $K^+$ at 5× final concentration (5× concentration: 5 mM in both cases) and test compound at 1× final concentration, were prepared during the incubation. The cells were then assayed in a FDSS7000EX Functional Drug Screening System (Hamamatsu). Following 60 sec of baseline fluorescence signal reading at 0.1 Hz, and 10 sec at 1 Hz, 25 uL/well of stimulation buffer were added and the fluorescence continuously measured for 50 sec at 1 Hz followed, by 4 min at 0.1 Hz. Compound effect was quantified using AUC as readout and normalized to a reference compound, which was included on each plate.

Compound Effects

In the assay described above, the compounds of the invention had the following biological activity:

| Example | $EC_{50}$, nM |
|---|---|
| 1a | 7600 |
| 1b | 420 |
| 2a | 10000 |
| 2b | 1800 |
| 3a | 2800 |
| 3b | 2400 |

-continued

| Example | $EC_{50}$, nM |
|---|---|
| 4a | 1700 |
| 4b | 2900 |
| 5a | 1200 |
| 5b | 4500 |
| 6a | 2500 |
| 6b | 1100 |
| 7a | 4000 |
| 7b | 25000 |
| 8a | 4800 |
| 8b | 1200 |
| 9a | 1500 |
| 9b | 9200 |
| 10a | 660 |
| 10b | 4100 |
| 11a | 5400 |
| 11b | 1700 |
| 12a | 1300 |
| 12b | 6200 |
| 13a | 960 |
| 13b | 360 |
| 14a | 5200 |
| 14b | 1300 |
| 15a | 3700 |
| 15b | 650 |
| 16a | 2600 |
| 16b | 430 |
| 17 | 1500 |
| 18 | 950 |
| 19 | 940 |
| 20 | 1500 |
| 21 | 1000 |
| 22 | 4500 |
| 23 | 1500 |
| 24 | 2400 |
| 25 | 1900 |
| 26 | 960 |
| 27 | 2300 |
| 28 | 3200 |
| 29 | 5400 |
| 30 | 1800 |
| 31 | 2600 |
| 32 | 2500 |
| 33 | 2100 |
| 34 | 2500 |
| 35 | 3500 |
| 36a | 2700 |
| 36b | 16000 |

Synthesis of the Compounds of the Invention:
General Methods:

General procedures for synthesis of intermediates and the compounds of general Formula I are described in reaction Scheme 1, and are specifically illustrated in the preparations and Examples. Within the scope of the present invention are variations of the described procedures, which are known to a person skilled in the art.

The compounds of the invention are prepared as described in Scheme 1. Several of the compounds of general Formula I contain two chiral carbon atoms, and are formed as a mixture of diastereomers. When this is the case, the diastereomers may be separated, to yield the single stereoisomers Ia and Ib.

Scheme 1

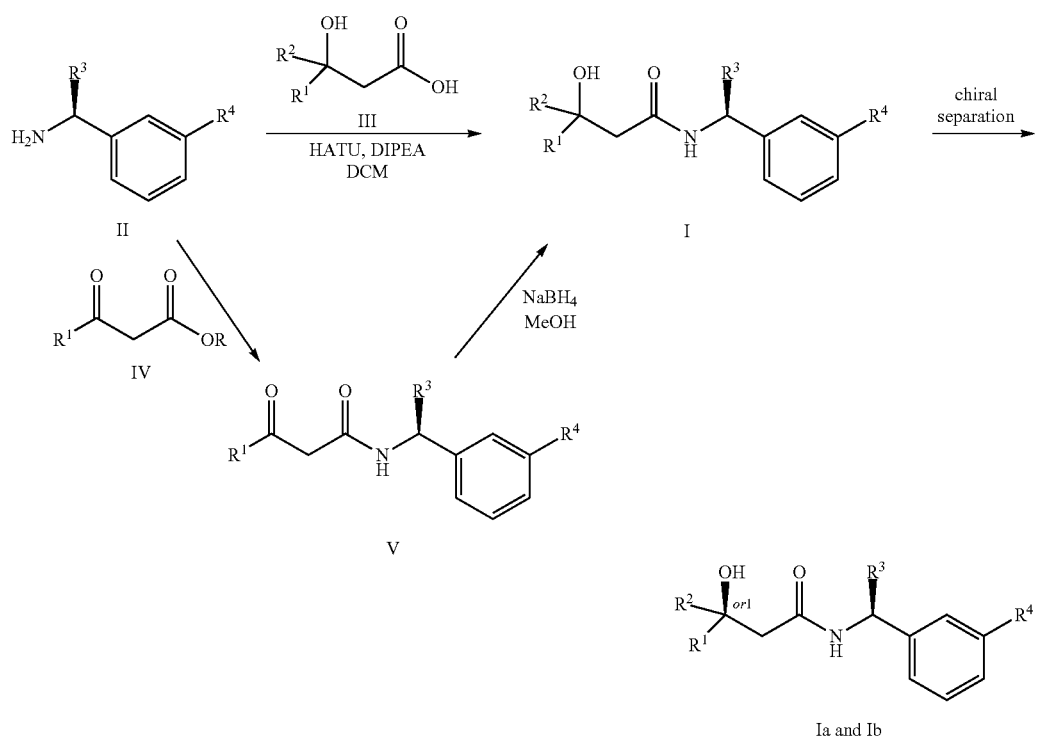

Ia and Ib

Scheme I depicts the preparation of the compounds of general Formula I by two general routes. The first route is the synthesis of compounds of Formula I by reaction of an enantiomerically pure amine of general Formula II, and an acid of general Formula III, through methodology well known in the art for the conversion of an acid and an amine into an amide. This methodology includes the formation of reactive derivatives of the acid of Formula III, including, but not limited to, activated esters and reactive mixed anhydrides, followed by condensation with amines of general Formula II. One such methodology is performing the condensation in the presence of (1-[bis(dimethylamino)methylene]-1H-1,2,3-triazolo[4,5-b]pyridinium 3-oxid hexafluorophosphate (HATU) and a suitable base such as diisopropylethylamine (DIPEA), in a solvent such as dichloromethane (DCM).

Alternatively, when $R^2$ is H, the compounds of general Formula I can be prepared via a second general route, in which intermediates of general Formula V, are treated with a suitable reducing agent such as $NaBH_4$, in a suitable solvent such as methanol. The intermediates of Formula V can be obtained from enantiomerically pure amines of general Formula II, and a carboxylic acid of general Formula IV (R=H). This transformation can be effected using similar reaction conditions as described above for the condensation of II and III to form I.

A variation of this procedure is the direct coupling reaction between a chiral amine of general Formula II and a carboxylic acid ester of general Formula IV (R=Me, Et). This reaction can be performed by heating the reactants to reflux in a suitable solvent such as toluene, in the presence of a suitable base such as DIPEA, and in the presence of a catalytic amount of a suitable catalyst such as 4-dimethylamino pyridine (DMAP).

The optically active amines of general Formula II can be prepared as outlined in Scheme 2a:

Scheme 2a

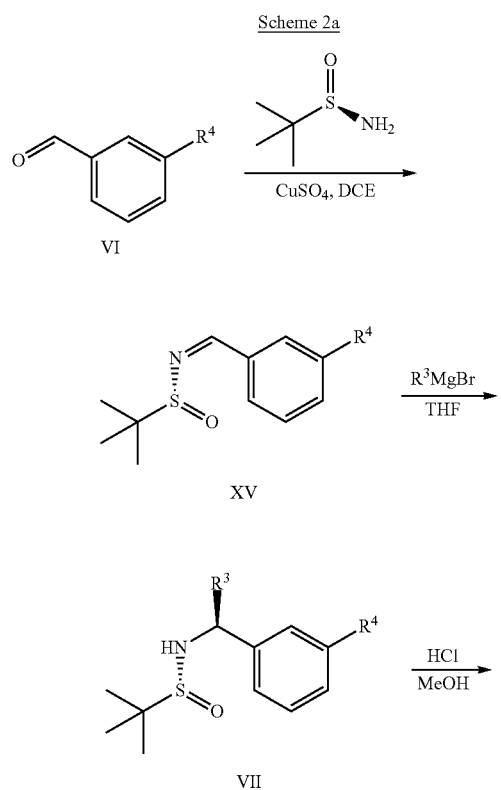

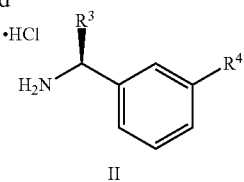

II

Aldehydes of general Formula VI can be condensed with (R)-2-methylpropane-2-sulfinamide in a suitable solvent such as dichloroethane, in the presence of a drying agent, such as titanium(IV)isopropoxide, or cupric sulfate. The formed sulfinyl imine XV is treated with $R^3MgBr$ in a suitable inert solvent such as THF, to yield the corresponding substituted (R)-2-methyl-N—((S)-1-aryl-alkyl)propane-2-sulfinamides VII, which are converted to the compounds of general Formula II by treatment with an appropriate acid in an appropriate solvent, such as HCl in MeOH.

In variations of this procedure, an $R^3$ substituent bearing a functional group can be further modified, by standard functional group conversion methodology known to the chemist skilled in the art. Examples of such manipulations for the preparation of chiral amines are illustrated in Scheme 2b. An intermediate of general Formula VII in which $R^3$=allyl can be formed from XV and allyl-MgBr, and can undergo catalytic reduction to R3=n-propyl, using $H_2$ (g) in the presence of a catalyst such as Pd/C, in a suitable solvent such as ethyl acetate. Alternatively, the intermediate of general Formula VII in which $R^3$=allyl can undergo di-hydroxylation followed by oxidative cleavage to yield an intermediate VII in which $R^3$=acetaldehyde, by treatment with suitable catalysts such as $K_2OsO_4$ and $NaIO_4$, in the presence of a suitable base such as 2,6-lutidine, and in a suitable solvent such as dioxane/$H_2O$. The obtained aldehyde can undergo additional transformations; for example exchange of oxygen for two fluorine atoms by treatment with a suitable reagent such as (diethylamino)sulfur trifluoride (DAST), in a suitable solvent such as DCM. In a final step, chiral amines can be obtained by hydrolysis as described above.

As another example, an intermediate of general Formula XVI in which $R^3$ is an acetic acid ester, can be formed from XV in a reaction with ethyl 2-bromo acetate, in the presence of CuCl and activated Zn, in a suitable solvent such as THF. The ester group can be further derivatized by transformations known to the skilled chemist. For example, the ester can be reduced to a primary alcohol, by treatment with a suitable reducing agent such as $LiAlH_4$, in a suitable solvent, such as THF. The alcohol obtained may also be further derivatized through transformations known to the skilled practitioner. For example, the alcohol may be transformed into a leaving group through activation with a reagent such as mesyl chloride in the presence of a suitable base such as triethylamine (TEA), in a suitable solvent such as DCM. The resulting mesylates can be reacted with a suitable nucleophile, such as potassium cyanide, in a suitable solvent such as DMSO.

Scheme 2b:

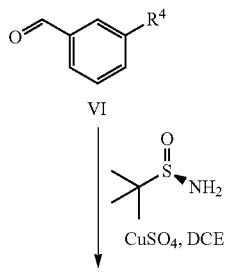

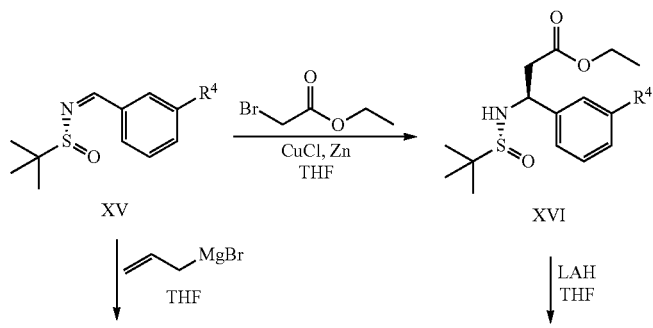

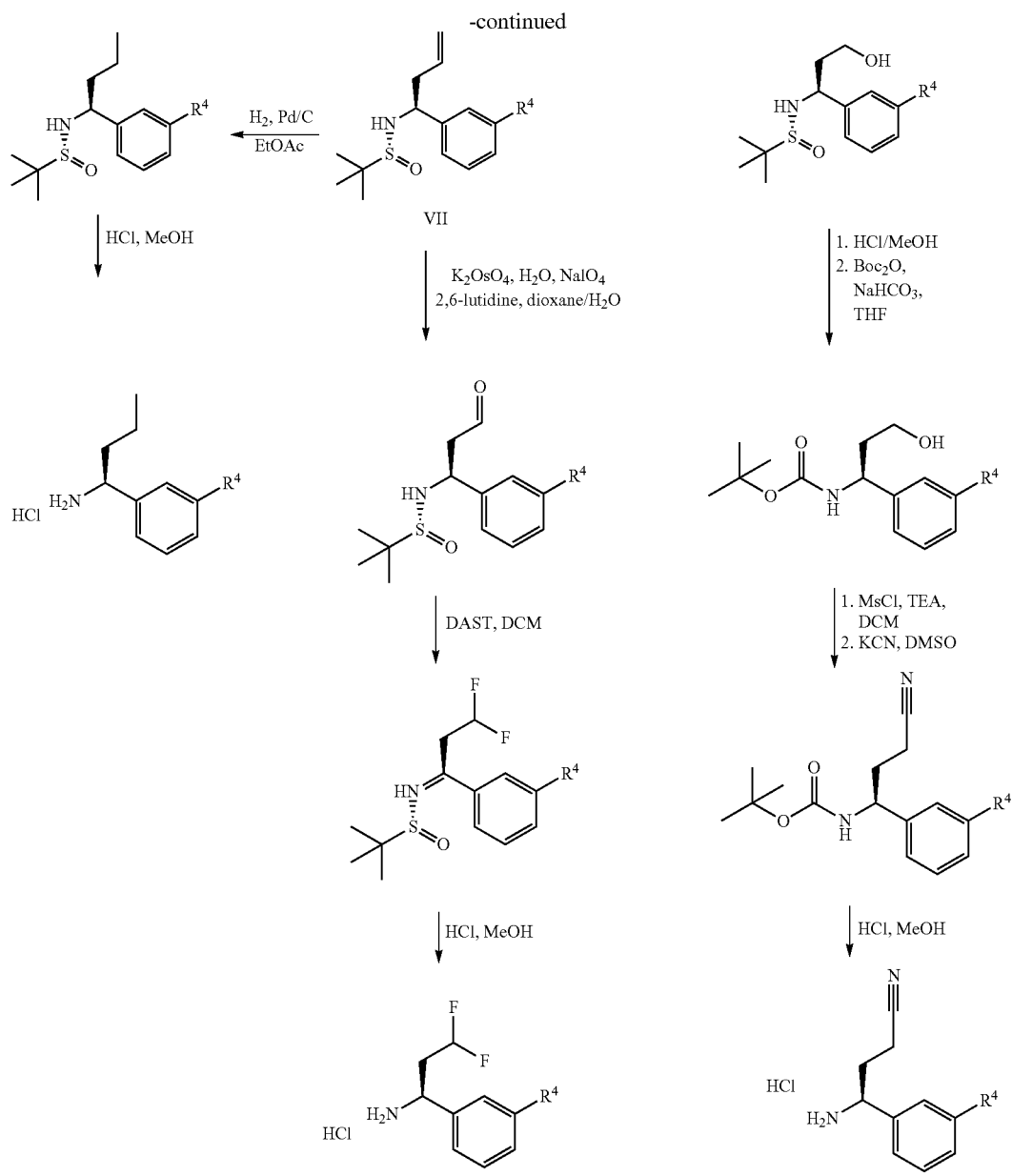
Aldehydes of general Formula VI can also be transformed into chiral amines of general Formula II via an alternative strategy, as illustrated in Scheme 2c:
Scheme 2c
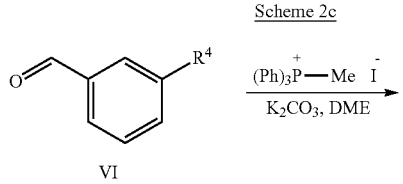
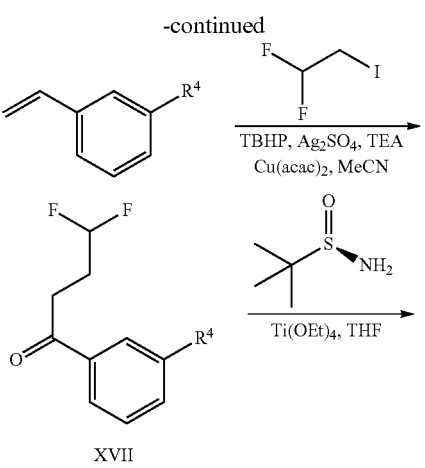

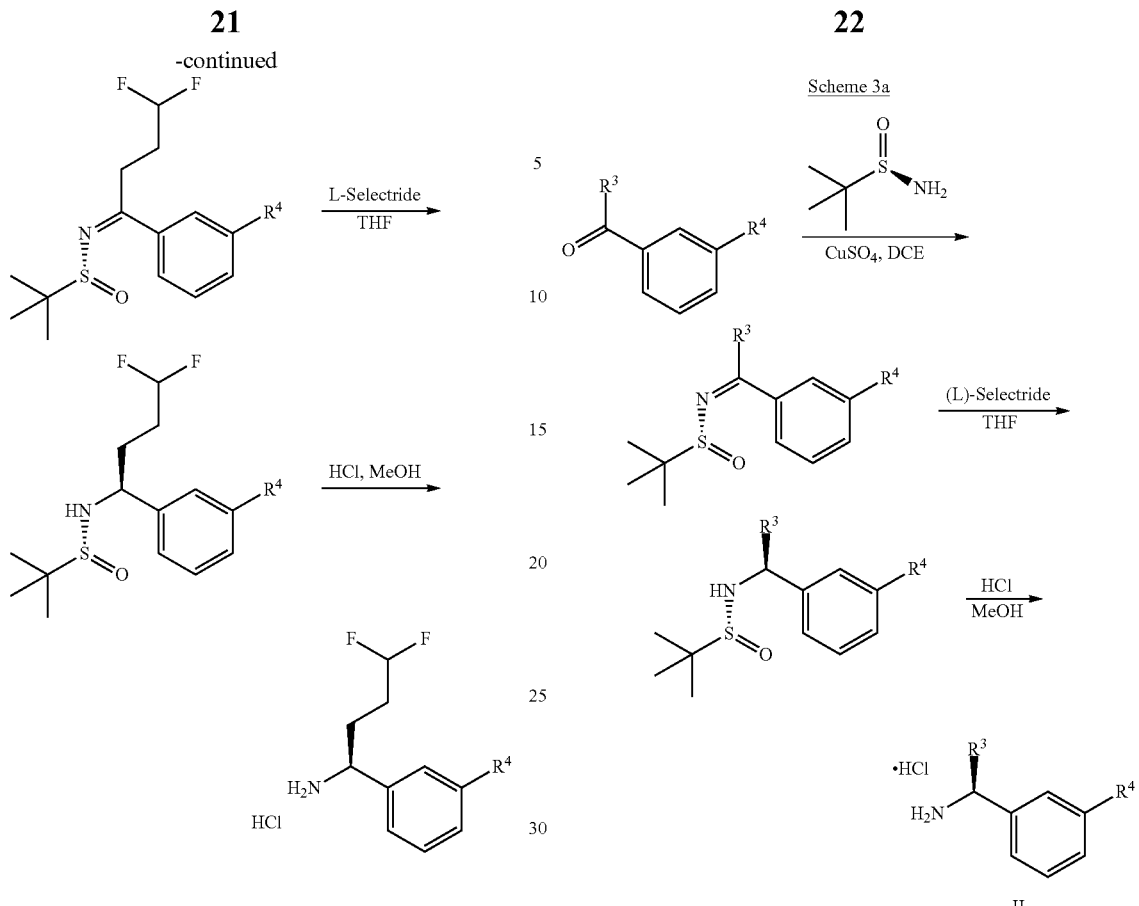

Scheme 3a

Following this procedure, suitably substituted benzaldehydes VI can be transformed into corresponding suitably substituted styrenes, using Wittig methodology know to the skilled chemist. These intermediates can undergo an alkylation-oxidation reaction to form keto-intermediates XVII. Intermediates of general Formula XVII can be condensed with (R)-2-methylpropane-2-sulfinamide in a suitable solvent such as dichloroethane, in the presence of a suitable drying agent, such as titanium(IV)ethoxide. The formed sulfinyl imine can be reduced with a suitable reducing agent such as L-Selectride, in a suitable inert solvent such as THF, to yield the corresponding suitably substituted (R)-2-methyl-N—((S)-1-aryl-alkyl)propane-2-sulfinamide, which can be converted to chiral amines of general Formula II by treatment with an appropriate acid in an appropriate solvent, such as HCl in MeOH.

The skilled artisan will recognise that other transformations are possible from several of the intermediates; the present invention is intended to include such alternative transformations.

The aldehydes of Formula VI, used to prepare the compounds of the invention, are commercially available, or may be prepared as described in the literature, see Journal of Medicinal Chemistry, 45(18), 3891-3904; 2002.

In another procedure, the chiral amines of Formula II can be obtained from an aryl ketone, through hydride reduction of the intermediate sulfinyl imine obtained from reaction with (R)-2-methylpropane-2-sulfinamide, with a reagent such as L-Selectride; as shown in Scheme 3a.

A variation of this procedure is illustrated in Scheme 3b. In this procedure, further $R^3$ substituents which are ethers, can be installed from a common alpha bromoacetophenone intermediate XI, obtained by bromination of a suitably substituted acetophenone. Examples include, but are not limited to introduction of fluoroalkyl methylene ether groups as $R^3$. Thus, using this methodology, suitably substituted bromoacetophenone can be reacted with a fluoroalkoxy donor, such as trifluoromethyl trifluoromethanesulfonate and KF under Finkelstein conditions, in a suitable solvent such as dimethylacetamide (DMA), to give intermediate XII, which can be further transformed into chiral amines as described above. Other examples include, but are not limited to, introduction of alkyl methylene ethers as $R^3$. Thus, suitably substituted bromoacetophenone can be transformed into acyl diazo intermediate XIII, by reaction with 4-methyl-N'-(p-tolylsulfonyl)benzenesulfonohydrazide in the presence of a suitable base, such as 1,8-diazabicyclo[5.4.0]undec-7-ene (DBU), and in a suitable solvent such as THF. The intermediate XIII can undergo a carbene formation reaction, by treatment with a suitable catalyst such as Indium triflate, in a suitable solvent such as toluene. The formed carbene can be trapped in situ by a suitable alcohol, to yield alkoxy keto intermediates XIV. From intermediate XIV, chiral amines of Formula II can be obtained through standard manipulations as described above.

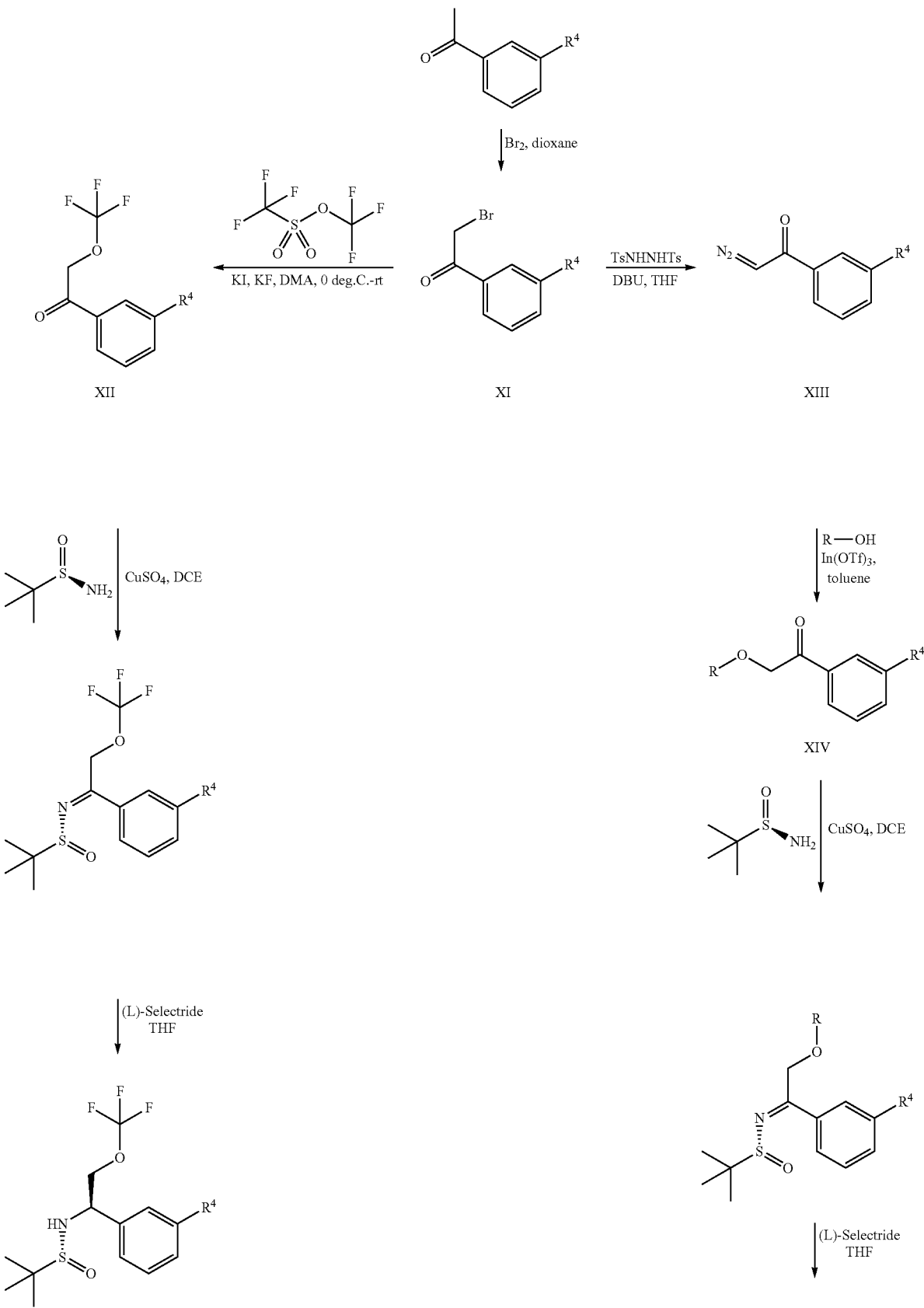

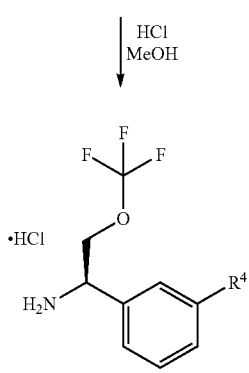
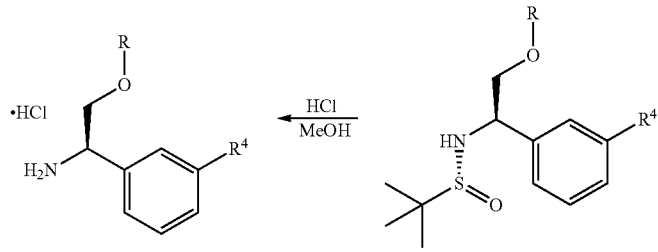

The suitably substituted ketones or acetophenones used to prepare the compounds of the invention, are commercially available, or may be prepared by methods known to the person skilled in the art.

The skilled artisan will recognise that other transformations are possible from intermediates of general Formula XI; the present invention is intended to include such alternative transformations.

Another procedure suited for accessing chiral amines of general Formula II, in which $R^3$ is an ether, is outlined in Scheme 4.

Scheme 4

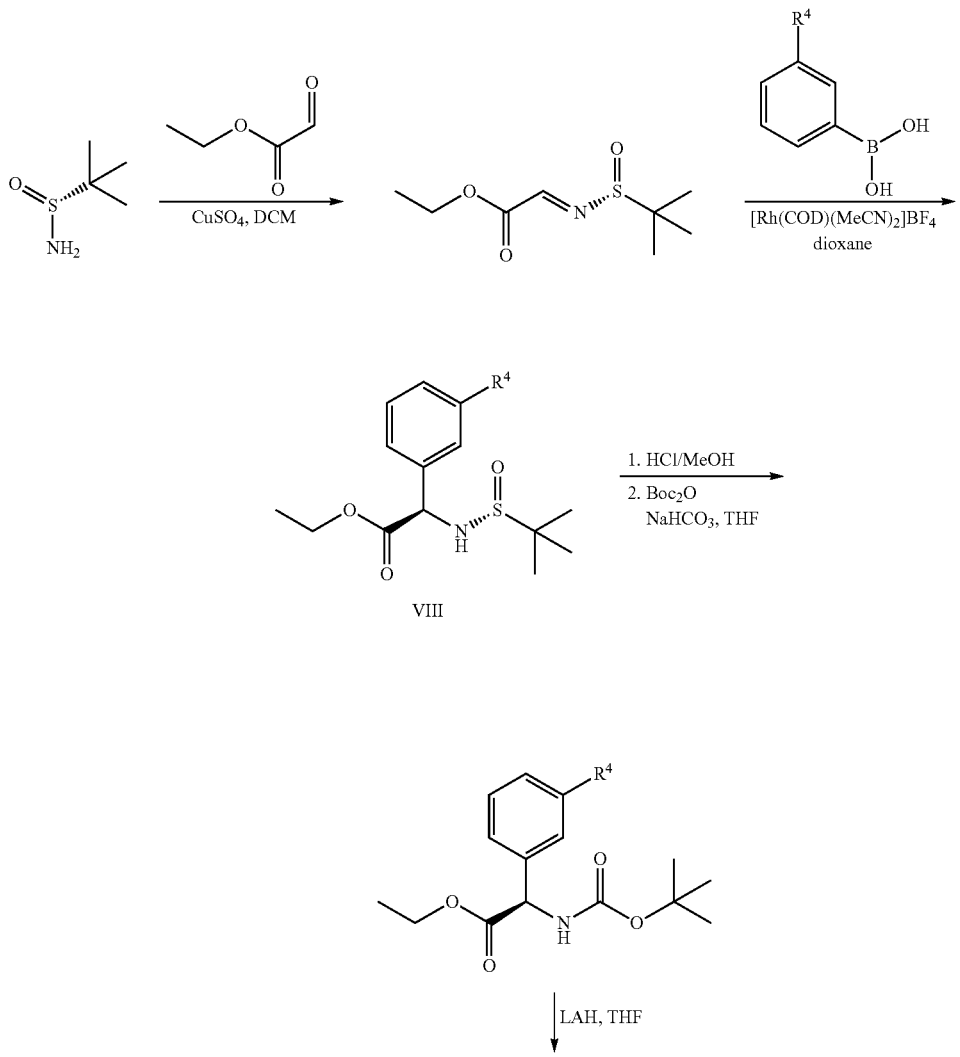

-continued

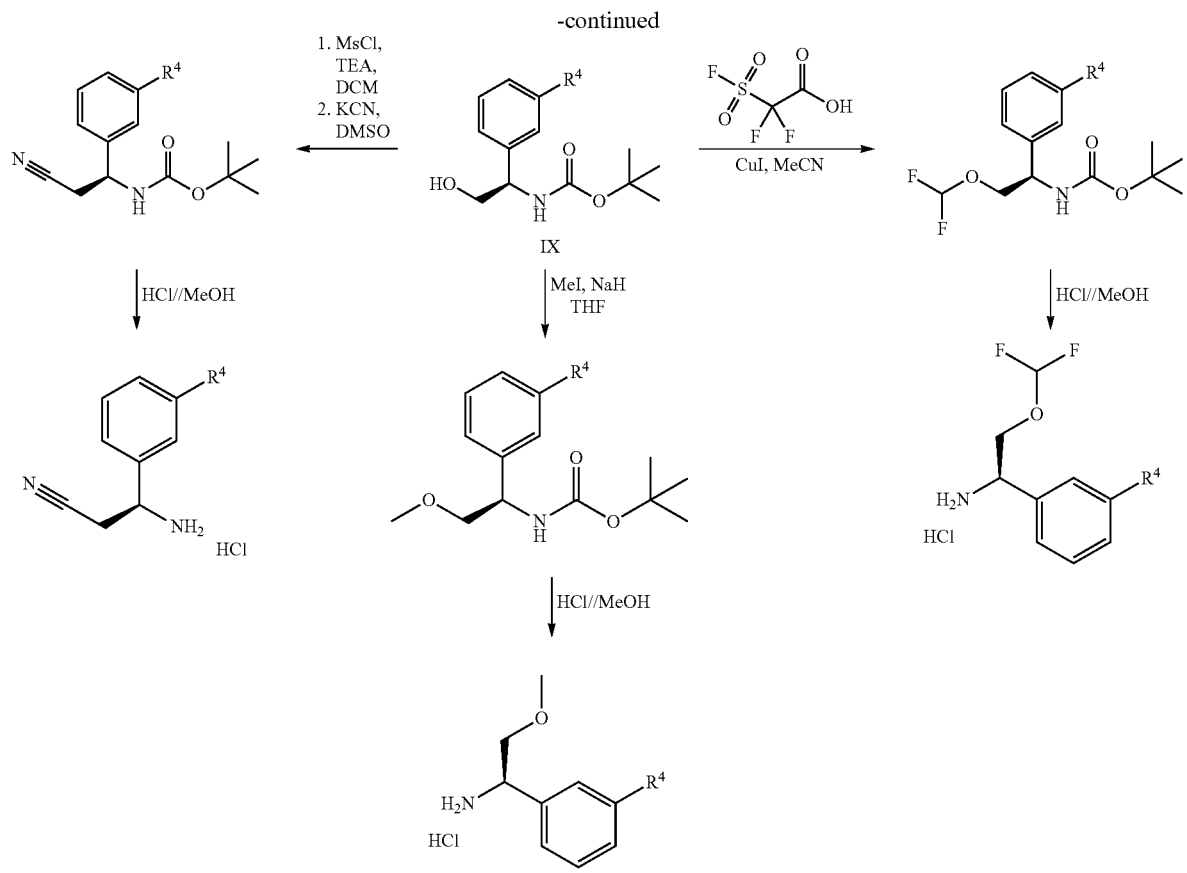

In this procedure, glyoxylate sulfinyl imine, formed in a condensation reaction between a glyoxylic ester and (R)-2-methylpropane-2-sulfinamide, can be reacted with a suitably substituted boronic acid using a suitable catalyst such as bis(acetonitrile)(1,5-cyclooctadiene)rhodium(I) tetra-fluoroborate, in a suitable solvent such as dioxane, as described in JP 2017/095366A. The resulting intermediates VIII can be hydrolysed, re-protected with a suitable protecting group such as Boc under standard conditions, and subjected to ester reduction under suitable conditions such as LiAlH$_4$ in THF, to yield alcohol intermediates of general Formula IX. Intermediates of Formula IX may be further derivatised to access the desired R$^3$ substituent. For example, the alcohol group in intermediates IX may be difluoromethylated using a suitable reagent such as 2,2-difluoro-2-(fluorosulfonyl) acetic acid under conditions such as CuI activation, in a suitable solvent such as acetonitrile, or; the alcohol group in IX may be alkylated using simple alkyl halides, such as methyl iodide, in the presence of a suitable base such as NaH in a suitable solvent such as THF. Alternatively, the alcohol of intermediates IX may be transformed into a leaving group through activation with a reagent such as mesyl chloride in the presence of a suitable base such as TEA, in a suitable solvent such as DCM. The resulting mesylates can be reacted with a suitable nucleophile, such as potassium cyanide, in a suitable solvent such as DMSO.

The skilled artisan will recognise that other transformations are possible from intermediates of general Formula IX; the present invention is intended to include such alternative transformations.

The carboxylic acids of general Formula III can be prepared as outlined in Scheme 5:

Scheme 5

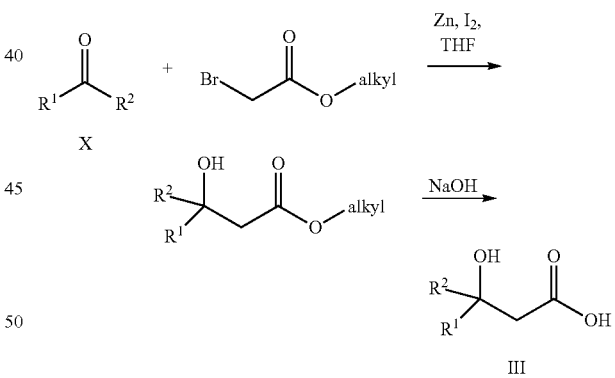

Ketones of general Formula X are reacted with an alkyl ester of bromoacetic acid activated with, for example, Zn and iodine, to yield the corresponding aldol adduct. In an alternative procedure, the bromoacetic acid ester can be activated using Zn and TMSCl (trimethylsilyl chloride). In a final step, hydrolysis of the alkyl ester is accomplished by treatment with an appropriate base such as NaOH or LiOH in an appropriate solvent, such as water, or an alcohol in water, and followed by acidification with an appropriate acid to yield the compounds of Formula III.

Carboxylic acid ester of general Formula IV (R=Me, Et) are commercially available, or may be prepared as outlined in Scheme 6:

Scheme 6

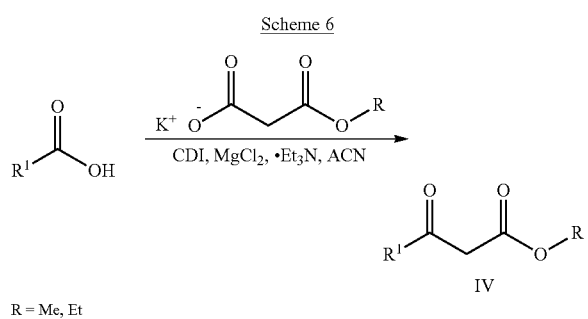

R = Me, Et

Suitably substituted carboxylic acids can be activated using a suitable reagent such as CDI and condensed with potassium 3-ethoxy-3-oxo-propanoate in the presence of $MgCl_2$, to yield intermediates of general Formula IV.

$^1$H NMR spectra were recorded at 400.13 MHz on a Bruker Avance III 400 instrument or at 300.13 MHz on a Bruker Avance 300 instrument. Deuterated dimethyl sulfoxide or deuterated chloroform was used as solvent. Tetramethylsilane was used as internal reference standard. Chemical shift values are expressed in ppm-values relative to tetramethylsilane. The following abbreviations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and brs=broad singlet.

Chromatographic systems and methods to evaluate chemical purity (LCMS methods) and chiral purity (SFC and HPLC methods) are described below.

LCMS Method 1: Apparatus: Agilent 1200 LCMS System with ELS Detector.

| Column | Waters Xbridge-C18, 50 × 2 mm, 5 μm |
|---|---|
| Flow rate | 0.8 mL/min |
| Run time | 4.5 min. |
| Wavelenght | 254 nm |
| Column temp | 50° C. |
| Ion source | ESI |
| Solvent A | Water + 0.04% TFA |
| Solvent B | MeCN + 0.02% TFA |

| Gradient | Time (min) | A % | B % |
|---|---|---|---|
| | 0 | 99 | 1 |
| | 3.4 | 0 | 100 |
| | 4 | 0 | 100 |
| | 4.01 | 99 | 1 |
| | 4.5 | 99 | 1 |

LCMS Method 2: Apparatus: Agilent 1200 LCMS System with ELS Detector

| Column | Waters XBridge ShieldRP18, 50 × 2.1 mm, 5 μm |
|---|---|
| Flow rate | 0.8 mL/min |
| Run time | 4.5 min. |
| Wavelenght | 254 nm |
| Column temp | 40° C. |
| Ion source | ESI |
| Solvent A | Water + 0.05% $NH_3 \cdot H_2O$ |
| Solvent B | MeCN |

| Gradient | Time (min) | A % | B % |
|---|---|---|---|
| | 0 | 95 | 5 |
| | 3.4 | 0 | 100 |
| | 4 | 0 | 100 |
| | 4.01 | 95 | 5 |
| | 4.5 | 95 | 5 |

LCMS Method 3: Apparatus Agilent 1200 LCMS System with ELS Detector

| Column | Waters Xbridge-C18, 50 × 2 mm, 5 μm |
|---|---|
| Flow rate | 0.8 mL/min |
| Run time | 4.5 min. |
| Wavelenght | 254 nm |
| Column temp | 50° C. |
| Ion source | ESI |
| Solvent A | Water + 0.04% TFA |
| Solvent B | MeCN + 0.02% TFA |

| Gradient | Time (min) | A % | B % |
|---|---|---|---|
| | 0 | 90 | 10 |
| | 3.4 | 0 | 100 |
| | 4 | 0 | 100 |
| | 4.01 | 90 | 10 |
| | 4.5 | 90 | 10 |

LCMS Method 4: Apparatus Shimadzu LC20ADXR LCMS System with ESI Detector

| Column | Poroshell HPH-C18, 50 × 2.7 mm, 3 μm |
|---|---|
| Flow rate | 1.2 mL/min |
| Run time | 3 min. |
| Wavelenght | 190-400 nm |
| Column temp | 40° C. |
| Ion source | ESI |
| Solvent A | Water + 0.04% $NH_4HCO_3$ |
| Solvent B | MeCN |

| Gradient | Time (min) | A % | B % |
|---|---|---|---|
| | 0 | 95 | 5 |
| | 2.2 | 5 | 95 |
| | 2.8 | 5 | 95 |
| | 3 | 95 | 5 |

Chiral Analytical Methods:
SFC Method 1: Apparatus: Waters UPC2

| Column | Chiralpak AD-3 150 × 4.6 mm I.D., 3 μm |
|---|---|
| Flow rate | 2.5 mL/min |
| Run time | 8 min. |
| Wavelenght | 220 nm |
| Column temp | 35° C. |
| Solvent A | EtOH + 0.05% diethylamine |

| Gradient | Time (min) | A % |
|---|---|---|
| | 0 | 5 |
| | 4.5 | 40 |
| | 7 | 40 |
| | 7.01 | 5 |
| | 8 | 5 |

SFC Method 2: Apparatus: Agilent 1260

| Column | (S,S)Whelk-01 100 × 4.6 mm I.D., 5 um |
|---|---|
| Flow rate | 2.5 mL/min |

-continued

| | |
|---|---|
| Run time | 7 min. |
| Wavelenght | 220 nm |
| Column temp | 40° C. |
| Solvent A | EtOH + 0.05% diethylamine |

| Gradient | Time (min) | A % |
|---|---|---|
| | 0 | 5 |
| | 5.5 | 40 |
| | 5.51 | 5 |
| | 7 | 5 |

SFC Method 3: Apparatus: Agilent 1260

| | |
|---|---|
| Column | Chiralpak AS-3 150 × 4.6 mm I.D., 3 um |
| Flow rate | 2.5 mL/min |
| Run time | 7 min. |
| Wavelenght | 220 nm |
| Column temp | 40° C. |
| Solvent A | EtOH + 0.05% diethylamine |

| Gradient | Time | A % |
|---|---|---|
| | 0 | 5 |
| | 5 | 40 |
| | 5.5 | 40 |
| | 5.51 | 5 |
| | 7 | 5 |

SFC Method 4: Apparatus: Agilent 1260

| | |
|---|---|
| Column | Chiralpak AD-3 150 × 4.6 mm I.D., 3 um |
| Flow rate | 2.5 mL/min |
| Run time | 7 min. |
| Wavelenght | 220 nm |
| Column temp | 40° C. |
| Solvent A | iPrOH + 0.05% diethylamine |

| Gradient | Time | A % |
|---|---|---|
| | 0 | 5 |
| | 5.5 | 40 |
| | 5.51 | 5 |
| | 7 | 5 |

SFC Method 5: Apparatus: Agilent 1260

| | |
|---|---|
| Column | Lux Cellulose-2 150 × 4.6 mm I.D., 3 μm |
| Flow rate | 2.5 mL/min |
| Run time | 10 min. |
| Wavelenght | 220 nm |
| Column temp | 40° C. |
| Solvent A | MeOH + 0.05% diethylamine |

| Gradient | Time | A % |
|---|---|---|
| | 0 | 5 |
| | 5.5 | 40 |
| | 8.5 | 40 |
| | 8.51 | 5 |
| | 10 | 5 |

SFC method 6: Apparatus: Agilent 1260

| | |
|---|---|
| Column | Chiralpak AD-3 150 × 4.6 mm I.D., 3 um |
| Flow rate | 2.5 mL/min |
| Run time | 7 min. |
| Wavelenght | 220 nm |
| Column temp | 35° C. |
| Solvent A | EtOH + 0.05% diethylamine |

| Gradient | Time (min) | A % |
|---|---|---|
| | 0 | 5 |
| | 5.5 | 40 |
| | 5.51 | 5 |
| | 7 | 5 |

SFC Method 7: Apparatus: Waters UPC2

| | |
|---|---|
| Column | Chiralpak AS-3 150 × 4.6 mm I.D., 3 um |
| Flow rate | 2.5 mL/min |
| Run time | 7 min. |
| Wavelenght | 220 nm |
| Column temp | 35° C. |
| Solvent A | EtOH + 0.05% diethylamine |

| Gradient | Time (min) | A % |
|---|---|---|
| | 0 | 5 |
| | 5 | 40 |
| | 5.5 | 40 |
| | 7 | 5 |

SFC Method 8: Apparatus: Waters UPC2

| | |
|---|---|
| Column | ChiralPak AD-3 150 × 4.6 mm I.D., 3 um |
| Flow rate | 2.5 mL/min |
| Run time | 10 min. |
| Wavelenght | 210 nm |
| Column temp | 35° C. |
| Solvent A | EtOH + 0.05% diethylamine |

| Gradient | Time | A % |
|---|---|---|
| | 0 | 5 |
| | 5 | 40 |
| | 7.5 | 40 |
| | 7.51 | 5 |
| | 10 | 5 |

SFC Method 9: Apparatus: Waters UPC2

| | |
|---|---|
| Column | Chiralcel OJ-3 150 × 4.6 mm I.D., 3 um |
| Flow rate | 2.5 mL/min |
| Run time | 7 min. |
| Wavelenght | 220 nm |
| Column temp | 35° C. |
| Solvent A | MeOH + 0.05% diethylamine |

| Gradient | Time | A % |
|---|---|---|
| | 0 | 5 |
| | 5 | 40 |
| | 5.5 | 5 |
| | 7 | 5 |

SFC Method 10: Apparatus: Agilent 1260

| | |
|---|---|
| Column | Chiralpak AY-3 150 × 4.6 mm I.D., 3 um |
| Flow rate | 2.5 mL/min |
| Run time | 7 min. |
| Wavelenght | 220 nm |
| Column temp | 40° C. |
| Solvent A | EtOH + 0.05% diethylamine |

-continued

| Gradient | Time | A % |
|---|---|---|
| | 0 | 5 |
| | 5.5 | 40 |
| | 5.51 | 5 |
| | 7 | 5 |

SFC Method 11: Apparatus: Agilent 1260

| Column | (R,R)Whelk-01 100 × 4.6 mm I.D., 3 um |
|---|---|
| Flow rate | 2.5 mL/min |
| Run time | 10 min. |
| Wavelenght | 220 nm |
| Column temp | 40° C. |
| Solvent A | MeOH + 0.05% diethylamine |

| Gradient | Time (min) | A % |
|---|---|---|
| | 0 | 5 |
| | 5.5 | 40 |
| | 8.5 | 40 |
| | 8.51 | 5 |
| | 10 | 5 |

SFC Method 12: Apparatus: Waters UPC2

| Column | (S,S)Whelk-01 100 × 4.6 mm I.D., 3 um |
|---|---|
| Flow rate | 2.8 mL/min |
| Run time | 8 min. |
| Wavelength | 254 nm |
| Column temp | 35° C. |
| Solvent A | iPrOH + 0.05% diethylamine |

| Gradient | Time (min) | A % |
|---|---|---|
| | 0 | 5 |
| | 4 | 40 |
| | 6.5 | 40 |
| | 8.51 | 5 |
| | 8 | 5 |

SFC Method 13: Apparatus: Waters UPC2

| Column | ChiralPak AS-3 150 × 4.6 mm I.D., 3 um |
|---|---|
| Flow rate | 2.5 mL/min |
| Run time | 7 min. |
| Wavelenght | 220 nm |
| Column temp | 35° C. |
| Solvent A | iPrOH + 0.05% diethylamine |

| Gradient | Time | A % |
|---|---|---|
| | 0 | 5 |
| | 5 | 40 |
| | 5.5 | 5 |
| | 7 | 5 |

SFC Method 14: Apparatus: Waters UPC2

| Column | ChiralPak IG-3 100 × 4.6 mm I.D., 3 um |
|---|---|
| Flow rate | 2.8 mL/min |
| Run time | 8 min. |
| Wavelenght | 220 nm |
| Column temp | 35° C. |
| Solvent A | EtOH + 0.05% diethylamine |

| Gradient | Time | A % |
|---|---|---|
| | 0 | 5 |
| | 4 | 40 |
| | 6.5 | 40 |
| | 6.51 | 5 |
| | 8 | 5 |

SFC Method 15: Apparatus: Waters UPC2

| Column | Cellulose-2 150 × 4.6 mm I.D., 5 μm |
|---|---|
| Flow rate | 2.5 mL/min |
| Run time | 10 min. |
| Wavelenght | 254 nm |
| Column temp | 35° C. |
| Solvent A | iPrOH + 0.05% diethylamine |

| Gradient | Time | A % |
|---|---|---|
| | 0 | 5 |
| | 5 | 40 |
| | 7.5 | 40 |
| | 7.51 | 5 |
| | 10 | 5 |

SFC method 16: Apparatus: Waters UPC2

| Column | Cellulose-2 150 × 4.6 mm I.D., 5 μm |
|---|---|
| Flow rate | 2.5 mL/min |
| Run time | 10 min. |
| Wavelenght | 220 nm |
| Column temp | 35° C. |
| Solvent A | EtOH + 0.05% diethylamine |

| Gradient | Time | A % |
|---|---|---|
| | 0 | 5 |
| | 5 | 40 |
| | 7.5 | 40 |
| | 7.51 | 5 |
| | 10 | 5 |

SFC method 17: Apparatus: Waters UPC2

| Column | Cellulose-2 150 × 4.6 mm I.D., 5 μm |
|---|---|
| Flow rate | 2.5 mL/min |
| Run time | 10 min. |
| Wavelenght | 220 nm |
| Column temp | 35° C. |
| Solvent A | MeOH + 0.05% diethylamine |

| Gradient | Time | A % |
|---|---|---|
| | 0 | 5 |
| | 5 | 40 |
| | 7.5 | 40 |
| | 7.51 | 5 |
| | 10 | 5 |

SFC Method 18: Apparatus: Agilent

| Column | Lux Cellulose-4 100 × 4.6 mm I.D., 3 μm |
|---|---|
| Flow rate | 2 mL/min |
| Run time | 6.5 min. |
| Wavelenght | 220 nm |
| Column temp | 35° C. |
| Solvent A | EtOH |

| Gradient | Time | A % |
|---|---|---|
| | 0 | 5 |
| | 2 | 20 |

| | 5 | 20 |
| | 6.5 | 5 |

SFC Method 19: Apparatus: Agilent

| Column | Chiralpak OD-3 150 × 4.6 mm I.D., 3 μm |
|---|---|
| Flow rate | 2.5 mL/min |
| Run time | 7 min. |
| Wavelenght | 220 nm |
| Column temp | 40° C. |
| Solvent A | EtOH + 0.05% diethylamine |

| Gradient | Time | A % |
|---|---|---|
| | 0 | 5 |
| | 5.5 | 40 |
| | 5.51 | 5 |
| | 7 | 5 |

SFC Method 20: Apparatus: Waters UPC2

| Column | ChiralPak AD-3 150 × 4.6 mm I.D., 3 μm |
|---|---|
| Flow rate | 2.5 mL/min |
| Run time | 10 min. |
| Wavelenght | 220 nm |
| Column temp | 35° C. |
| Solvent A | EtOH + 0.05% diethylamine |

| Gradient | Time | A % |
|---|---|---|
| | 0 | 5 |
| | 5 | 5 |
| | 5.5 | 40 |
| | 7.5 | 40 |
| | 7.51 | 5 |
| | 10 | 5 |

SFC Method 21: Apparatus: Waters UPC2

| Column | Cellulose 2 100 × 4.6 mm I.D., 3 μm |
|---|---|
| Flow rate | 2.8 mL/min |
| Run time | 8 min. |
| Wavelenght | 220 nm |
| Column temp | 35° C. |
| Solvent A | MeOH + 0.05% diethylamine |

| Gradient | Time | A % |
|---|---|---|
| | 0 | 5 |
| | 4 | 40 |
| | 6.5 | 40 |
| | 6.51 | 5 |
| | 8 | 5 |

SFC Method 22: Apparatus: Agilent 1260

| Column | Lux Cellulose-2 150 × 4.6 mm I.D., 3 μm |
|---|---|
| Flow rate | 2.5 mL/min |
| Run time | 7 min. |
| Wavelenght | 220 nm |
| Column temp | 40° C. |
| Solvent A | MeOH + 0.05% diethylamine |

| Gradient | Time | A % |
|---|---|---|
| | 0 | 5 |
| | 5.5 | 40 |
| | 5.51 | 5 |
| | 7 | 5 |

Chiral HPLC Method 1: Apparatus: SHIMADZU LC-20AB

| Column | Chiralpak AS-RH 150*4.6 mm I.D., 5 um |
|---|---|
| Flow rate | 0.8 mL/min |
| Run time | 25 min. |
| Wavelenght | 220 nm |
| Column temp | 30° C. |
| Solvent A | Water + 0.069% TFA |
| Solvent B | MeCN |

| Gradient | Time (min) | A % | B % |
|---|---|---|---|
| | 0 | 90 | 10 |
| | 25 | 20 | 80 |

Chiral HPLC Method 2: Apparatus: SHIMADZU LC-20AB

| Column | ChiralCel OD-RH 150 × 4.6 mm I.D., 5 um |
|---|---|
| Flow rate | 0.8 mL/min |
| Run time | 25 min. |
| Wavelenght | 220 nm |
| Column temp | 30° C. |
| Solvent A | Water + 0.07% TFA |
| Solvent B | MeCN |

| Gradient | Time | A % | B % |
|---|---|---|---|
| | 0 | 90 | 10 |
| | 14 | 20 | 80 |
| | 15 | 90 | 10 |
| | 25 | 90 | 10 |

Chiral HPLC Method 3: Apparatus: SHIMADZU LC-20AB

| Column | ChiralCel OD-RH 150 × 4.6 mm I.D., 5 um |
|---|---|
| Flow rate | 0.8 mL/min |
| Run time | 25 min. |
| Wavelenght | 220 nm |
| Column temp | 100° C. |
| Solvent A | Water + 0.07% TFA |
| Solvent B | MeCN |

| Gradient | Time | A % | B % |
|---|---|---|---|
| | 0 | 90 | 10 |
| | 14 | 20 | 80 |
| | 15 | 90 | 10 |
| | 25 | 90 | 10 |

Chiral HPLC Method 4: Apparatus: SHIMADZU LC-20AB

| Column | ChiralPak AD-RH 150 × 4.6 mm I.D., 5 um |
|---|---|
| Flow rate | 0.8 mL/min |
| Run time | 25 min. |
| Wavelenght | 220 nm |
| Column temp | 30° C. |
| Solvent A | Water + 0.07% TFA |
| Solvent B | MeCN |

| Gradient | Time | A % | B % |
|---|---|---|---|
| | 0 | 90 | 10 |
| | 14 | 20 | 80 |
| | 15 | 90 | 10 |
| | 25 | 90 | 10 |

Preparation of Intermediates

IIb: ((R)-2-(difluoromethoxy)-1-(3-(trifluoromethoxy)phenyl)ethan-1-amine

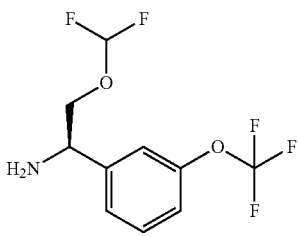 [SMILES: N[C@@H](COC(F)F)c1cccc(OC(F)(F)F)c1]

Step 1: Preparation of ethyl 2-[(R)-tert-butylsulfinyl]imino acetate

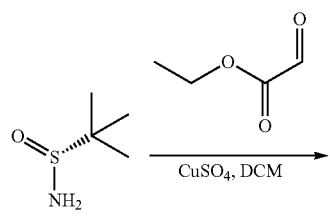

To a solution of ethyl 2-oxoacetate (7.5 g, 36.7 mmol) and (R)-2-methylpropane-2-sulfinamide (4.9 g, 40.4 mmol) in DCM (150 mL) was added CuSO₄ (12.9 g, 80.8 mmol), and the reaction mixture was stirred at 25° C. for 24 hours. The solid was filtered off, washed with ethyl acetate (50 mL) and the organic phases were combined and concentrated. The resulting residue was purified by column chromatography (silica gel, petroleum ether/ethyl acetate, 5/1) to yield the desired product (5.1 g, 67.6% yield).

Step 2: Preparation of ethyl (2R)-2-[[(R)-tert-butylsulfinyl]amino]-2-[3-(trifluoromethoxy)phenyl]acetate

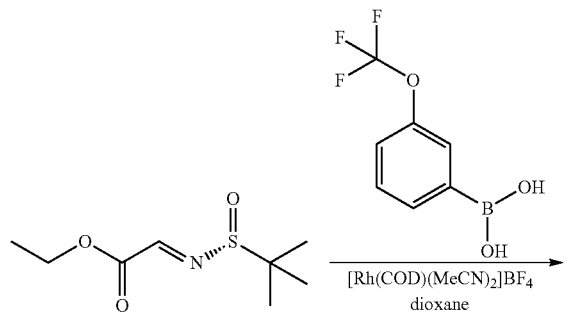

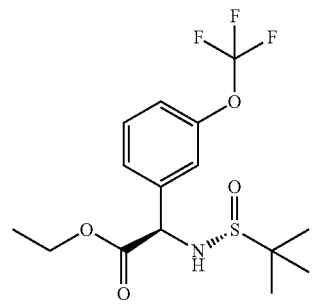

To a solution of ethyl-2-[(R)-tert-butylsulfinyl]iminoacetate (7 g, 34.1 mmol) and [3-(trifluoromethoxy)phenyl]boronic acid (8.4 g, 40.9 mmol) in dioxane (100 mL) was added [Rh(COD)(MeCN)₂]BF₄ (1.3 g, 3.4 mmol) and this mixture was stirred at 80° C. for 16 hours. The product was purified by silica gel chromatography (petroleum ether:ethyl acetate=5:1) to yield 9.8 g (78%).

Step 3: Preparation of ethyl (2R)-2-amino-2-[3-(trifluoro-methoxy)phenyl]acetate hydrochloride

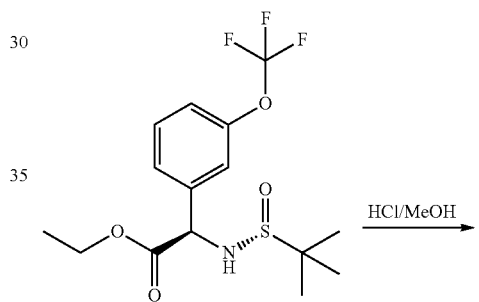

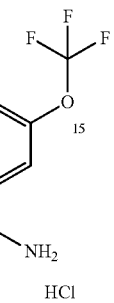

To a solution of ethyl (2R)-2-[[(R)-tert-butylsulfinyl]amino]-2-[3-(trifluoromethoxy)phenyl]acetate (9.8 g, 26.7 mmol) in MeOH (100 mL), was added HCl/MeOH (4 M, 100 mL) and this mixture was stirred at 25° C. for 2 hours, and then concentrated to afford ethyl (2R)-2-amino-2-[3-(trifluoromethoxy)phenyl]acetate (7.8 g, crude).

Step 4: Preparation of ethyl (R)-2-((tert-butoxycarbonyl)amino)-2-(3-(difluoromethoxy)phenyl)acetate

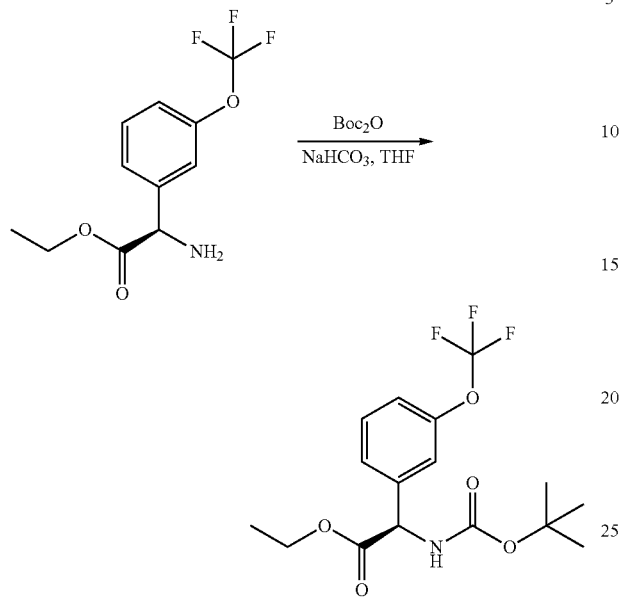

To a mixture of ethyl (2R)-2-amino-2-[3-(trifluoromethoxy)phenyl] acetate hydrochloride (6 g) in THF (150 mL), and Boc$_2$O (8.7 g), NaHCO$_3$ (1.7 g) was added and stirred at 25° C. for 16 hours. The mixture was concentrated and purified by chromatography on silica (petroleum ether: ethyl acetate=10:1) to afford the product (7.2 g).

Step 5: Preparation of tert-butyl (R)-(1-(3-(difluoromethoxy)phenyl)-2-hydroxyethyl)carbamate

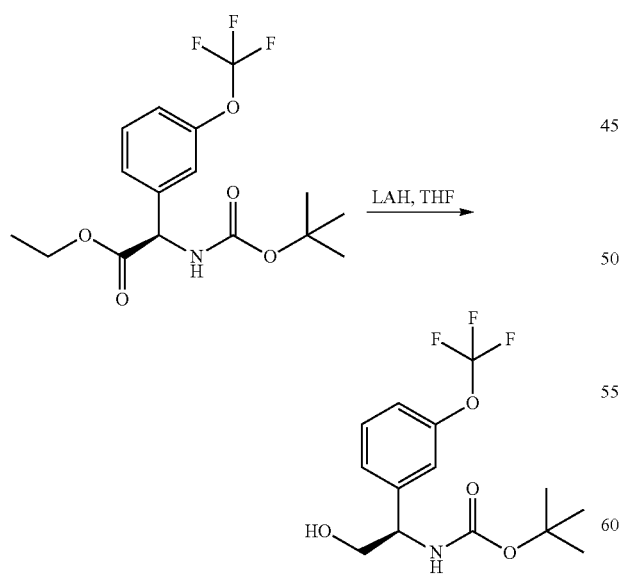

To a suspension of LiAlH$_4$ (1.7 g) in THF (200 mL) was added ethyl (R)-2-((tert-butoxycarbonyl)amino)-2-(3-(difluoromethoxy)phenyl)acetate (4 g) in THF (25 mL), with ice-cooling. The reaction was allowed to warm to 25° C. and was stirred for 2 hours. Anhydrous magnesium sulfate was added and then one drop of water and ethyl acetate were successively added. Insoluble substances were filtered off through a pad of celite. The filtrate was concentrated and purified by chromatography on silica (petroleum ether:ethyl acetate=5:1) (2.1 g).

Step 6: Preparation of tert-butyl (R)-(2-(difluoromethoxy)-1-(3-(trifluoromethoxy)phenyl)ethyl)carbamate

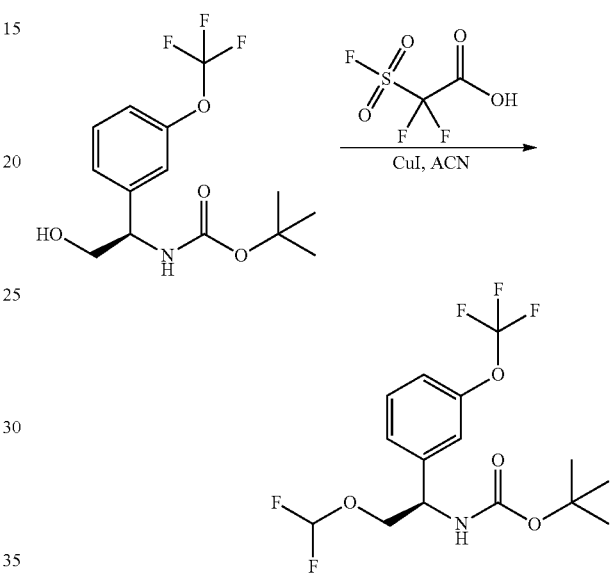

To a solution of tert-butyl (R)-(1-(3-(difluoromethoxy)phenyl)-2-hydroxyethyl)carbamate (1.5 g) in MeCN (20 mL), CuI (360 mg) was added and stirred at 25° C. under N$_2$ atmosphere for 30 minutes. A solution of 2,2-difluoro-2-fluorosulfonyl-acetic acid (1.7 g) in MeCN (5 mL) was added at 45° C. over 30 minutes, and the reaction was stirred at 45° C. for 1 hour. The mixture was concentrated and then diluted by ethyl acetate (100 mL), filtered and concentrated to afford the desired product (1.5 g, crude).

Step 7: Preparation of (R)-2-(difluoromethoxy)-1-(3-(trifluoromethoxy)phenyl)ethan-1-amine

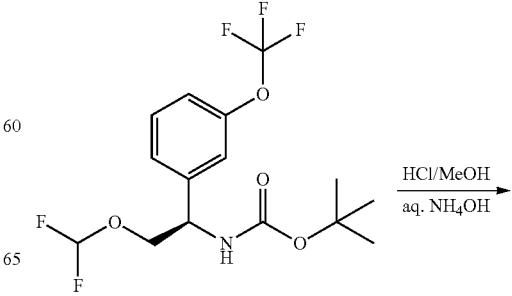

-continued

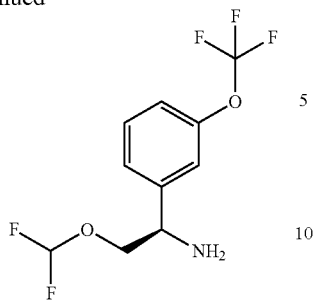

To a solution of tert-butyl (R)-(2-(difluoromethoxy)-1-(3-(trifluoromethoxy)phenyl)ethyl)carbamate (1.5 g) in MeOH (15 mL), was added HCl/MeOH (4M in MeOH, 30 mL) at 25° C., and the reaction was stirred at 25° C. for 30 minutes. Ammonium hydroxide (30%) was added to pH=9, the solution was concentrated and purified by chromatography on silica (petroleum ether:ethyl acetate=2:1) to afford (R)-2-(difluoromethoxy)-1-(3-(trifluoromethoxy)phenyl)ethan-1-amine (700 mg).

IIa: (R)-2-(difluoromethoxy)-1-(3-(difluoromethoxy)phenyl) ethan-1-amine hydrochloride

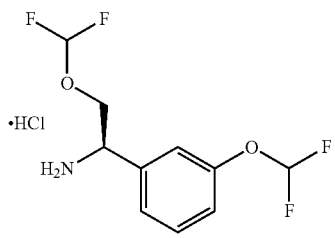 [SMILES: Cl ; N[C@@H](COC(F)F)c1cccc(OC(F)F)c1]

Prepared as described for IIb using appropriate reagents

IIc: (R)-2-cyclopropoxy-1-(3-(difluoromethoxy)phenyl)ethan-1-amine hydrochloride

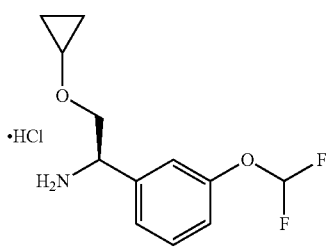 [SMILES: Cl ; N[C@@H](COC1CC1)c1cccc(OC(F)F)c1]

Step 1: Preparation of
4-methyl-N'-(p-tolylsulfonyl)benzene sulfonohydrazide

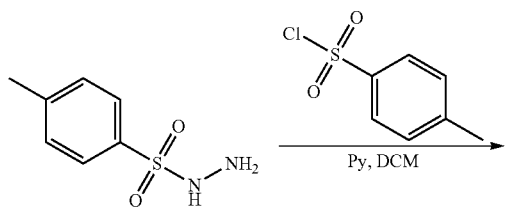

-continued

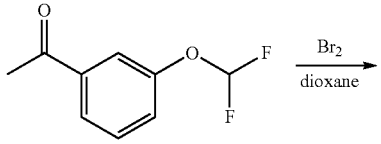

To a mixture of 4-methylbenzenesulfonohydrazide (70 g) and 4-methylbenzenesulfonyl chloride (93 g) was added DCM (400 mL). The mixture was cooled to 0° C. and pyridine (38.65 g) was added dropwise, and the reaction mixture was stirred at 0° C. for 1 hour and 20° C. for 7 hours. The mixture was added water (200 mL) and methyl-tert-butyl ether (METB) (200 mL) and filtered. The filter cake was washed with METB (200 mL) and dried to give 4-methyl-N'-(p-tolylsulfonyl)benzenesulfonohydrazide (125 g).

1H NMR (DMSO-d6 400 MHz): δ 9.55 (s, 2H), 7.61 (d, 4H), 7.35 (d, 4H), 2.36 (s, 6H).

Step 2: Preparation of
2-bromo-1-(3-(difluoromethoxy)phenyl)ethan-1-one

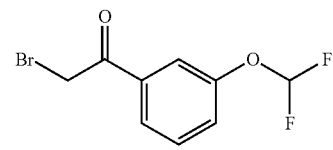

To a solution of 1-[3-(difluoromethoxy)phenyl]ethanone (10 g) in dioxane (100 mL) was added a solution of Br₂ (8.58 g) in dioxane (100 mL). The resulting mixture was stirred at 20° C. for 2 hours. Sat.aq.NaHCO₃ solution (50 mL) and H₂O (100 mL) was added, and the aqueous phase was extracted with EtOAc (200 mL×2). The organic phase was washed with brine (200 mL), dried over Na₂SO₄ and concentrated to give 2-bromo-1-[3-(difluoromethoxy)phenyl]ethanone (17 g).

1H NMR (CDCl3 400 MHz): δ 7.81 (d, 1H), 7.72 (s, 1H), 7.49 (t, 1H), 7.37 (d, 1H), 6.56 (t, 1H), 4.41 (s, 2H).

Step 3: Preparation of
1-(3-(difluoromethoxy)phenyl)-2-iminoethan-1-one

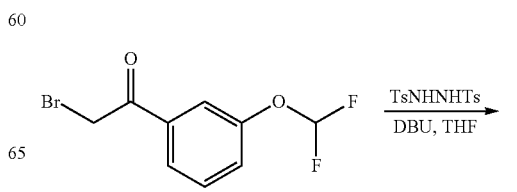

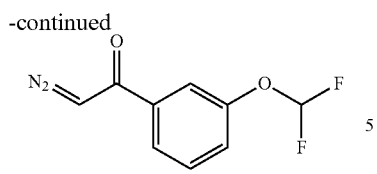

To a solution of 2-bromo-1-[3-(difluoromethoxy)phenyl]ethanone (5.6 g) and 4-methyl-N'-(p-tolylsulfonyl)benzenesulfonohydrazide (11.51 g) in THF (100 mL). DBU (12.87 g) Was added dropwise at 0° C. The reaction mixture was stirred at 0° C. for 1 hour and 20° C. for 4 hours. The mixture was quenched by sat. aq. NaHCO₃ (200 mL) and diluted with water (200 mL), then extracted with EtOAc (200 mL×2). The organic layer was washed with brine (100 mL), dried over Na₂SO₄ and concentrated. The crude was purified by column chromatograph on silica gel (20% EtOAc in Petroleum ether) to give 1-(3-(difluoromethoxy)phenyl)-2-iminoethan-1-one (6.4 g).

1H NMR (CDCl₃, 400 MHz): δ 7.57 (dt, 1H), 7.55 (s, 1H), 7.46 (t, 1H), 7.31 (dd, 1H), 6.56 (t, 1H), 5.90 (s, 1H).

Step 4: Preparation of 2-cyclopropoxy-1-(3-(difluoromethoxy)phenyl)ethan-1-one

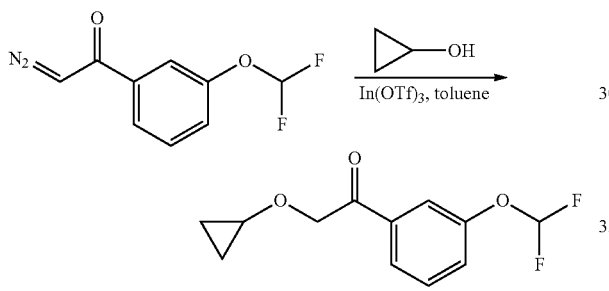

To a solution of cyclopropanol (1.75 g) and 2-diazo-1-[3-(difluoromethoxy) phenyl]ethanone (3.2 g) in toluene (50 mL) was added indium(III) triflate (1.7 g) under N₂. The resulting mixture was stirred at 20° C. for 16 hours. The mixture was quenched by sat.aq.NaHCO₃ (100 mL) and diluted with H₂O (50 mL), and then extracted with EtOAc (100 mL×2). The organic layer was washed with brine (200 mL×2), dried over Na₂SO₄ and concentrated. The crude was purified by column chromatograph on silica gel (5% EtOAc in Petroleum ether) to give 2-cyclopropoxy-1-(3-(difluoromethoxy)phenyl)ethan-1-one (6.1 g).

1H NMR (CDCl₃, 400 MHz): δ 7.76 (d, 1H), 7.68 (s, 1H), 7.47 (t, 1H), 7.34 (d, 1H), 6.55 (t, 1H), 4.74 (s, 1H), 3.55-3.50 (m, 1H), 0.70-0.66 (m, 2H), 0.53-0.49 (m, 2H).

Step 5: Preparation of (R,Z)—N-(2-cyclopropoxy-1-(3-(difluoromethoxy)phenyl)ethylidene)-2-methylpropane-2-sulfinamide

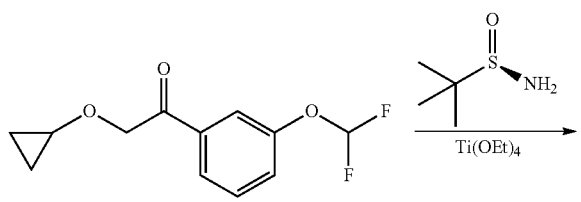

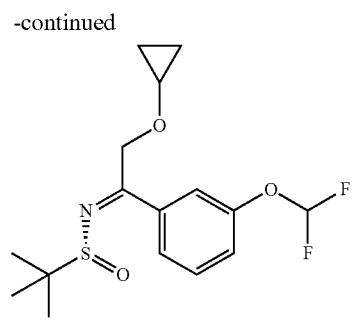

To a solution of 2-(cyclopropoxy)-1-[3-(difluoromethoxy)phenyl]ethanone (6.1 g) and (R)-2-methylpropane-2-sulfinamide (4.6 g) in THF (100 mL) was added Ti(OEt)₄ (11.5 g). The resulting mixture was stirred at 60° C. for 8 hours and then used directly in the next step.

Step 6: Preparation of (R)—N—((R)-2-cyclopropoxy-1-(3-(difluoromethoxy)phenyl)ethyl)-2-methylpropane-2-sulfinamide

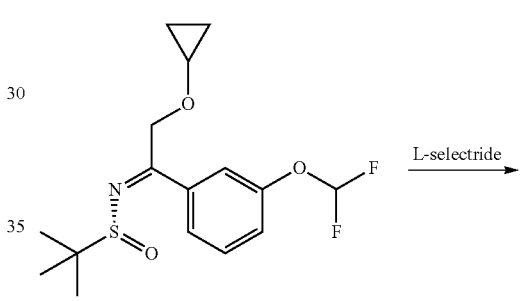

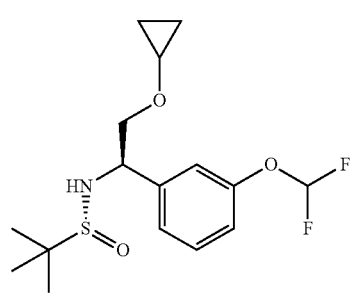

To the solution of (R,Z)—N— (2-cyclopropoxy-1-(3-(difluoromethoxy)phenyl)ethylidene)-2-methylpropane-2-sulfinamide in THF (150 mL) from the previous step, was added a solution of L-selectride (1 M in THF, 50.36 mL) dropwise at −45° C. The mixture was stirred at −45° C. for 1 hour, and was quenched by MeOH (100 mL) and H₂O (100 mL), and filtered on celite. The filtrate was extracted with EtOAc (200 mL×2), the organic layer was washed with brine (200 mL×2), dried over Na₂SO₄ and concentrated. The crude was purified by column chromatograph on silica gel (3050% EtOAc in Petroleum ether) to give (R)—N—((R)-2-cyclopropoxy-1-(3-(difluoromethoxy)phenyl)ethyl)-2-methylpropane-2-sulfinamide (2.4 g).

Step 7: Preparation of (R)-2-cyclopropoxy-1-(3-(difluoromethoxy)phenyl)ethan-1-amine hydrochloride

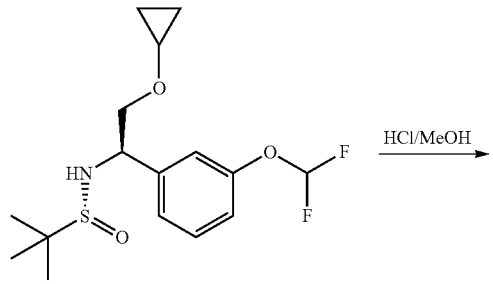

To a solution of (R)—N—((R)-2-cyclopropoxy-1-(3-(difluoromethoxy)phenyl)ethyl)-2-methylpropane-2-sulfinamide (0.46 g) in MeOH (10 mL) was added HCl/MeOH (10 mL). The resulting mixture was stirred at 20° C. for 1 hour and concentrated to give (1R)-2-(cyclopropoxy)-1-[3-(difluoromethoxy)phenyl]ethanamine hydrochloride (0.46 g, crude)

IId: (R)-2-cyclopropoxy-1-(3-(trifluoromethoxy)phenyl)ethan-1-amine hydrochloride

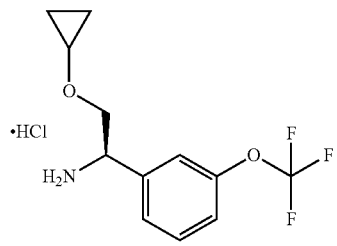 [SMILES: Cl ; N[C@@H](COC1CC1)c1cccc(OC(F)(F)F)c1]

Prepared as described for IIc using 1-[3-(trifluoromethoxy)phenyl]ethanone as starting material.

IIe: (R)-1-(3-(difluoromethoxy)phenyl)-2-(trifluoromethoxy)ethan-1-amine hydrochloride

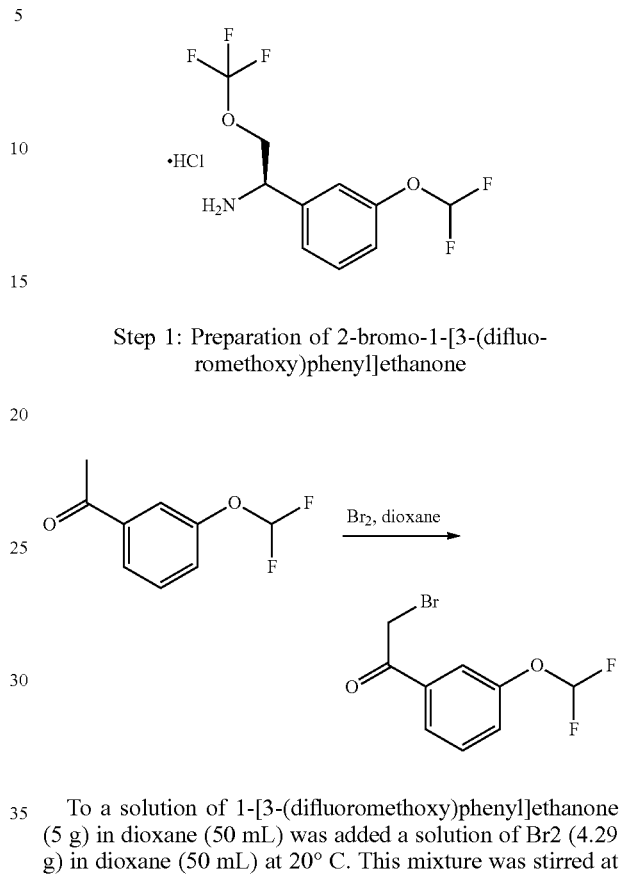

Step 1: Preparation of 2-bromo-1-[3-(difluoromethoxy)phenyl]ethanone

To a solution of 1-[3-(difluoromethoxy)phenyl]ethanone (5 g) in dioxane (50 mL) was added a solution of Br2 (4.29 g) in dioxane (50 mL) at 20° C. This mixture was stirred at 20° C. for 1 hour, then diluted by EtOAc (200 mL) and washed by water (100 mL×3). The organic phase was dried over anhydrous Na$_2$SO$_4$ and concentrated. The residue was purified by column of chromatography on silica gel (Petroleum ether:EtOAc=10:1) to afford 2-bromo-1-[3-(difluoromethoxy)phenyl]ethanone (5 g).

Step 2: Preparation of 1-(3-(difluoromethoxy)phenyl)-2-(trifluoromethoxy)ethan-1-one

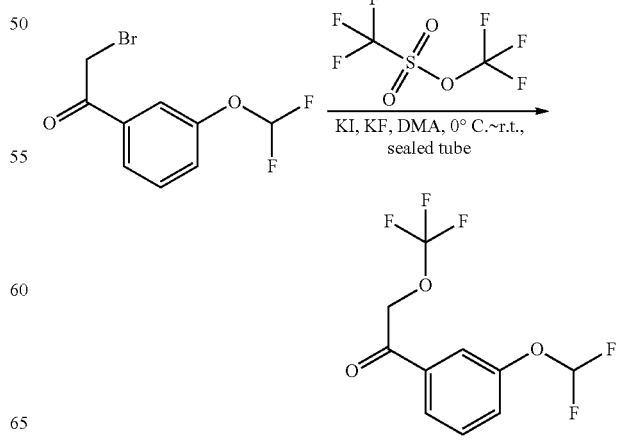

To a solution of KF (712 mg) in DMA (20 mL) was added trifluoromethyl trifluoromethanesulfonate (4.11 g) at 0° C. The reaction mixture was stirred in a sealed tube for 1 hour, then 2-bromo-1-[3-(difluoromethoxy)phenyl]ethanone (2.5 g, 9.43 mmol) and KI (157 mg) were added to this solution at 0° C. and was taken to 20° C. and stirred for 16 hours. The mixture was diluted with EtAOc (100 mL) and washed with water (50 mL×3). The organic phase was concentrated to yield the product, which was purified by acidic preparative HPLC (1.4 g).

1H NMR (CDCl₃ 400 MHz): δ 7.72 (d, 1H), 7.66 (s, 1H), 7.51 (t, 1H), 7.40 (d, 1H), 6.56 (t1H), 5.13 (s, 2H). 19F NMR (CDCl₃ 400 MHz): 5−61.11, −81.52, −81.71.

Step 3: Preparation of (R)—N— (1-(3-(difluoromethoxy)phenyl)-2-(trifluoromethoxy)ethylidene)-2-methylpropane-2-sulfinamide

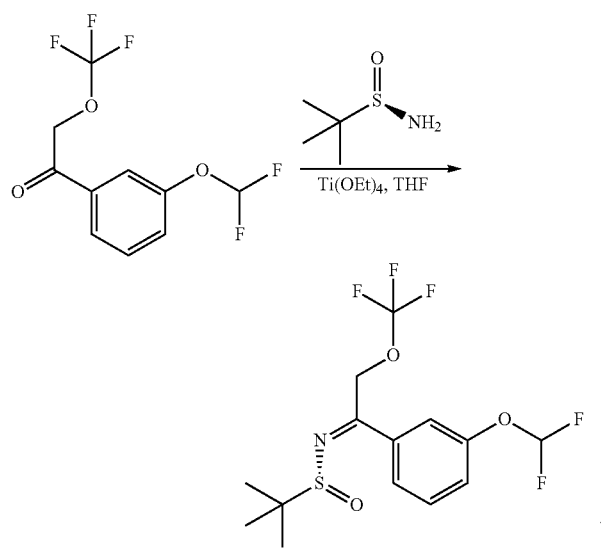

A mixture of 1-(3-(difluoromethoxy)phenyl)-2-(trifluoromethoxy)ethan-1-one (900 mg), (R)-2-methylpropane-2-sulfinamide (606 mg) and Ti(OEt)₄ (2.28 g) in THF (50 mL) was stirred at 60° C. under N₂ for 16 hours. The product (1.2 g, crude) in THF (70 mL) was obtained and used directly in the next step.

Step 4: Preparation of (R)—N—((R)-1-(3-(difluoromethoxy)phenyl)-2-(trifluoromethoxy)ethyl)-2-methylpropane-2-sulfinamide

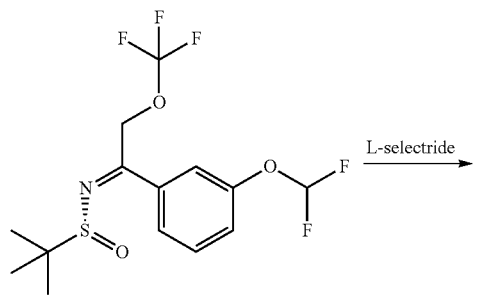

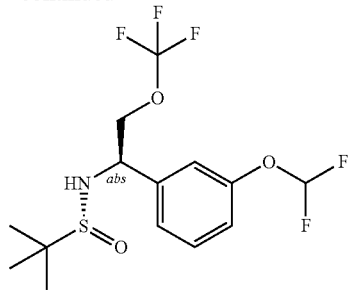

To a solution of (R)—N-(1-(3-(difluoromethoxy) phenyl)-2-(trifluoromethoxy) ethylidene)-2-methylpropane-2-sulfinamide (1.2 g) in THF (70 mL) was added L-selectride (1 M in THF, 3.86 mL) at −60° C. The mixture was stirred at −60° C. for 0.5 hour and then diluted with EtOAc (100 mL) and washed with water (50 mL×3). The organic phase was dried, filtered and concentrated. The crude product was purified by chromatography on silica gel (Petroleum ether/Ethyl acetate=5:1) to afford (R)—N—((R)-1-(3-(difluoromethoxy) phenyl)-2-(trifluoromethoxy)ethyl)-2-methylpropane-2-sulfinamide (600 mg).

1H NMR (CDCl₃ 400 MHz): δ 7.37 (t, 1H), 7.20 (d, 1H), 7.12-7.09 (m, 2H), 6.50 (t, 1H), 4.75-4.72 (m, 1H), 4.20-4.16 (m, 1H), 4.14-4.05 (m, 1H), 3.87 (s, 1H), 1.21 (s, 9H).

Step 5: Preparation of (R)-1-(3-(difluoromethoxy) phenyl)-2-(trifluoromethoxy)ethan-1-amine hydrochloride

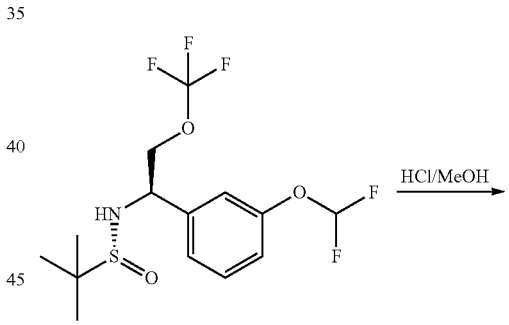

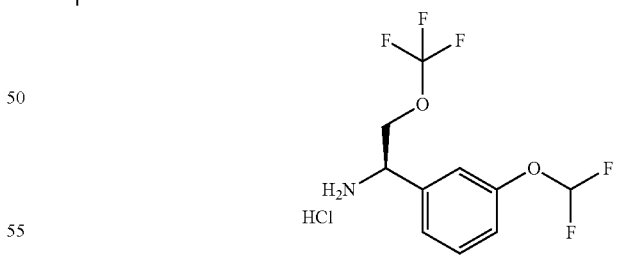

To a solution of (R)—N—((R)-1-(3-(difluoromethoxy) phenyl)-2-(trifluoromethoxy)ethyl)-2-methylpropane-2-sulfinamide (600 mg) in MeOH (10 mL) was added HCl/MeOH (4 M in MeOH, 8.0 mL). This mixture was stirred at 15° C. for 1 hour, and then concentrated to afford ((R)-1-(3-(difluoromethoxy)phenyl)-2-(trifluoromethoxy)ethan-1-amine hydrochloride (500 mg, crude.

¹H NMR (CDCl₃ 400 MHz): δ 9.17 (s, 3H), 7.40-7.31 (m, 4H), 6.55 (t, 1H), 4.58 (s, 1H), 4.46-4.42 (m, 1H), 4.33-4.29 (m, 1H).

IIf: (R)-2-(trifluoromethoxy)-1-(3-(trifluoromethoxy)phenyl)ethan-1-amine hydrochloride

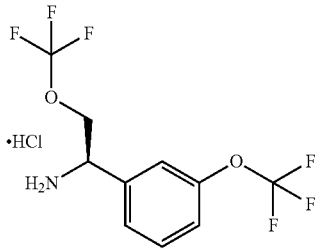 [SMILES: Cl ; N[C@@H](COC(F)(F)F)c1cccc(OC(F)(F)F)c1]

Prepared as described for IIe using 1-[3-(trifluoromethoxy)phenyl]ethanone as starting material.

$^1$H NMR (CDCl$_3$ 400 MHz): δ 9.18 (s, 3H), 7.19-7.47 (m, 1H), 7.19-7.38 (m, 2H), 7.27 (s, 1H), 4.65 (s, 1H), 4.47-4.42 (m, 1H), 4.32-4.30 (m, 1H).

IIg: (S)-1-(3-(difluoromethoxy)phenyl)butan-1-amine hydrochloride

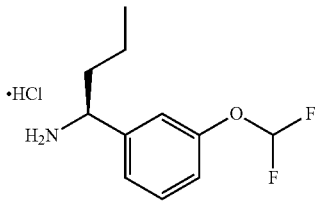

Step 1: Preparation of (R)—N-(3-(difluoromethoxy)benzylidene)-2-methylpropane-2-sulfinamide

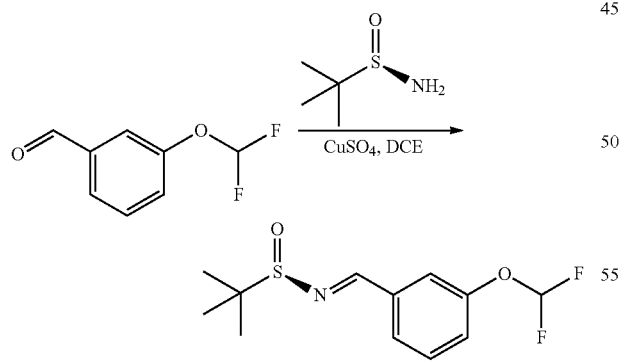

To a solution of 3-(difluoromethoxy)benzaldehyde (3 g) and (R)-2-methylpropane-2-sulfinamide (2.54 g) in DCE (120 mL) was added CuSO$_4$ (13.91 g). The mixture was stirred at 55° C. for 16 hours. The reaction mixture was filtered, and the filtrate was concentrated. The residue was purified by column chromatography (SiO$_2$, Petroleum ether/Ethyl acetate=100/1 to 10:1) to afford the product (3 g).

Step 2: Preparation of (R)—N—((S)-1-(3-(difluoromethoxy)phenyl)but-3-en-1-yl)-2-methylpropane-2-sulfinamide

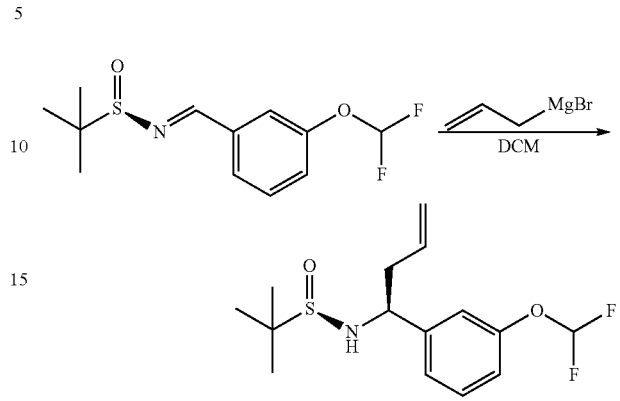

To a solution of (R)—N-(3-(difluoromethoxy)benzylidene)-2-methylpropane-2-sulfinamide (1 g) in DCM (40 mL) was slowly added allyl(bromo)magnesium (1M solution in THF, 10.9 mL) in THF at 0° C. The resulting mixture was stirred at 0° C. for 1 hour and 25° C. for 2 hours. The reaction mixture was quenched by addition saturated NH$_4$Cl (10 mL) at 0° C., then diluted with H$_2$O (50 mL) and extracted with DCM (40 mL×3). The combined organic phases were washed with H$_2$O (40 mL), dried over Na$_2$SO$_4$, filtered and concentrated. The residue was purified by column chromatography (SiO$_2$, Petroleum ether/Ethyl acetate=100/1 to 1:2) to afford (R)—N—((S)-1-(3-(difluoromethoxy)phenyl)but-3-en-1-yl)-2-methylpropane-2-sulfinamide (580 mg).

$^1$H NMR (CDCl$_3$ 400 MHz): δ 7.31 (t, 1H), 7.15 (d, 1H), 7.08 (s, 1H), 7.01 (d, 1H), 6.48 (t, 1H), 5.73-5.66 (m, 1H), 5.19-5.15 (m, 2H), 4.46 (t, 1H), 3.65 (s, 1H), 2.59-2.54 (m, 1H), 2.46-2.38 (m, 1H), 1.19 (s, 9H).

Step 3: Preparation of (R)—N—((S)-1-(3-(difluoromethoxy)phenyl)butyl)-2-methylpropane-2-sulfinamide

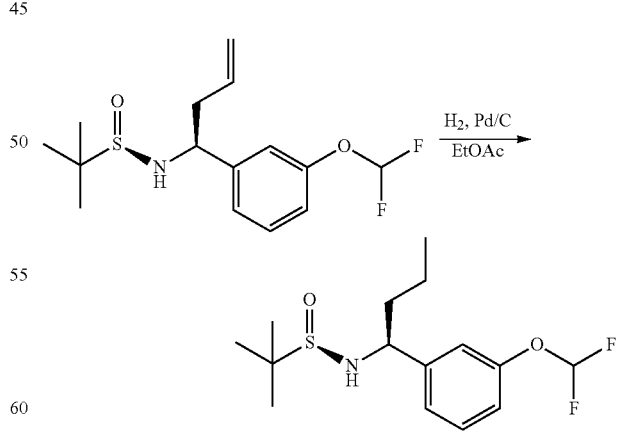

To a solution of (R)—N—((S)-1-(3-(difluoromethoxy)phenyl)but-3-en-1-yl)-2-methylpropane-2-sulfinamide (580 mg) in EtOAc (20 mL) was added Pd/C (0.4 g, 10% purity) under N$_2$. The suspension was degassed under vacuum and purged with H$_2$ several times. The mixture was stirred under H₂ (18 psi) at 25° C. for 0.5 hour. The reaction mixture was filtered and concentrated to afford (R)—N—((S)-1-(3-(difluoromethoxy)phenyl)butyl)-2-methylpropane-2-sulfinamide (560 mg).

Step 4: Preparation of (S)-1-(3-(difluoromethoxy)phenyl)butan-1-amine hydrochloride

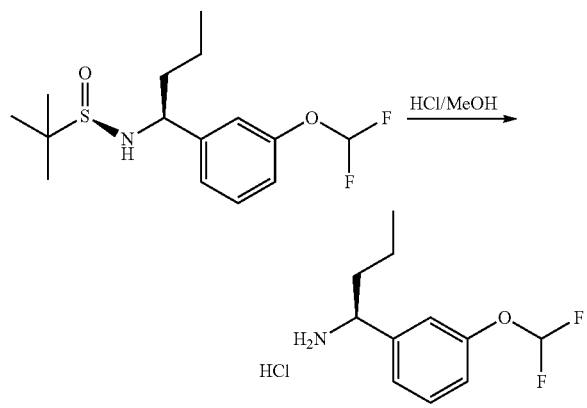

To a solution of (R)—N—((S)-1-(3-(difluoromethoxy)phenyl)butyl)-2-methylpropane-2-sulfinamide (580 mg) in MeOH (8 mL) was added HCl/MeOH (4 M, 3.1 mL). The mixture was stirred at 25° C. for 3 hours and then concentrated to afford (1S)-1-[3-(difluoromethoxy) phenyl] butan-1-amine hydrochloride (250 mg).

IIh: (S)-1-(3-(difluoromethoxy)phenyl)-4,4-difluorobutan-1-amine hydrochloride

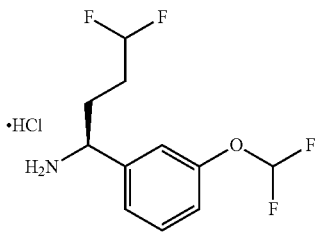 [SMILES: Cl ; N[C@@H](CCC(F)F)c1cccc(OC(F)F)c1]

Step 1: Preparation of 1-(difluoromethoxy)-3-vinyl-benzen

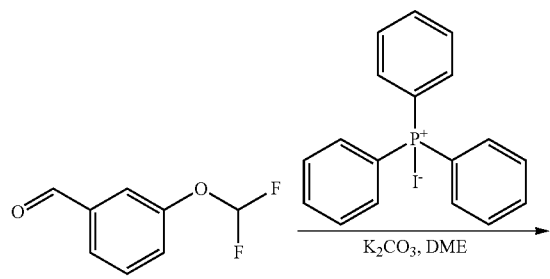

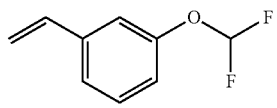

To a solution of methyl triphenylphosphonium iodide (7.05 g) in DME (50 mL) was added K₂CO₃ (2.41 g). The resulting mixture was stirred at 20° C. for 1 hour, then 3-(difluoromethoxy)benzaldehyde (1.5 g) was added and stirred continued at 80° C. for 15 hours. The mixture was filtered, and filtercake was washed with petroleum ether (100 mL). The filtrate was concentrated and purified by column chromatography (SiO₂, Petroleum ether/Ethyl acetate=1/0 to 10/1) to afford 1-(difluoromethoxy)-3-vinyl-benzene (1.4 g)

¹H NMR (CDCl₃ 400 MHz): δ 7.32 (t, 1H), 7.25 (d, 1H), 7.16 (s, 1H), 7.01 (d, 1H), 6.70 (t, 1H), 6.52 (t, 1H), 5.77 (d, 1H), 5.32 (d, 1H).

Step 2: Preparation of 1-(3-(difluoromethoxy)phenyl)-4,4-difluorobutan-1-one

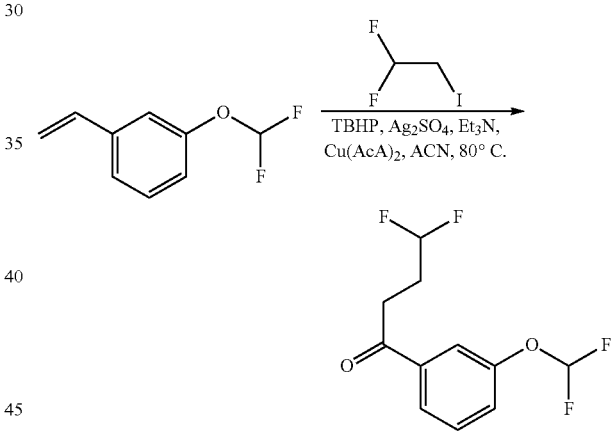

To a solution 1,1-difluoro-2-iodo-ethane (1 g), 1-(difluoromethoxy)-3-vinyl-benzene (1.33 g), bis[(Z)-1-methyl-3-oxo-but-1-enoxy]copper (273 mg) and Ag₂SO₄ (325 mg) in ACN (20 mL) was added Et₃N (527 mg) and tert-butyl hydroperoxide (TBHP) (2.01 g, 70% in water). The resulting mixture was stirred at 80° C. for 24 hours. The reaction was quenched with saturated aq. Na₂S₂O₃ and extracted with DCM (10 mL×3). The organic phases were combined, washed with brine (5 mL×2), dried over Na₂SO₄ and concentrated. The residue was purified by column chromatography (SiO₂, Petroleum ether/Ethyl acetate=I/O to 5/1) to afford 1-(3-(difluoromethoxy)phenyl)-4,4-difluorobutan-1-one (300 mg).

¹H NMR (CDCl₃ 400 MHz): δ 7.82 (d, 1H), 7.73 (s, 1H), 7.50 (t, 1H), 7.36 (d, 1H), 6.57 (t, 1H), 6.02 (tt, 1H), 3.18 (t, 2H), 2.35-2.27 (m, 2H).

Step 3: Preparation of (S,E)-N-(1-(3-(difluoromethoxy)phenyl)-4,4-difluorobutylidene)-2-methylpropane-2-sulfinamide

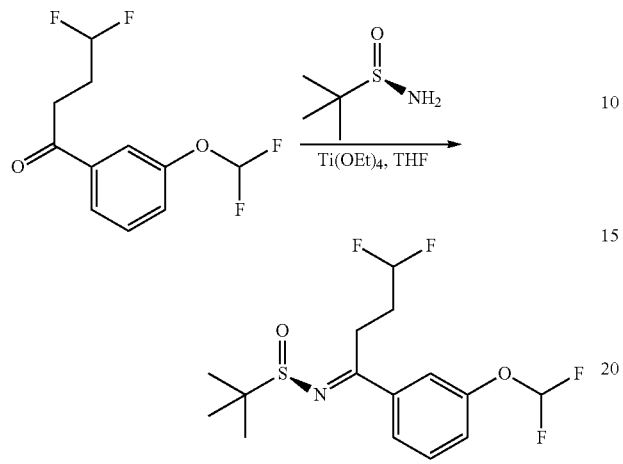

To a solution of 1-(3-(difluoromethoxy)phenyl)-4,4-difluorobutan-1-one (300 mg) and (R)-2-methylpropane-2-sulfinamide (218 mg) in THF (10 mL) was added Ti(OEt)$_4$ (547 mg). The mixture was stirred at 60° C. for 6 hours. The reaction mixture was used directly in the next step.

Step 4: Preparation of N-[(1S)-1-[3-(difluoromethoxy)phenyl]-4,4-difluoro-butyl]-2-methyl-propane-2-sulfinamide

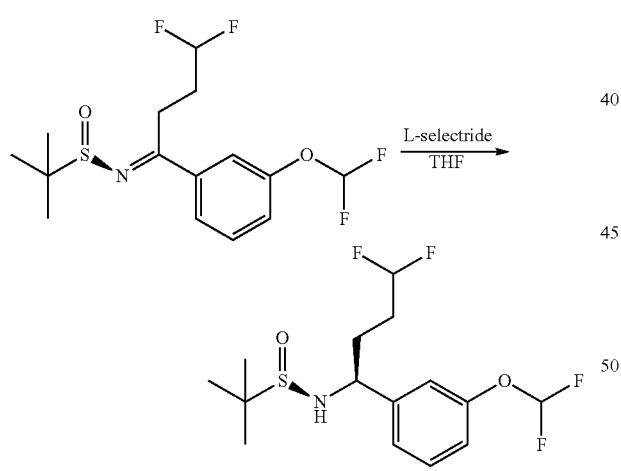

L-selectride (1 M in THF, 3.59 mL) was added to a solution of (S)—N-(1-(3-(difluoromethoxy) phenyl)-4,4-difluorobutylidene)-2-methylpropane-2-sulfinamide (423 mg) in THF at −48° C. The reaction mixture was stirred for 0.5 hour, then it was taken to 0° C. and H$_2$O (~10 mL) was added. The resulting mixture was extracted with EtOAc (35 mL×2). The organic extracts were washed with brine (10 mL), dried over Na$_2$SO$_4$ and concentrated. The residue was purified by column chromatography (SiO$_2$, Petroleum ether/Ethyl acetate=I/O to 1/1) to afford N-[(1S)-1-[3-(difluoromethoxy)phenyl]-4,4-difluoro-butyl]-2-methyl-propane-2-sulfinamide (140 mg)

Step 5: (S)-1-(3-(difluoromethoxy)phenyl)-4,4-difluorobutan-1-amine hydrochloride

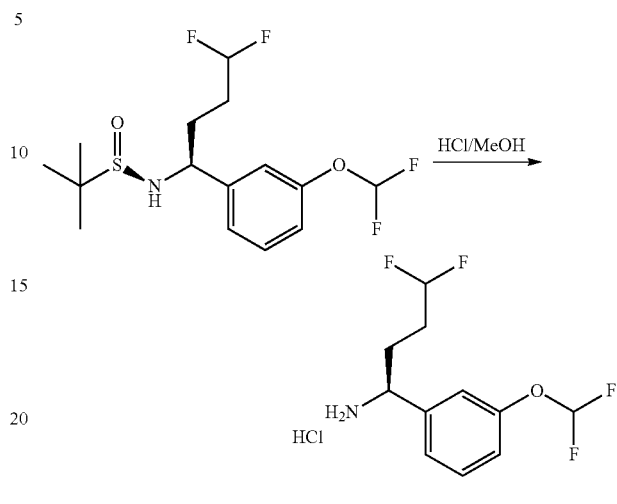

N-[(1S)-1-[3-(difluoromethoxy)phenyl]-4,4-difluorobutyl]-2-methyl-propane-2-sulfinamide (140 mg) in MeOH (10 mL) and HCl/MeOH (5 mL, 4M) was stirred at 20° C. for 1 hour. The mixture was concentrated to afford (S)-1-(3-(difluoromethoxy)phenyl)-4,4-difluorobutan-1-amine hydrochloride (110 mg)

IIi: (S)-1-(3-(difluoromethoxy)phenyl)-3,3-difluoropropan-1-amine hydrochloride

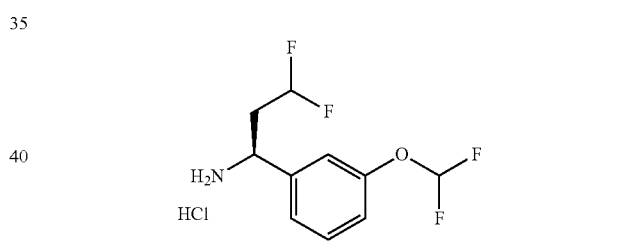

Step 1: Preparation of (S,E)-N-(3-(difluoromethoxy)benzylidene)-2-methylpropane-2-sulfinamide

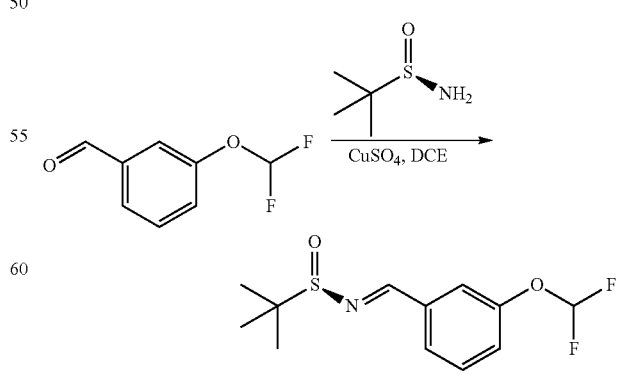

To a solution of 3-(difluoromethoxy)benzaldehyde (5 g) and (R)-2-methylpropane-2-sulfinamide (4.22 g) in DCE (150 mL) was added CuSO$_4$ (23 g). The reaction mixture was stirred at 55° C. for 20 hours, and then filtered and concentrated. The crude product was purified by chromatography on silica (SiO$_2$, Petroleum ether/Ethyl acetate=10/1 to 5/1) to afford (S,E)-N-(3-(difluoromethoxy) benzylidene)-2-methylpropane-2-sulfinamide (6.9 g).

$^1$H NMR (CDCl$_3$ 400 MHz): δ 8.55 (s, 1H), 7.65 (d, 1H), 7.62 (s, 1H), 7.47 (t, 1H), 7.25 (d, 1H), 6.55 (t, 1H), 1.25 (s, 9H).

Step 2: Preparation of (S)—N—((S)-1-(3-(difluoromethoxy)phenyl)but-3-en-1-yl)-2-methylpropane-2-sulfinamide

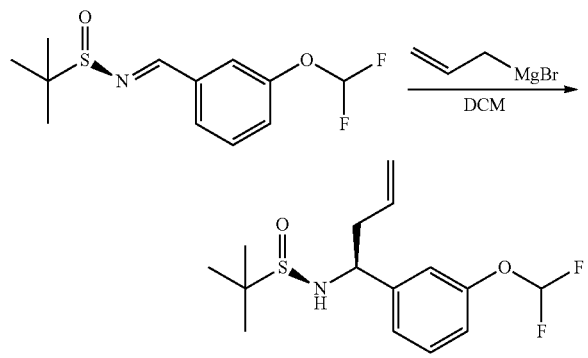

To a solution of (S,E)-N-(3-(difluoromethoxy)benzylidene)-2-methylpropane-2-sulfinamide (2 g) in DCM (60 mL) was slowly added allyl(bromo)magnesium (1 M solution in THF, 21.79 mL) at 0° C. The reaction mixture was stirred at 0° C. for 1 hour and 25° C. for 2 hours. The reaction was quenched by addition of sat.aq.NH$_4$Cl (10 mL) at 0° C., and then diluted with H$_2$O (50 mL) and extracted with DCM (40 mL×3). The combined organic phases were washed with H$_2$O (40 mL), dried over Na$_2$SO$_4$, filtered and concentrated. The residue was purified by chromatography (SiO$_2$, Petroleum ether/Ethyl acetate=100/1 to 1/2) to afford (S)—N—((S)-1-(3-(difluoromethoxy) phenyl) but-3-en-1-yl)-2-methylpropane-2-sulfinamide (2.3 g).

$^1$H NMR (CDCl$_3$ 400 MHz): δ 7.31 (t, 1H), 7.15 (d, 1H), 7.08 (s, 1H), 7.01 (d, 1H), 6.49 (t, 1H), 5.71-5.65 (m, 1H), 5.19-5.15 (m, 2H), 4.48-4.44 (m, 1H), 3.66 (s, 1H), 2.59-2.54 (m, 1H), 2.46-2.40 (m, 1H), 1.18 (s, 9H).

Step 3: Preparation of (S)—N—((S)-1-(3-(difluoromethoxy)phenyl)-3-oxopropyl)-2-methylpropane-2-sulfinamide

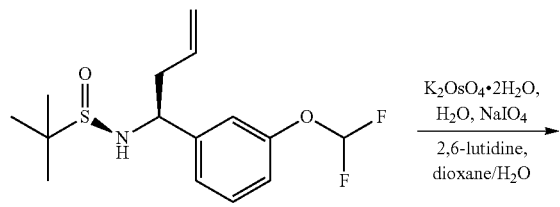

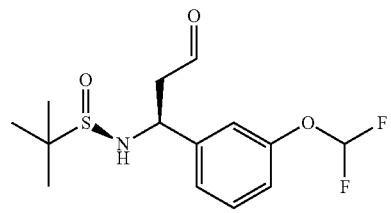

Potassium dioxido(dioxo)osmium hydrate (276 mg) was added in one portion to a stirred solution of S)—N—((S)-1-(3-(difluoromethoxy)phenyl)but-3-en-1-yl)-2-methylpropane-2-sulfinamide (2.5 g), 2,6-lutidine (1.69 g) and sodium periodate (5.05 g) in a mixture of dioxane (10 mL) and H$_2$O (3 mL). The reaction mixture was stirred at 20° C. for 1 hour and then diluted with DCM (100 mL) and water (20 mL). The aqueous layer was extracted with DCM (25 mL×2). The combined organic extracts were dried over Na$_2$SO$_4$. The crude reaction mixture was used directly in the next step.

Step 4: Preparation of (S)—N—((S)-1-(3-(difluoromethoxy)phenyl)-3,3-difluoropropyl)-2-methylpropane-2-sulfinamide

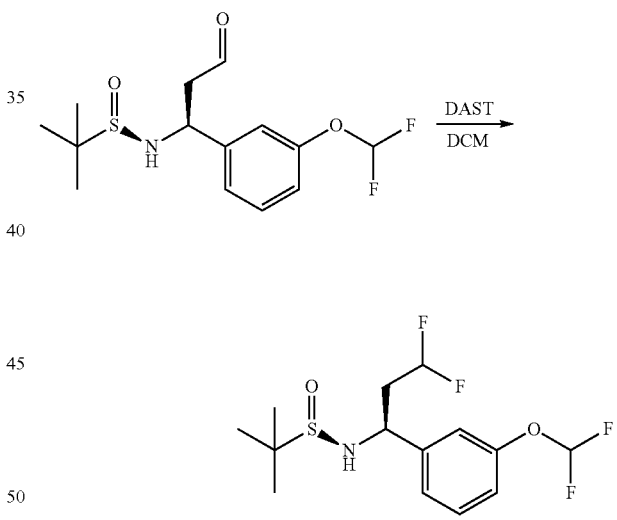

To a solution of (S)—N—((S)-1-(3-(difluoromethoxy) phenyl)-3-oxopropyl)-2-methylpropane-2-sulfinamide (2 g) in DCM (200 mL) was added dropwise diethylaminosulfur trifluoride (DAST) (3.03 g) at −78° C. The reaction mixture was allowed to come to 20° C. and was stirred for 2 hours. The solution was poured into saturated aqueous NaHCO$_3$ (50 mL) and the organic phase was separated. This solution was dried over anhydrous Na$_2$SO$_4$ and concentrated. The residue was purified by column chromatography (SiO2, Petroleum ether/Ethyl acetate=5/1 to 1/1) to afford (S)—N—((S)-1-(3-(difluoromethoxy)phenyl)-3,3-difluoropropyl)-2-methylpropane-2-sulfinamide (500 mg).

Step 5: Preparation of (1S)-1-[3-(difluoromethoxy)phenyl]-3,3-difluoro-propan-1-amine hydrochloride

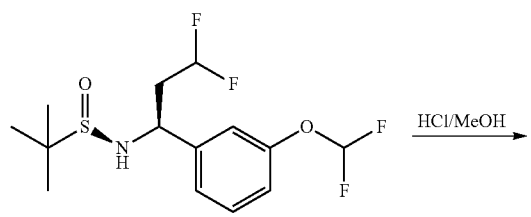

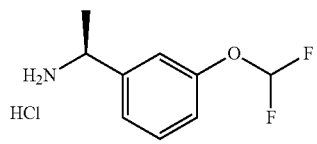

To a solution of (S)—N—((S)-1-(3-(difluoromethoxy)phenyl)-3,3-difluoropropyl)-2-methylpropane-2-sulfinamide (380 mg) in MeOH (15 mL) was added HCl/MeOH (25 mL, 4 M) at 0° C. and the reaction was stirred from for 0.5 hour, and was allowed to come to 25° C. The reaction mixture was concentrated to afford (1S)-1-[3-(difluoromethoxy)phenyl]-3,3-difluoro-propan-1-amine hydrochloride (300 mg, crude, HCl salt). Used directly without further purification.

IIj: (S)-1-(3-(difluoromethoxy)phenyl)ethan-1-amine hydrochloride

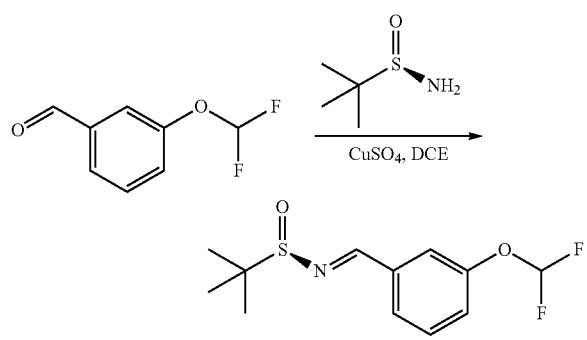

Step 1: Preparation of ((S,E)-N-(3-(difluoromethoxy)benzylidene)-2-methylpropane-2-sulfinamide To a mixture of 3-(difluoromethoxy)benzaldehyde (2 g) and (R)-2-methylpropane-2-sulfinamide (1.7 g) in DCE (60 mL) was added CuSO$_4$ (9.3 g) at 55° C. under N$_2$. The reaction mixture was stirred at 55° C. for 12 hours, filtered and the filtrated was concentrated. The crude product was purified by chromatography on silica gel column (Petroleum ether/Ethyl acetate=20:1-10:1) to give ((S,E)-N-(3-(difluoro-methoxy) benzylidene)-2-methylpropane-2-sulfinamide (4.5 g).

Step 2: Preparation of (S)—N—((S)-1-(3-(difluoromethoxy)phenyl)ethyl)-2-methylpropane-2-sulfinamide

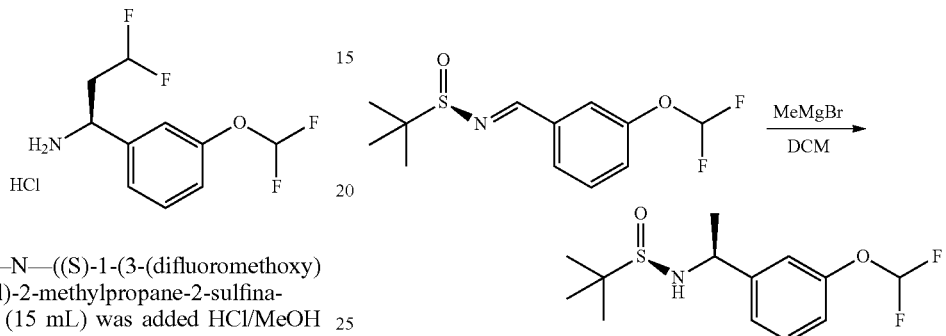

To a solution of ((S,E)-N-(3-(difluoro-methoxy)benzylidene)-2-methylpropane-2-sulfinamide (2 g) in DCM (30 mL) was added bromo (methyl) magnesium (3M in Et$_2$O, 4.8 mL) dropwise at 0° C. The resulting mixture was stirred at 0° C. for 1 hour and 20° C. for 16 hours. The reaction was quenched by aq. sat. NH$_4$Cl (10 mL), and the aqueous phase was extracted with ethyl acetate (30 mL×3). The combined organic extracts were washed with brine (40 mL×2), dried with anhydrous Na$_2$SO$_4$, filtered, concentrated and purified by chromatography on silica gel (Petroleum ether/Ethyl acetate=5:1-1:1) to afford (S)—N—((S)-1-(3-(difluoromethoxy)phenyl)ethyl)-2-methylpropane-2-sulfinamide (960 mg).

Step 3: Preparation of (S)-1-(3-(difluoromethoxy)phenyl)ethan-1-amine hydrochloride

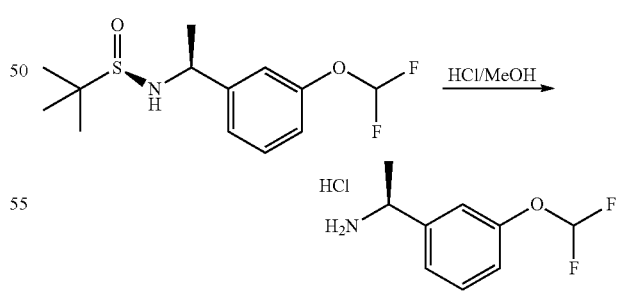

To a solution of (S)—N—((S)-1-(3-(difluoromethoxy)phenyl)ethyl)-2-methylpropane-2-sulfinamide (0.8 g) in MeOH (4 mL) was added HCl/MeOH (4 M, 2 mL). The resulting mixture was stirred at 25° C. for 3 hours, and concentrated to afford (S)-1-(3-(difluoromethoxy) phenyl)ethan-1-amine hydrochloride (1.6 g, crude).

IIk: (R)-2-ethoxy-1-(3-(trifluoromethoxy)phenyl)
ethan-1-amine hydrochloride

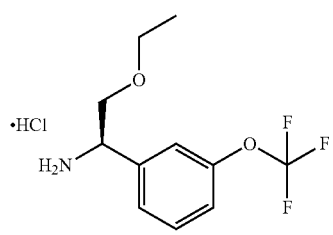 [SMILES: Cl ; CCOC[C@H](N)c1cccc(OC(F)(F)F)c1]

Step 1: Preparation of ethyl
(R,E)-2-((tert-butylsulfinyl)imino)acetate

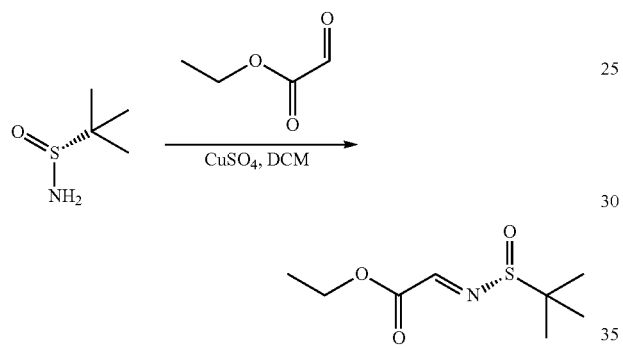

To a solution of ethyl 2-oxoacetate (7.5 g) and (R)-2-methylpropane-2-sulfinamide (4.90 g) in DCM (150 mL) under N₂ was added CuSO₄ (12.9 g) and the reaction mixture was stirred at 25° C. for 24 hours. The solid was filtered off, washed with ethyl acetate (50 mL) and the organic layer was concentrated. The residue was purified by chromatography (SiO₂, hexane/ethyl acetate, 5/1) to yield ethyl (R,E)-2-((tert-butylsulfinyl)imino)acetate (5 g).

Step 2: Preparation of ethyl (R)-2-(((S)-tert-butylsulfinyl)amino)-2-(3-(trifluoromethoxy)phenyl)acetate

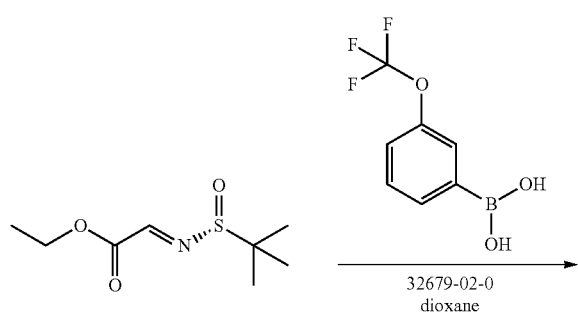

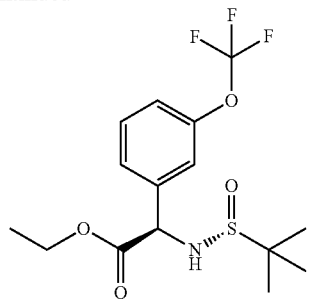

To a solution of ethyl (R,E)-2-((tert-butylsulfinyl)imino)acetate (5 g) and [3-(trifluoromethoxy)phenyl]boronic acid (6.02 g) in dioxane (80 mL) was added bis(acetonitrile)(1,5-cyclooctadiene)rhodium(I)tetrafluoroborate (CAS:32679-02-0) (1.85 g) and this mixture was stirred at 80° C. for 16 hours. The solution was filtered and the organic phase was concentrated. The residue was purified by chromatography (SiO₂, Petroleum Ether:EtOAc=6:1) to afford ethyl (R)-2-(((S)-tert-butylsulfinyl)amino)-2-(3-(trifluoromethoxy)phenyl)acetate (5.1 g).

Step 3: Preparation of ethyl (R)-2-amino-2-(3-(trifluoromethoxy)phenyl)acetate

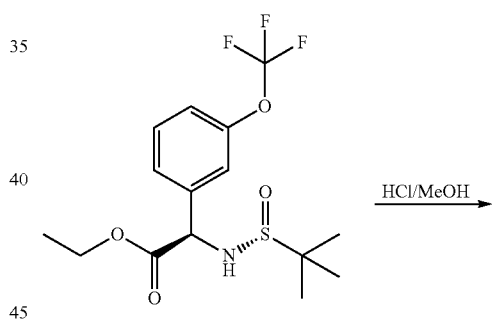

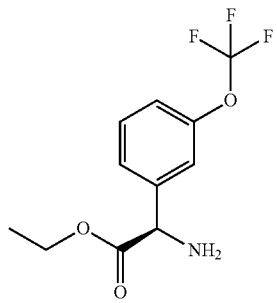

To a solution of ethyl (R)-2-(((S)-tert-butylsulfinyl)amino)-2-(3-(trifluoromethoxy)phenyl)acetate (4.6 g) in MeOH (30 mL) was added HCl/MeOH (4 M, 25.04 mL) at 0° C. The reaction mixture was stirred at 25° C. for 1 hour and concentrated to afford ethyl (R)-2-amino-2-(3-(trifluoromethoxy)phenyl)acetate as a hydrochloride salt (3.3 g).

Step 4: Preparation of ethyl (R)-2-((tert-butoxycarbonyl)amino)-2-(3-(trifluoromethoxy) phenyl)acetate

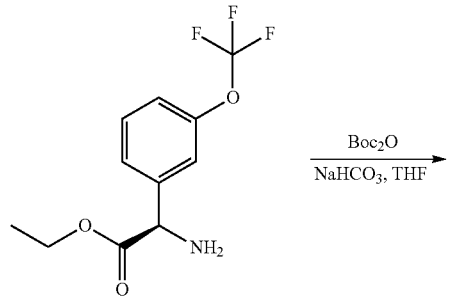

To a mixture of ethyl (R)-2-amino-2-(3-(trifluoromethoxy)phenyl)acetate hydrochloride (3.3 g) in THF (80 mL) was added Boc₂O (4.81 g) and NaHCO₃ (925 mg) and the reaction was stirred at 25° C. for 16 hours.

The reaction mixture was concentrated and diluted with EtOAc (20 mL), washed with water (20 mL) and then concentrated. The residue was purified by chromatography (SiO₂; Petroleum Ether:EtOAc=10:1) to afford ethyl (R)-2-((tert-butoxycarbonyl)amino)-2-(3-(trifluoromethoxy) phenyl)acetate (3.8 g).

Step 5: Preparation of tert-butyl (R)-(2-hydroxy-1-(3-(trifluoromethoxy)phenyl)ethyl)carbamate

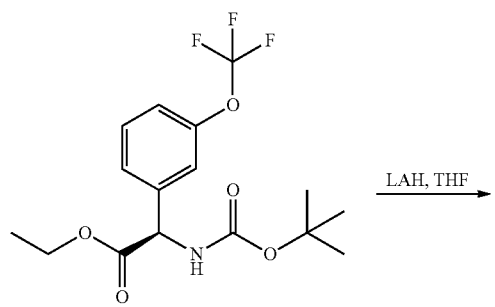

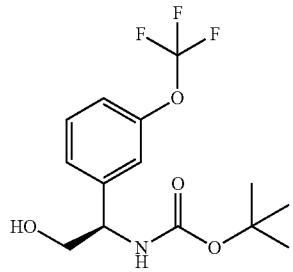

To a suspension of LiAlH₄ (2.1 g) in THF (200 mL) was added ethyl (R)-2-((tert-butoxycarbonyl)amino)-2-(3-(trifluoromethoxy) phenyl)acetate (5 g) in THF (20 mL) under ice-cooling, and the mixture was stirred at 0° C. to 25° C. for 2 hours. Anhydrous magnesium sulfate was added and then water (5 mL) and ethyl acetate (100 mL) were successively added, and the insoluble substances was filtered off using celite. The filtrate was concentrated. The crude product was purified by chromatography (SiO₂, Petroleum Ether: EtOAc=5:1) to afford tert-butyl (R)-(2-hydroxy-1-(3-(trifluoromethoxy)phenyl)ethyl)carbamate (3.37 g).

Step 6: Preparation of tert-butyl (R)-(2-ethoxy-1-(3-(trifluoromethoxy)phenyl)ethyl)carbamate

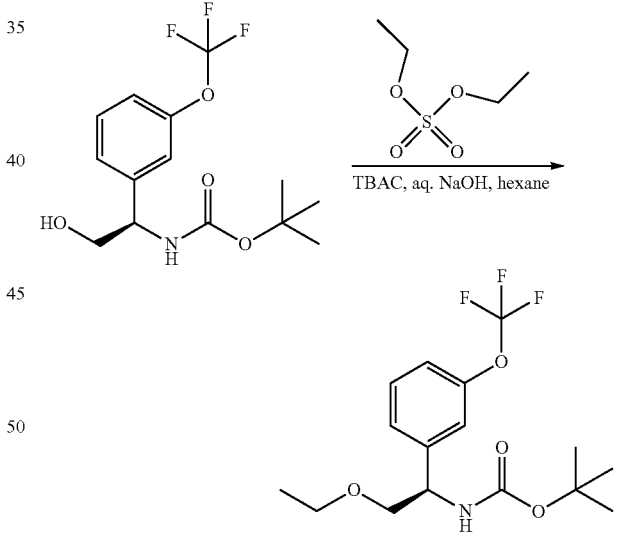

To a solution of tert-butyl (R)-(2-hydroxy-1-(3-(trifluoromethoxy)phenyl)ethyl)carbamate (1 g) in hexane (15 mL) was added diethyl sulfate (960 mg), tetrabutyl ammonium chloride (TBAC) (87 mg) and a solution of NaOH (324 mg) in H₂O (1.5 mL). The resulting mixture was stirred at 25° C. for 20 hours. The reaction mixture was diluted with EtOAc (200 mL), washed with water (100 mL) and brine (100 mL), dried over Na₂SO₄ and concentrated. The crude was purified by chromatography (SiO2, 10% EthylAcetate in Petroleum Ether) to give tert-butyl (R)-(2-ethoxy-1-(3-(trifluoromethoxy)phenyl)ethyl)carbamate (5.9 g).

Step 7: Preparation of (R)-2-ethoxy-1-(3-(trifluoromethoxy)phenyl)ethan-1-amine hydrochloride

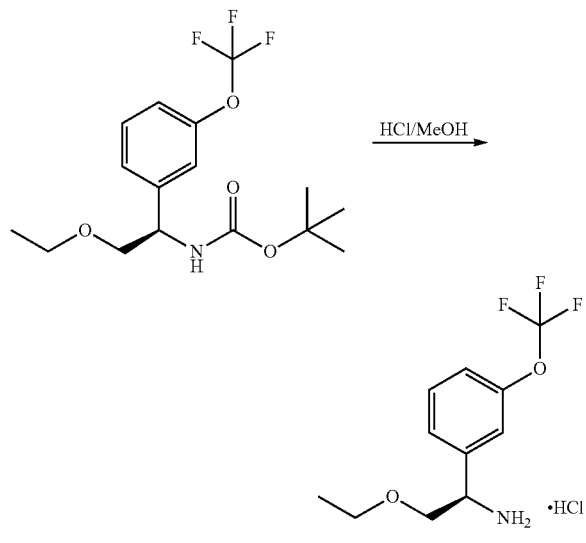

To a solution of tert-butyl (R)-(2-ethoxy-1-(3-(trifluoromethoxy)phenyl)ethyl)carbamate (5.9 g) in MeOH (100 mL) was added HCl/MeOH (4 M, 63.33 mL) at 25° C. and this mixture was stirred at 25° C. for 16 hours. The solution was concentrated to afford (R)-2-ethoxy-1-(3-(trifluoromethoxy)phenyl)ethan-1-amine hydrochloride (4.5 g).

Iii: (S)-1-(3-(trifluoromethoxy)phenyl)propan-1-amine hydrochloride

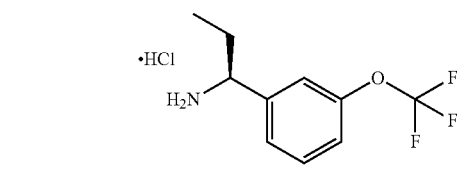

Step 1: Preparation of (S,E)-2-methyl-N-(3-(trifluoromethoxy)benzylidene)propane-2-sulfinamide

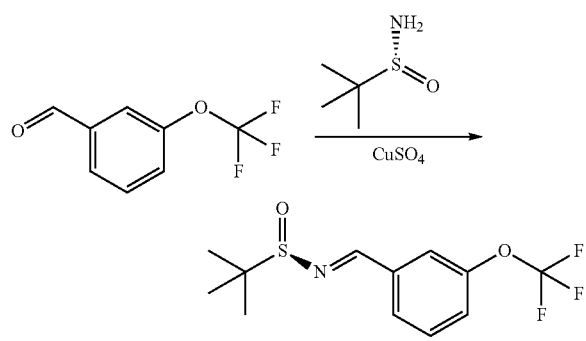

A mixture of 3-(trifluoromethoxy)benzaldehyde (10.0 g), (R)-2-methylpropane-2-sulfinamide (7.7 g) and CuSO₄ (12.6 g) in DCE (200 mL) was stirred at 55° C. for 16 hours. The mixture was filtered and the filter cake was washed with DCM (200 mL). The filtrate was concentrated. The residue was purified by chromatography (SiO₂, 0-10% Ethylacetate/petroleum ether gradient) to give (S,E)-2-methyl-N-(3-(trifluoromethoxy)benzylidene)propane-2-sulfinamide (12.6 g).

Step 2: Preparation of (S)-2-methyl-N—((S)-1-(3-(trifluoromethoxy)phenyl)propyl)propane-2-sulfinamide

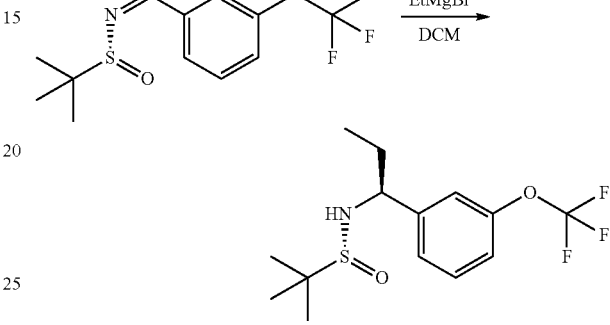

To a solution of (S,E)-2-methyl-N-(3-(trifluoromethoxy)benzylidene)propane-2-sulfinamide (2.0 g) in DCM (40 mL) at 0° C., EtMgBr (3M in Et₂O, 9.1 mL) was added dropwise. The resulting mixture was stirred at 0° C. for 1 hour and 20° C. for 3 hours. The mixture was cooled to 0° C. and sat.aq NH₄Cl (100 mL) was added. The mixture was extracted with DCM (100 mL×2), the phases were separated, and the organic layer was washed with brine (200 mL), dried over Na₂SO₄ and concentrated. The residue was purified by chromatography (SiO₂, 0-50% ethyl acetate/petroleum ether gradient) to yield the product (1.4 g).

Step 3: Preparation of (S)-1-(3-(trifluoromethoxy)phenyl)propan-1-amine hydrochloride

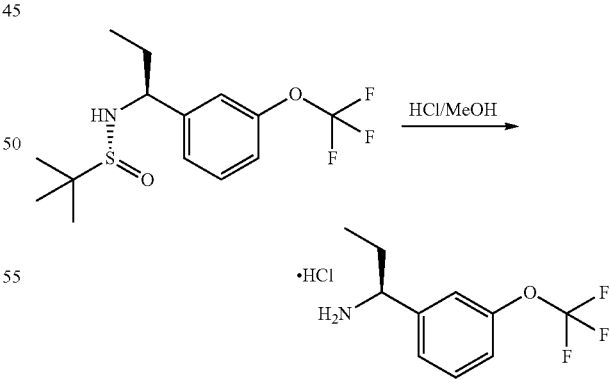

To a solution of (S)-2-methyl-N—((S)-1-(3-(trifluoromethoxy)phenyl)propyl)propane-2-sulfinamide (1.4 g) in MeOH (40 mL) was added HCl/MeOH (4M, 20 mL). The resulting mixture was stirred at 30° C. for 12 hours and then concentrated to yield the crude (S)-1-(3-(trifluoromethoxy)phenyl)propan-1-amine hydrochloride, which was used without further purification (1 g)

IIm: (S)-3-amino-3-(3-(trifluoromethoxy)phenyl)
propanenitrile hydrochloride

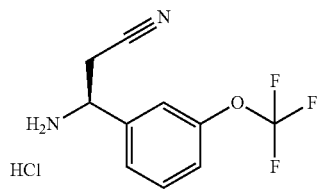 [SMILES: Cl ; N#CC[C@H](N)c1cccc(OC(F)(F)F)c1]

Step 1: Preparation of tert-butyl (R)-(2-hydroxy-1-
(3-(trifluoromethoxy)phenyl)ethyl)carbamate This intermediate was prepared as described for intermediate IIk, Step 1-5

Step 2: Preparation of (R)-2-((tert-butoxycarbonyl)
amino)-2-(3-(trifluoromethoxy) phenyl)ethyl methanesulfonate

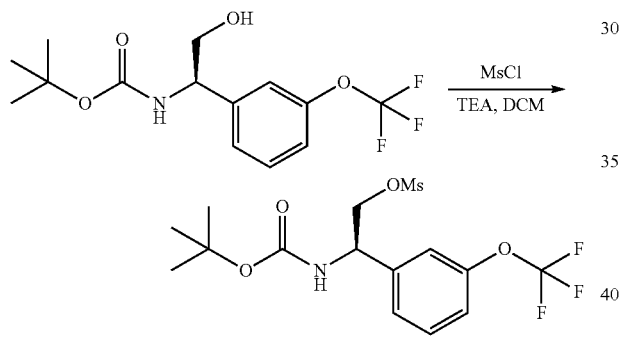

To a solution of tert-butyl (R)-(2-hydroxy-1-(3-(trifluoromethoxy)phenyl)ethyl)carbamate (2 g) in DCM (20 mL) was added Et$_3$N (756 mg), then methanesulfonyl chloride (1.75 g) was added at 0° C. The mixture was stirred at 20° C. for 16 hours. The reaction mixture was washed with saturated aqueous NH$_4$Cl solution (15 mL), dried over anhydrous Na$_2$SO$_4$, filtered and concentrated to afford (R)-2-((tert-butoxycarbonyl)amino)-2-(3-(trifluoromethoxy) phenyl)ethyl methanesulfonate (2.50 g, crude) which was used in the next step without purification.

Step 3: Preparation of (S)-3-amino-3-(3-(trifluoromethoxy) phenyl)propanenitrile hydrochloride

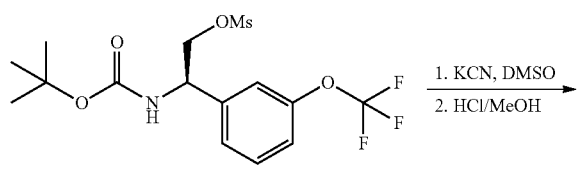

-continued

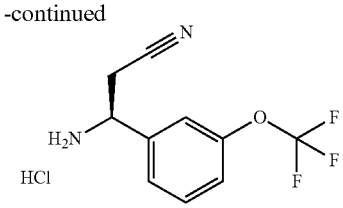

To a solution of (R)-2-((tert-butoxycarbonyl)amino)-2-(3-(trifluoromethoxy)phenyl)ethyl methanesulfonate (420 mg) in DMSO (5 mL) was added KCN (225 mg) at 20° C. The mixture was stirred at 50° C. for 16 hours. The reaction mixture was diluted with 10% Na$_2$CO$_3$ solution (40 mL) and extracted with EtOAc (30 mL×3). The combined organic extracts were washed with water (50 mL) and brine (50 mL), then dried over Na$_2$SO$_4$, filtered and concentrated. The residue was purified by chromatography (SiO$_2$, Petroleum ether/Ethyl acetate=5/1 to 4/1) to afford tert-butyl (S)-(2-cyano-1-(3-(trifluoromethoxy)phenyl)ethyl)carbamate (665 mg).
$^1$H NMR (400 MHz, CDCl$_3$): δ 7.46 (t, 1H), 7.33 (d, 1H), 7.24 (m, 2H), 7.04 (d, 1H), 5.31-5.38 (m, 1H), 3.73-3.71 (m, 1H), 3.11-3.05 (m, 1H), 2.84-2.92 (m, 2H), 2.49-2.43 (m, 1H), 2.28-2.37 (m, 1H), 0.93 (s, 9H).

To a solution of tert-butyl (S)-(2-cyano-1-(3-(trifluoromethoxy)phenyl)ethyl)carbamate (400 mg) in MeOH (8 mL) was added HCl/MeOH (4 M, 4.00 mL) at 0° C. The mixture was stirred at 25° C. for 16 hours. Then the reaction mixture was concentrated to afford (S)-3-amino-3-(3-(trifluoromethoxy) phenyl)propanenitrile hydrochloride (280 mg, crude).

IIn: (S)-4-amino-4-(3-(trifluoromethoxy)phenyl)
butanenitrile hydrochloride

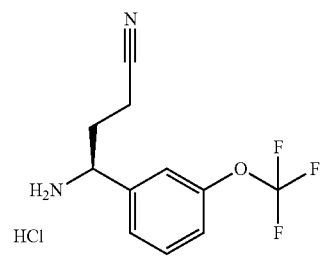 [SMILES: Cl ; N#CCC[C@H](N)c1cccc(OC(F)(F)F)c1]

Step 1: Preparation of (R,E)-2-methyl-N-(3-(trifluoro-methoxy)benzylidene)propane-2-sulfinamide

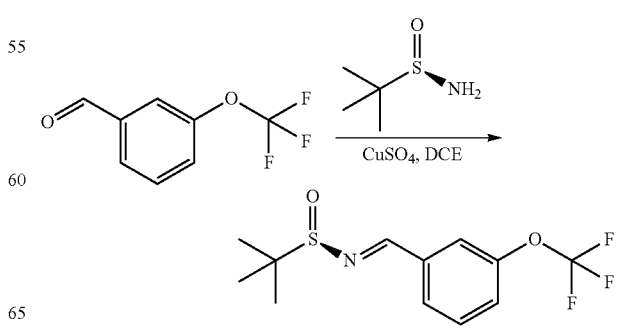

To a solution of 3-(trifluoromethoxy)benzaldehyde (30 g) and (R)-2-methylpropane-2-sulfinamide (23.0 g) in DCE (600 mL) was added CuSO₄ (37.8 g). The mixture was stirred at 55° C. for 24 hours and filtered. The filtercake was washed with DCM (300 mL). The filtrates were combined and concentrated, and the residue was purified by chromatography (SiO₂, Petroleum ether/Ethyl acetate=0/1 to 5:1) to afford (R,E)-2-methyl-N-(3-(trifluoro-methoxy)benzylidene)propane-2-sulfinamide (41.8 g).

Step 2: Preparation of ethyl (S)-3-(((R)-tert-butylsulfinyl)amino)-3-(3-(trifluoromethoxy) phenyl)propanoate

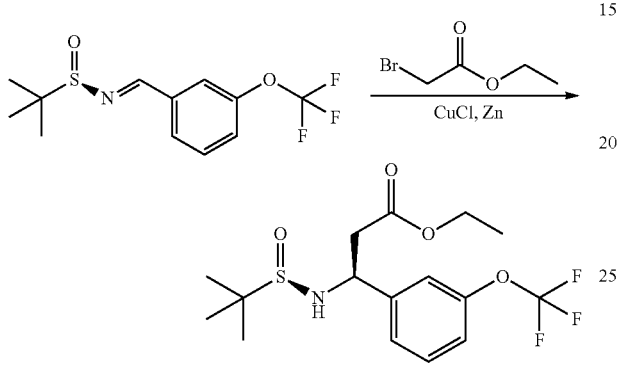

A solution of (R,E)-2-methyl-N-(3-(trifluoro-methoxy)benzylidene)propane-2-sulfinamide (5 g) in THF (60 mL) was added to a suspension of activated Zn (11.15 g), CuCl (2.5 g) and ethyl 2-bromoacetate (7.1 g) in THF (60 mL) at 0° C. The reaction mixture was stirred at 50° C. for 2 hours, and filtered. The filtercake was washed with DCM (400 mL), the combined organic filtrates were concentrated. The residue was purified by chromatography (SiO₂, Petroleum ether/Ethyl acetate=1/0 to 5/1) to afford ethyl (S)-3-(((R)-tert-butylsulfinyl)amino)-3-(3-(trifluoromethoxy) phenyl)propanoate (7 g, crude).

¹H NMR (CDCl₃ 400 MHz): δ 7.36 (t, 2H), 7.20 (s, 1H), 7.14 (d, 1H), 5.78 (d, 1H), 5.14-5.10 (m, 1H), 4.14-4.10 (m, 2H), 3.05-2.89 (m, 2H), 1.31 (s, 9H), 1.18 (t, 3H).

Step 3: Preparation of (R)—N—((S)-3-hydroxy-1-(3-(trifluoromethoxy)phenyl)propyl)-2-methylpropane-2-sulfinamide

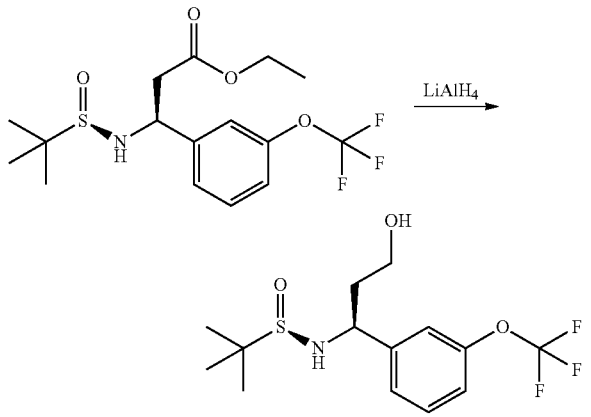

To a solution of ethyl (S)-3-(((R)-tert-butylsulfinyl)amino)-3-(3-(trifluoromethoxy) phenyl)propanoate (7 g) in THF (70 mL) was added LiAlH₄ (696 mg) at 0° C. The resulting mixture was stirred at 0° C. for 1 hour, and then quenched by sequential addition of H₂O (0.7 mL), 10% NaOH (0.7 mL) solution and H₂O (2.1 mL) at 0° C. The mixture was filtered. The residue was concentrated to afford the crude (R)—N—((S)-3-hydroxy-1-(3-(trifluoromethoxy) phenyl)propyl)-2-methylpropane-2-sulfinamide (4.2 g).

Step 4: Preparation of (S)-3-amino-3-(3-(trifluoromethoxy)phenyl)propan-1-ol hydrochloride

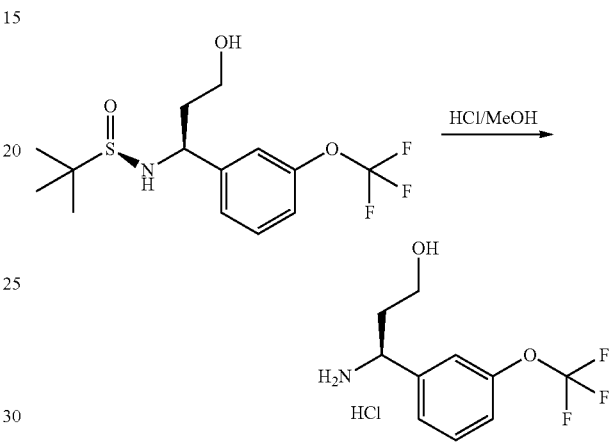

The crude (R)—N—((S)-3-hydroxy-1-(3-(trifluoromethoxy) phenyl)propyl)-2-methylpropane-2-sulfinamide (4 g) from the previous reaction step, was dissolved in MeOH (40 mL) and added HCl/MeOH (4 M, 23.6 mL). The reaction mixture was stirred at 20° C. for 16 hours, and was concentrated to afford (S)-3-amino-3-(3-(trifluoromethoxy)phenyl)propan-1-ol hydrochloride (3.2 g, crude)

Step 5: Preparation of tert-butyl (S)-(3-hydroxy-1-(3-(trifluoromethoxy)phenyl)propyl)carbamate

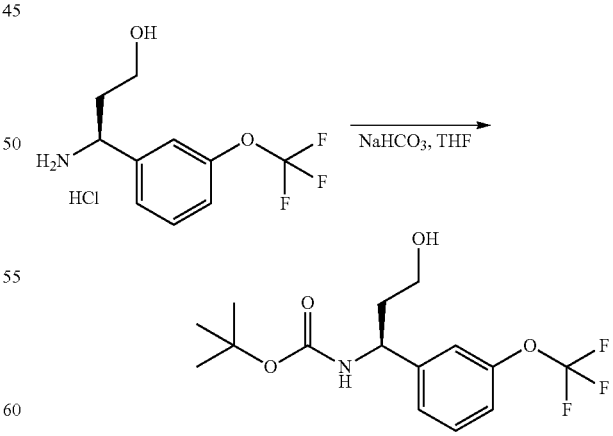

Crude ethyl (S)-3-(((R)-tert-butylsulfinyl)amino)-3-(3-(trifluoromethoxy) phenyl)propanoate from the previous reaction step (3.2 g) was dissolved in THF (35 mL) and added Boc₂O (10.28 g) and NaHCO₃ (2 g). The reaction mixture was stirred at 20° C. for 16 hours. The mixture was concentrated, and the residue was diluted with water (70 mL), extracted by DCM (100 mL×3), and the combined organic extracts were dried over Na₂SO₄, filtered and concentrated. The residue was purified by chromatography (SiO₂, Petroleum ether/Ethyl acetate=1/0 to 2/1) to afford tert-butyl (S)-(3-hydroxy-1-(3-(trifluoromethoxy)phenyl)propyl)carbamate (3.2 g)

Step 6: Preparation of (S)-3-((tert-butoxycarbonyl)amino)-3-(3-(trifluoromethoxy) phenyl)propyl methanesulfonate

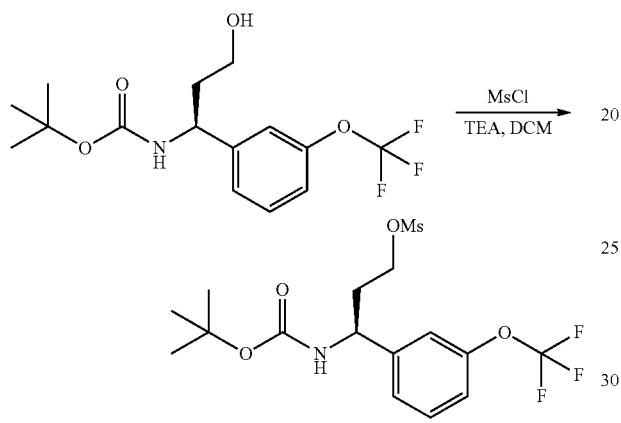

To a solution of tert-butyl (S)-(3-hydroxy-1-(3-(trifluoromethoxy)phenyl)propyl)carbamate (1 g) in DCM (30 mL) was added Et₃N (905 mg) and methanesulfonyl chloride (683 mg) at 0° C. The reaction mixture was stirred at 20° C. for 16 hours, and then washed with ice water (15 mL), dried over anhydrous Na₂SO₄, filtered and concentrated to afford ((S)-3-((tert-butoxycarbonyl)amino)-3-(3-(trifluoromethoxy) phenyl)propyl methanesulfonate (1.2 g)

Step 7: Preparation of tert-butyl (S)-(3-cyano-1-(3-(trifluoromethoxy)phenyl)propyl)carbamate

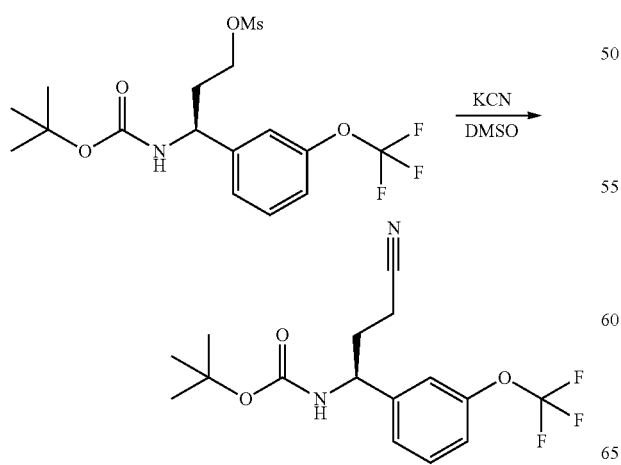

((S)-3-((tert-butoxycarbonyl)amino)-3-(3-(trifluoromethoxy) phenyl)propyl methanesulfonate obtained in the previous step was dissolved in DMSO (35 mL) and added KCN (661 mg) at 20° C. The reaction mixture was stirred at 50° C. for 16 hours, and then diluted with 10% Na₂CO₃ solution (40 mL) and extracted with EtOAc (70 mL×3). The combined organic extracts were washed with water (50 mL) and brine (50 mL), then dried over Na₂SO₄, filtered and concentrated. The residue was purified by chromatography (SiO₂, Petroleum ether/Ethyl acetate=1/0 to 3/1) to afford tert-butyl (S)-(3-cyano-1-(3-(trifluoromethoxy)phenyl)propyl)carbamate (990 mg).

Step 8: Preparation of (S)-4-amino-4-(3-(trifluoromethoxy)phenyl)butanenitrile hydrochloride

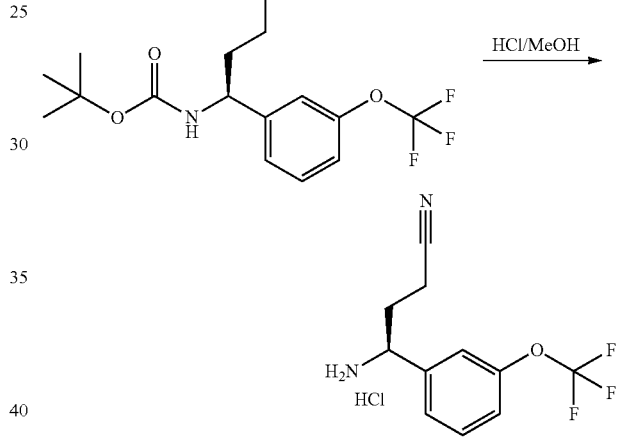

To a solution of tert-butyl (S)-(3-cyano-1-(3-(trifluoromethoxy)phenyl) propyl)carbamate (900 mg) in MeOH (14 mL) was added HCl/MeOH (4 M, 6.53 mL). The mixture was stirred at 20° C. for 16 hours and concentrated to afford (S)-4-amino-4-(3-(trifluoromethoxy)phenyl)butanenitrile hydrochloride (850 mg).

IIo: (S)-3,3-difluoro-1-(3-(trifluoromethoxy)phenyl)propan-1-amine hydrochloride

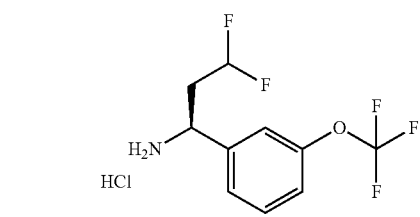 [SMILES: Cl ; N[C@@H](CC(F)F)c1cccc(OC(F)(F)F)c1]

Prepared as described for IIi using 3-(trifluoromethoxy)benzaldehyde as starting material.

IIp: (R)-2-methoxy-1-(3-(trifluoromethoxy)phenyl)ethan-1-amine hydrochloride

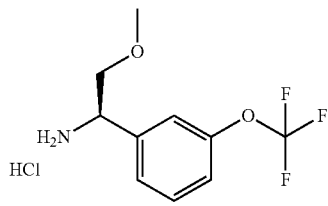 [SMILES: Cl ; COC[C@H](N)c1cccc(OC(F)(F)F)c1]

Step 1: Preparation of ethyl (R)-2-((tert-butoxycarbonyl)amino)-2-(3-(trifluoromethoxy)phenyl)acetate

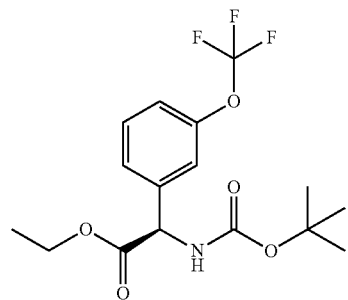 [SMILES: CCOC(=O)[C@H](NC(=O)OC(C)(C)C)c1cccc(OC(F)(F)F)c1]

This intermediate was prepared as described for IIk, Step 1-4.

Step 2: Preparation of tert-butyl (R)-(2-hydroxy-1-(3-(trifluoromethoxy)phenyl)ethyl)carbamate

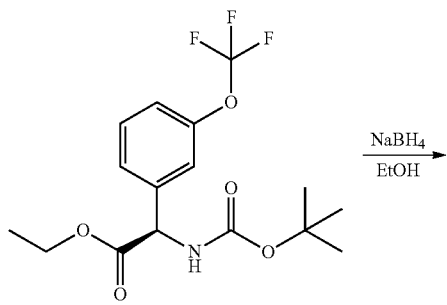

To a solution of ethyl (R)-2-((tert-butoxycarbonyl)amino)-2-(3-(trifluoromethoxy)phenyl) acetate (10 g) in EtOH (90 mL) was added NaBH$_4$ (4.17 g) at 0° C. The mixture was removed from the cold bath and stirred for 2 hours. The reaction was quenched with water (20 mL) and concentrated. The residue was purified by column chromatography (SiO$_2$, Petroleum ether/Ethyl acetate=1/0 to 3/1) to afford the product (13.6 g).

$^1$H NMR (CDCl$_3$ 400 MHz): δ 7.39 (t, 1H), 7.26 (d, 1H), 7.17-7.15 (m, 2H), 5.34 (s, 1H), 4.80 (s, 1H), 3.93-3.84 (m, 2H), 2.06 (s, 1H), 1.45 (s, 9H).

Step 3: Preparation of tert-butyl (R)-(2-methoxy-1-(3-(trifluoromethoxy)phenyl)ethyl)carbamate

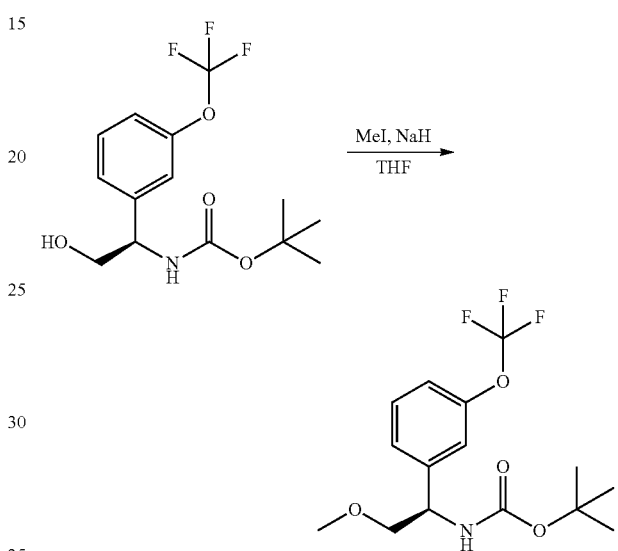

To a solution of tert-butyl (R)-(2-hydroxy-1-(3-(trifluoromethoxy)phenyl)ethyl)carbamate (1 g) and MeI (4 g) in THF (70 mL) was added NaH (149 mg, 60% in mineral oil) at 0° C. The mixture was stirred at 0° C. for 1 hour and stirred at 25° C. for 16 hours. Water (1 mL) was added to quench the reaction. THF was removed and EtOAc (200 mL) was added into the residue. The solution was washed by water (50 mL×3) and concentrated. The residue was purified by column chromatography (SiO$_2$, Petroleum ether/Ethyl acetate=0/1 to 5/1) to afford tert-butyl (R)-(2-methoxy-1-(3-(trifluoromethoxy)phenyl)ethyl)carbamate (3.2 g).

$^1$H NMR (CDCl$_3$ 400 MHz): δ 7.36 (t, 1H), 7.25 (m, 1H), 7.19 (s, 1H), 7.12 (d, 1H), 5.34 (s, 1H), 4.83 (s, 1H), 3.63-3.56 (m, 2H), 3.35 (s, 3H), 1.43 (s, 9H).

Step 4: Preparation of (R)-2-methoxy-1-(3-(trifluoromethoxy)phenyl)ethan-1-amine hydrochloride

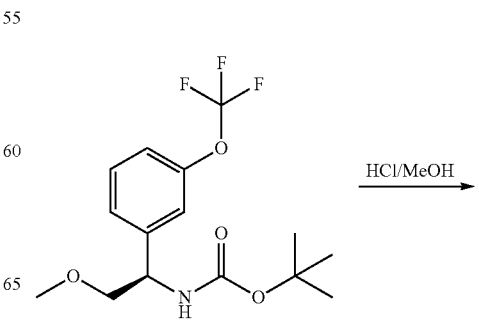

-continued

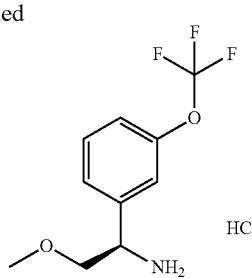

To a solution of tert-butyl (R)-(2-methoxy-1-(3-(trifluoromethoxy)phenyl)ethyl)carbamate (2.7 g) in MeOH (40 mL) was added HCl/MeOH (4 M, 40 mL) at 25° C. The mixture was stirred at 25° C. for 16 hours. The mixture was concentrated to afford the desired product (1.9 g, crude).

IIIa: (S)-3-hydroxy-4,4-dimethylpentanoic acid

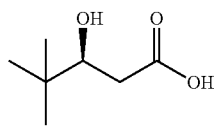

Prepared according to literature as described in Wang Z. et al: Tetrahedron: Asymmetry 10 (1999) 225-228.

IIIb: 2-(3,3-Difluoro-1-hydroxycyclobutyl)acetic acid

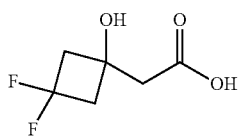 [SMILES: O=C(O)CC1(O)CC(F)(F)C1]

Step 1: Preparation of ethyl 2-(3,3-difluoro-1-hydroxy-cyclobutyl)acetate

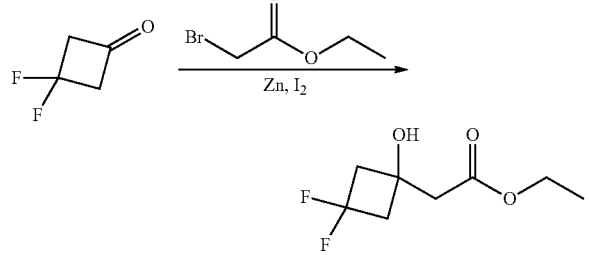

To a solution 3,3-difluorocyclobutanone (0.2 g), Zn (198 mg) and I$_2$ (10 mg) in THF (13 mL) under N$_2$, ethyl 2-bromoacetate (378 mg) was added dropwise. The mixture was stirred at 55° C. for 6 hours. H$_2$SO$_4$ (10%, 10 mL) was carefully added to the reaction mixture at 0° C., and the mixture was extracted with ethyl acetate (20 mL×3). The organic extract was washed with NaHCO$_3$ (sat.aq, 10 mL), dried over Na$_2$SO$_4$ and concentrated. The crude product (0.26 g) was used directly without further purification.

Step 2: Preparation of 2-(3,3-difluoro-1-hydroxy-cyclobutyl) acetic acid

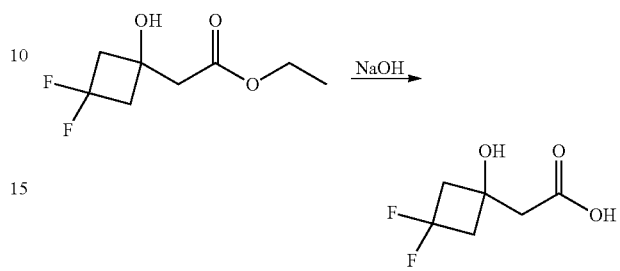

To a solution of ethyl 2-(3,3-difluoro-1-hydroxy-cyclobutyl) acetate (0.26 g) in MeOH (10 mL) and H$_2$O (2 mL), NaOH (107 mg) was added at 0° C. The mixture was stirred at 20° C. for 8 hours. The reaction solution was cooled to 0° C. and 1N HCl was added to the solution until pH reached 1-2. The residue was diluted with brine (10 mL) and extracted with methyl-tert-butyl ether (30 mL×5). The combined organic extracts were dried over Na$_2$SO$_4$, filtered and concentrated. The crude product (0.24 g) was used without further purification.

IIIc: 3-(1-fluorocyclopropyl)-3-hydroxybutanoic acid

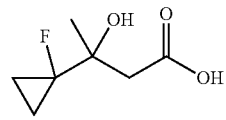

Step 1: Preparation of ethyl 3-(1-fluorocyclopropyl)-3-hydroxy-butanoate

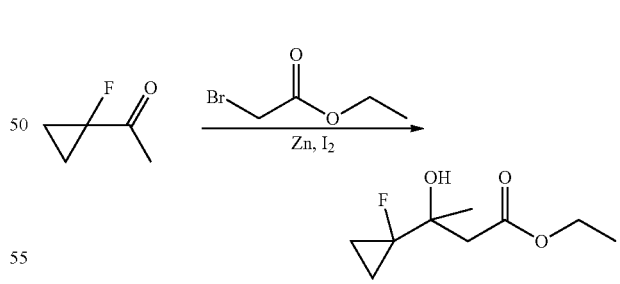

A solution of 1-(1-fluorocyclopropyl)ethanone (0.5 g), Zn (512 mg) and I$_2$ (62 mg) in THF (30 mL) was stirred at 20° C. until the solution changed to colorless and ethyl 2-bromoacetate (981 mg) was added dropwise. The resulting mixture was stirred at 20° C. for 0.5 hour and 65° C. for 4.5 hours. The reaction was washed with 10% aq. H$_2$SO$_4$ (20 mL) and extracted with EtOAc (50 mL×2). The organic extracts were washed with brine (100 mL), dried over Na$_2$SO$_4$ and concentrated to afford ethyl 3-(1-fluorocyclopropyl)-3-hydroxy-butanoate (0.83 g, crude).

Step 2: Preparation of 3-(1-fluorocyclopropyl)-3-hydroxy-butanoic acid

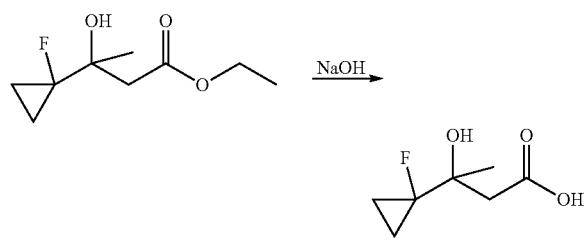

To a solution of ethyl 3-(1-fluorocyclopropyl)-3-hydroxy-butanoate (0.83 g) in EtOH (10 mL) was added a solution of NaOH (350 mg) in H₂O (3 mL). The reaction mixture was stirred at 20° C. for 2 hours and then extracted with EtOAC (50 mL×2). The aqueous layer was acidified by 10% HCl to pH=3 and extracted with EtOAC (50 mL×2). The combined organic extracts were washed with brine (100 mL), dried over Na₂SO₄ and concentrated to afford 3-(1-fluorocyclopropyl)-3-hydroxy-butanoic acid (0.57 g, crude).

IIId: 3-Cyclopropyl-3-hydroxybutanoic acid

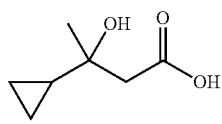

Step 1: Preparation of methyl 3-cyclopropyl-3-hydroxybutanoate

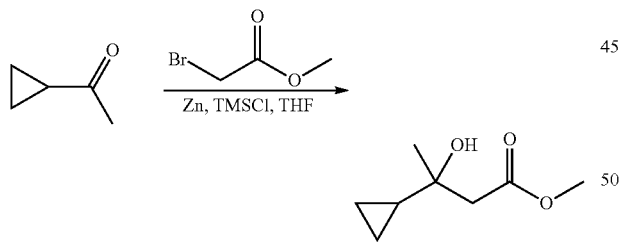

Zn (12.4 g) in THF (150 mL) was added TMSCl (1.3 g), and the resulting mixture was stirred at 20° C. for 15 minutes and then heated to 70° C. The heating was stopped, and methyl 2-bromoacetate (21.8 g) was added dropwise at such a rate that the solvent boiled gently. The resulting mixture was stirred at 70° C. for 1 hour and 20° C. for 1 hour, then a solution of 1-cyclopropylethanone (10 g) in THF (50 mL) was added. The reaction was stirred at 20° C. for 16 hours. The mixture was poured onto NH₃.H₂O on ice (100 mL, 28%), and extracted with ethyl acetate (150 mL×2). The organic extract was washed with water (150 mL) and brine (150 mL), dried over Na₂SO₄ and concentrated to give the desired product (8.9 g, crude).

Step 2: Preparation of 3-cyclopropyl-3-hydroxybutanoic acid

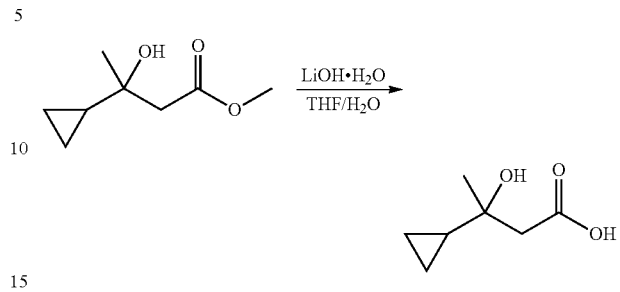

A mixture of crude methyl 3-cyclopropyl-3-hydroxybutanoate (8.9 g) and LiOH.H₂O (11.8 g) in THF (100 mL) and H₂O (50 mL) was stirred at 20° C. for 16 hours. H₂O (50 ml) was added and extracted with ethyl acetate (100 mL×2). The organic extracts were discarded. The pH of the aqueous layer was adjusted to ~5 with 2N HCl, extracted with ethyl acetate (100 mL×3) and the combined organic fractions were washed with brine (100 mL×10), dried over Na₂SO₄, filtered and concentrated to give the desired product in 30% overall yield (5.1 g)

¹H NMR (400 MHz, CDCl₃) δ 2.67-2.51 (m, 2H), 1.25 (s, 3H), 0.90-1.00 (m, 1H), 0.33-0.50 (m, 4H).

IIIe: 5,5,5-Trifluoro-3-hydroxy-3-methylpentanoic acid

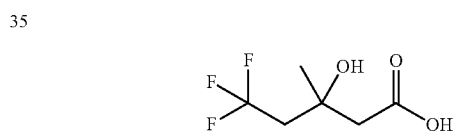

Step 1: Preparation of ethyl 5,5,5-trifluoro-3-hydroxy-3-methylpentanoate

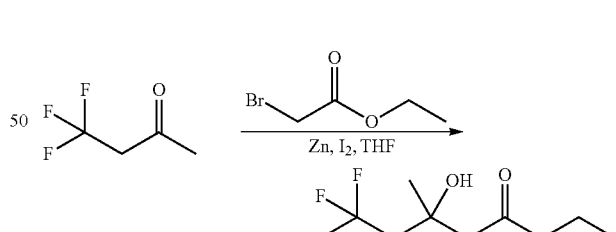

To a mixture of Zn (6.9 g) and I2 (89 mg) in THF (80 mL) was added 4,4,4-trifluorobutan-2-one (4.4 g) and ethyl 2-bromoacetate (6.4 g) at 15° C. The mixture was stirred at 60° C. for 6 hours. The reaction mixture was cooled to 0° C. and quenched with H₂SO₄ (100 mL, 10% aq).

The mixture was extracted with ethyl acetate (15 mL×3). The combined organic extract was washed with brine (15 mL) and dried over Na₂SO₄, filtered and concentrated. The product was obtained (11.00 g, crude) and was used directly without further purification.

Step 2: Preparation of 5,5,5-trifluoro-3-hydroxy-3-methylpentanoic acid

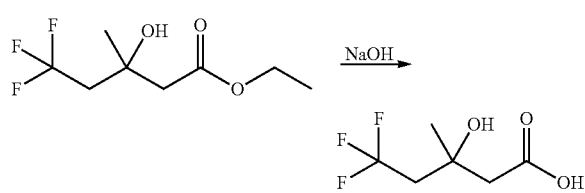

A mixture of ethyl 5,5,5-trifluoro-3-hydroxy-3-methylpentanoate (11 g, crude) and NaOH (4.1 g) in H$_2$O (150 mL) was stirred at 15° C. for 16 hours. The pH was adjusted to 2 with sat. KHSO$_4$ at 0° C., and the mixture extracted with ethyl acetate (200 mL×3). The combined organic extract was washed with brine (300 mL), dried over Na$_2$SO$_4$, filtered and concentrated to afford the product (10 g, crude)

The following were prepared by the same methodology as described for IIIe, using the relevant starting materials:

IIIf: 3-hydroxy-3,4-dimethylpentanoic acid

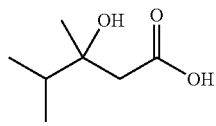

$^1$H NMR (CDCl$_3$ 400 MHz): δ 2.65-2.46 (m, 2H), 2.09 (s, 1H), 1.85-1.76 (m, 1H), 1.20 (s, 3H), 0.93 (dd, 6H).

IIIg: 3-Hydroxy-3,5-dimethyl-hexanoic acid

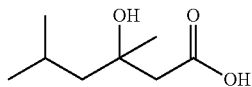

$^1$H NMR (CDCl$_3$ 400 MHz): δ 2.64-2.50 (m, 2H), 1.85-1.79 (m, 1H), 1.49 (d, 2H), 1.32 (s, 3H), 1.03-0.97 (m, 6H).

IIIh: 3-(3,3-Dimethylcyclobutyl)-3-hydroxy-propanoic acid

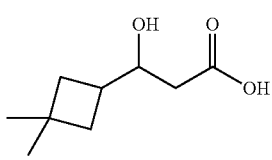

Step 1: Preparation of ethyl 3-(3,3-dimethylcyclobutyl)-3-hydroxy-propanoate

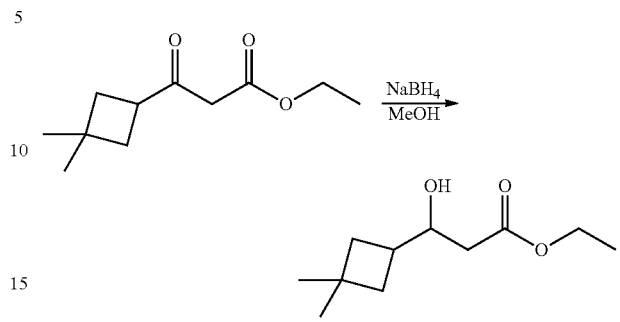

To a solution of ethyl 3-(3,3-dimethylcyclobutyl)-3-oxo-propanoate (IVd) (1 g) in MeOH (8 mL) was added NaBH$_4$ (95 mg). The mixture was stirred at 0° C. for 10 min. and quenched by addition of H$_2$O (1 mL), concentrated and then diluted with EtOAc (30 mL), dried over Na$_2$SO$_4$, filtered and evaporated. The residue was purified by chromatography (SiO$_2$, Petroleum ether/Ethyl acetate=5/1 to 4/1) to afford ethyl 3-(3,3-dimethylcyclobutyl)-3-hydroxy-propanoate (907 mg)

$^1$H NMR (DMSO-d6 400 MHz): δ 4.70 (d, 1H), 4.06-4.00 (m, 2H), 3.71-3.68 (m, 1H), 2.26-2.23 (m, 1H), 2.15-2.12 (m, 2H), 1.63-1.59 (m, 3H), 1.52-1.49 (m, 1H), 1.17 (t, 3H), 1.09 (s, 3H), 0.99 (s, 3H).

Step 2: Preparation of 3-(3,3-dimethylcyclobutyl)-3-hydroxy-propanoic acid

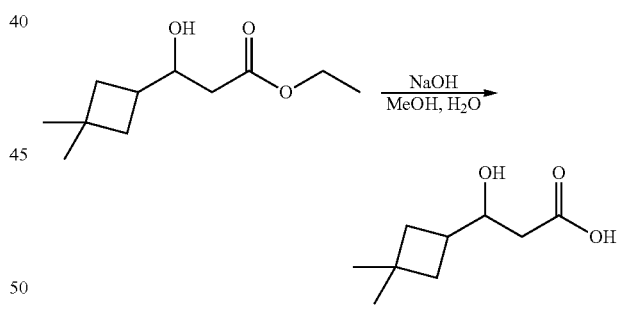

To a solution of ethyl 3-(3,3-dimethylcyclobutyl)-3-hydroxy-propanoate (900 mg) in MeOH (10 mL) was added a solution of NaOH (377 mg) in H$_2$O (5 mL). The mixture was stirred at 25° C. for 4 hours. The reaction mixture was added 10% HCl solution to adjust pH=3-4, then diluted with H$_2$O (30 mL) and extracted with EtOAc (30 mL×2), the combined organic layers were dried over Na$_2$SO$_4$, filtered and concentrated to afford 3-(3,3-dimethylcyclobutyl)-3-hydroxy-propanoic acid (760 mg).

$^1$H NMR (DMSO-d6 400 MHz): δ 11.96-11.95 (m, 1H), 4.65-4.61 (m, 1H), 3.71-3.66 (m, 1H), 2.19-2.05 (m, 3H), 1.63-1.51 (m, 4H), 1.09 (s, 3H), 1.00 (s, 3H).

The following was prepared by the same methodology as described for IIIh, using the relevant starting materials:

IIIi: 3-cyclopentyl-3-hydroxy-propanoic acid

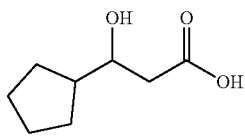 [SMILES: O=C(O)CC(O)C1CCCC1]

$^{1}$H NMR (DMSO-d6 400 MHz): δ 11.96 (s, 1H), 4.63 (s, 1H), 3.66 (s, 1H), 2.36-2.32 (m, 2H), 1.83-1.75 (m, 1H), 1.62-1.35 (m, 8H).

IVa: Ethyl 3-[1-(difluoromethyl)cyclopropyl]-3-oxo-propanoate

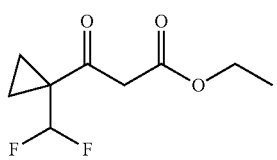

Step 1: Preparation of ethyl 3-[1-(difluoromethyl)cyclopropyl]-3-oxo-propanoate

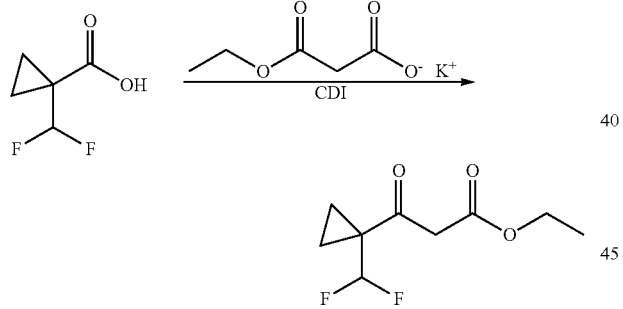

Et$_3$N (2.34 g) and MgCl$_2$ (1.8 g) was added to a suspension of (3-ethoxy-3-oxo-propanoyl)oxy potassium salt (2.6 g) in MeCN (30 mL) and stirred at 20° C. for 2 hours. A pre-stirred mixture of carbonyl-diimidazole (CDI) (1.4 g) and 1-(difluoromethyl) cyclopropane carboxylic acid (1 g) in MeCN (20 mL) was added at 0° C. and stirred at 20° C. for 14 hours. The reaction mixture was diluted with H$_2$O (30 mL) and extracted with ethyl acetate (80 mL×2). The combined organic extracts were washed with brine (30 mL), dried over Na$_2$SO$_4$, filtered and concentrated. The residue was purified by flash chromatography (SiO$_2$, eluent of 010% Ethyl acetate/petroleum ether gradient). To yield the product (0.98 g)

The following was prepared by the same methodology as described for IVa, using the relevant starting materials:

IVb: Ethyl 3-oxo-3-[1-(trifluoromethyl)cyclopropyl]propanoate

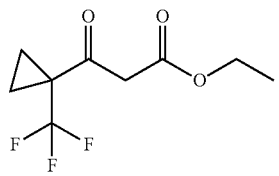

IVc: 3-(3,3-Difluorocyclobutyl)-3-oxopropanoate

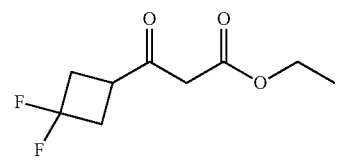

IVd: Ethyl 3-(3,3-dimethylcyclobutyl)-3-oxo-propanoate

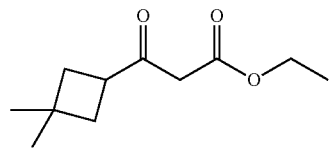

$^{1}$H NMR (CDCl$_3$ 400 MHz): δ 4.22-4.16 (m, 1H), 3.39 (s, 2H), 3.34-3.25 (m, 1H), 2.08-1.90 (m, 4H), 1.29 (t, 3H), 1.27 (s, 3H), 1.06 (s, 3H).

IVe: Ethyl 3-cyclopentyl-3-oxo-propanoate

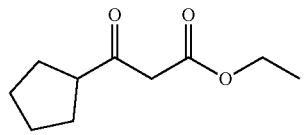

$^{1}$H NMR (CDCl$_3$ 400 MHz): δ 4.24-4.18 (m, 2H), 3.49 (s, 2H), 3.03-2.95 (m, 1H), 1.84-1.60 (m, 8H), 1.28 (t, 3H).

IVf: Ethyl 3-(1-ethylcyclopropyl)-3-oxo-propanoate

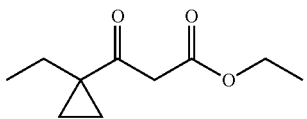

$^{1}$H NMR (CDCl$_3$ 400 MHz): δ 4.22-4.16 (m, 2H), 3.33 (s, 2H), 1.64-1.60 (m, 2H), 1.26-1.20 (m, 6H), 0.94 (t, 3H).

Va: (R)—N-(2-(difluoromethoxy)-1-(3-(difluoromethoxy) phenyl)ethyl)-4,4-dimethyl-3-oxopentanamide

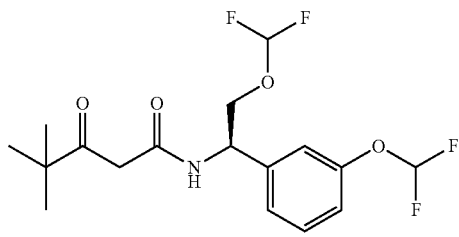 [SMILES: CC(C)(C)C(=O)CC(=O)N[C@@H](COC(F)F)c1cccc(OC(F)F)c1]

Step 1: Preparation of (R)—N-(2-(difluoromethoxy)-1-(3-(difluoromethoxy) phenyl)ethyl)-4,4-dimethyl-3-oxopentanamide

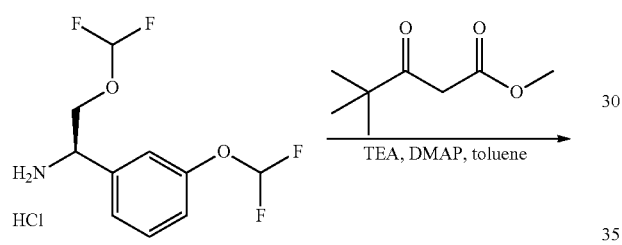

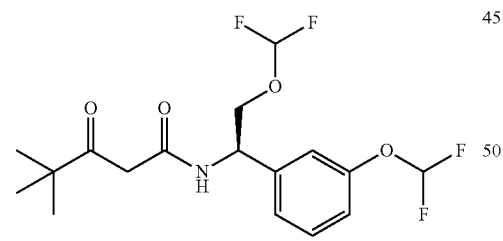

A solution of (R)-2-(difluoromethoxy)-1-(3-(difluoromethoxy)phenyl) ethan-1-amine hydrochloride (IIa)(0.6 g), methyl 4,4-dimethyl-3-oxo-pentanoate (750 mg), TEA (2.40 g) and DMAP (58 mg) in toluene (10 mL) was stirred at 90° C. for 16 hours. The mixture was diluted with EtOAc (50 mL), washed with water (30 mL) and brine (50 mL), dried over Na$_2$SO$_4$ and concentrated. The crude was purified by chromatography (SiO$_2$, 30% EA in Petroleum Ether) to give (R)—N-(2-(difluoromethoxy)-1-(3-(difluoromethoxy) phenyl)ethyl)-4,4-dimethyl-3-oxopentanamide (0.28 g).

The following intermediate was prepared by similar methodology as Va, using the relevant intermediates Vb: (R)—N-(2-ethoxy-1-(3-(trifluoromethoxy)phenyl)ethyl)-4,4-dimethyl-3-oxopentanamide

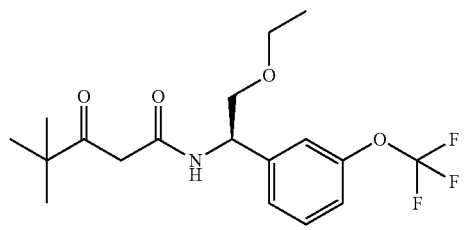 [SMILES: CCOC[C@H](NC(=O)CC(=O)C(C)(C)C)c1cccc(OC(F)(F)F)c1]

Prepared from IIk and 4,4-dimethyl-3-oxo-pentanoic acid.

Vc: (R)—N-(2-(difluoromethoxy)-1-(3-(difluoromethoxy)phenyl)ethyl)-3-oxo-3-(1-(trifluoromethyl)cyclopropyl)propanamide

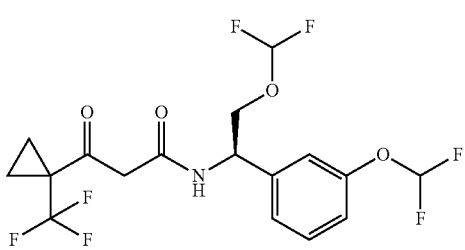 [SMILES: O=C(CC(=O)C1(C(F)(F)F)CC1)N[C@@H](COC(F)F)c1cccc(OC(F)F)c1]

Prepared from IIa and IVb

Vd: (R)—N-(2-(difluoromethoxy)-1-(3-(trifluoromethoxy) phenyl) ethyl)-3-oxo-3-(1-trifluoromethyl)cyclopropyl) propanamide

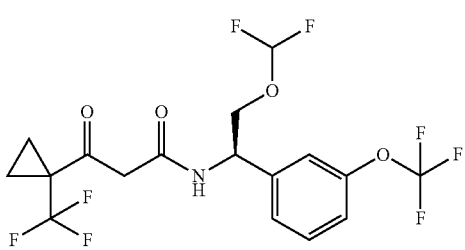 [SMILES: O=C(CC(=O)C1(C(F)(F)F)CC1)N[C@@H](COC(F)F)c1cccc(OC(F)(F)F)c1]

Prepared from IVb and IIb.

Ve: (R)-3-(3,3-difluorocyclobutyl)-N-(2-(difluoromethoxy)-1-(3-(difluoromethoxy)phenyl)ethyl)-3-oxopropanamide

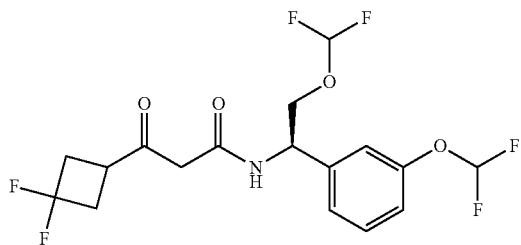 [SMILES: O=C(CC(=O)C1CC(F)(F)C1)N[C@@H](COC(F)F)c1cccc(OC(F)F)c1]

Prepared from IVc and IIa

Vf: (R)-3-(3,3-difluorocyclobutyl)-N-(2-(difluoromethoxy)-1-(3-(trifluoromethoxy)phenyl)ethyl)-3-oxopropanamide

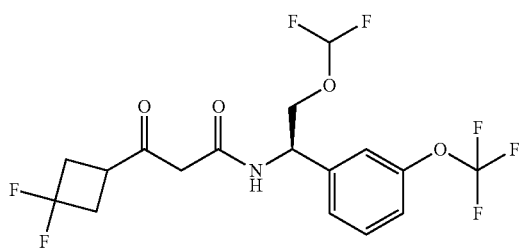 [SMILES: O=C(CC(=O)C1CC(F)(F)C1)N[C@@H](COC(F)F)c1cccc(OC(F)(F)F)c1]

Prepared from IVc and IIb

Vg: (S)-3-(3,3-difluorocyclobutyl)-N-(1-(3-(difluoromethoxy) phenyl)butyl)-3-oxopropanamide

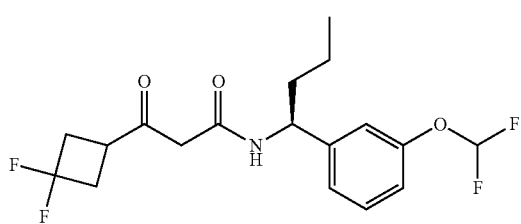 [SMILES: CCC[C@H](NC(=O)CC(=O)C1CC(F)(F)C1)c1cccc(OC(F)F)c1]

Prepared from IVc and IIg

Vh: (R)—N-(2-(difluoromethoxy)-1-(3-(difluoromethoxy)phenyl) ethyl)-3-(1-ethylcyclopropyl)-3-oxopropanamide

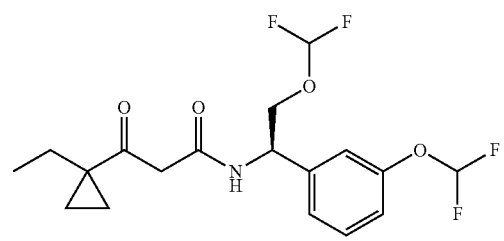 [SMILES: CCC1(C(=O)CC(=O)N[C@@H](COC(F)F)c2cccc(OC(F)F)c2)CC1]

Prepared from IVf and IIa

EXAMPLES

Example 1a: N—((R)-2-(difluoromethoxy)-1-(3-(difluoromethoxy)phenyl) ethyl)-3-hydroxy-4,4-dimethylpentanamide

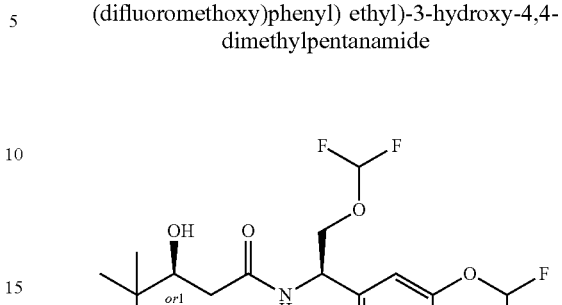

and Example 1b: N—((R)-2-(difluoromethoxy)-1-(3-(difluoromethoxy)phenyl) ethyl)-3-hydroxy-4,4-dimethylpentanamide

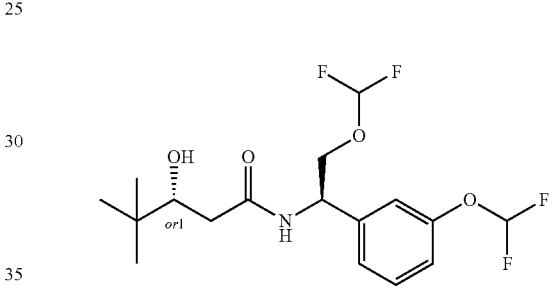

Step 1: Preparation of N—((R)-2-(difluoromethoxy)-1-(3-(difluoromethoxy) phenyl)ethyl)-3-hydroxy-4,4-dimethylpentanamide

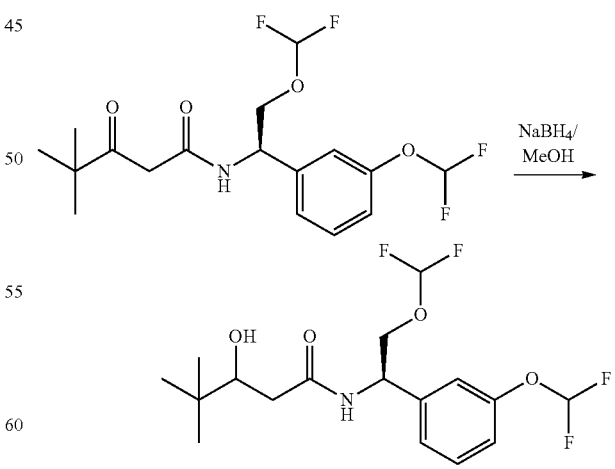

To a solution of (R)—N-(2-(difluoromethoxy)-1-(3-(difluoromethoxy) phenyl)ethyl)-4,4-dimethyl-3-oxopentanamide (Va) (0.28 g) in MeOH (10 mL) was added NaBH$_4$ (56 mg) at 0° C. The resulting mixture was stirred at 0° C. for 1 hour. The mixture was concentrated and the residue was redissolved in EtOAc (50 mL) and washed with water (50 mL) and brine (50 mL), dried over Na₂SO₄ and concentrated.

Step 2: Separation of (R)—N—((R)-2-(difluoromethoxy)-1-(3-(difluoromethoxy)phenyl)ethyl)-3-hydroxy-4,4-dimethylpentanamide and (S)—N—((R)-2-(difluoromethoxy)-1-(3-(difluoromethoxy)phenyl)ethyl)-3-hydroxy-4,4-dimethylpentanamide

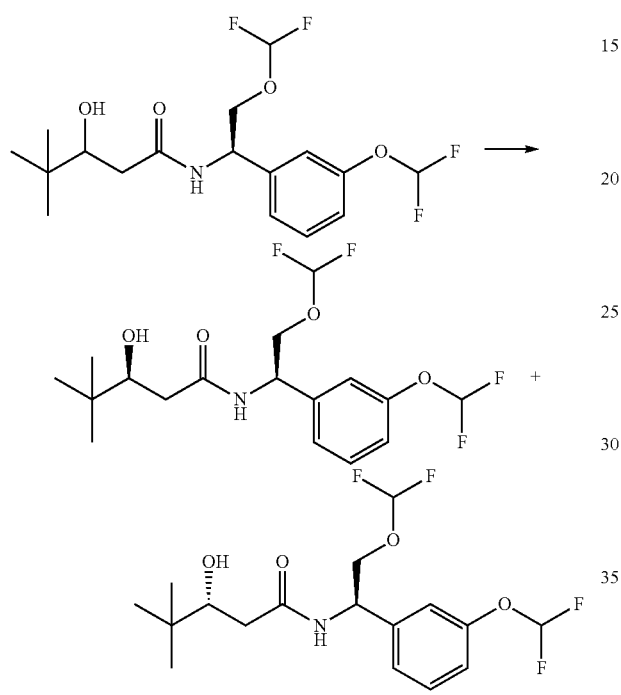

N—((R)-2-(difluoromethoxy)-1-(3-(difluoromethoxy)phenyl) ethyl)-3-hydroxy-4,4-dimethylpentanamide was separated by chromatography.

Example 1a

¹H NMR (CDCl₃ 400 MHz): δ 7.34 (t, 1H), 7.16 (d, 1H), 7.09 (s, 1H), 7.04 (d, 1H), 6.59 (d, 1H), 6.50 (t, 1H), 6.20 (t, 1H), 5.30-5.26 (m, 1H), 4.15-4.08 (m, 2H), 3.69-3.66 (m, 1H), 2.90 (d, 1H), 2.43 (dd, 1H), 2.28 (dd, 1H), 0.91 (s, 9H).
LC-MS: $t_R$=2.49 min (LC-MS Method 1), m/z=382.2 [M+H]⁺.
SFC: $t_R$=1.94 min (SFC Method 1), ee %=95.26%.

Example 1b

¹H NMR (CDCl₃ 400 MHz): δ 7.35 (t, 1H), 7.16 (d, 1H), 7.06-7.04 (m, 2H), 6.60 (d, 1H), 6.50 (t, 1H), 6.20 (t, 1H), 5.28 (m, 1H), 4.10 (m, 2H), 3.67 (m, 1H), 3.04 (d, 1H), 2.45 (dd, 1H), 2.28 (dd, 1H), 0.91 (s, 9H).
LC-MS: $t_R$=2.50 min (LC-MS Method 1), m/z=382.2 [M+H]⁺.
SFC: $t_R$=2.03 min (SFC Method 1), ee %=95.26%.

The following examples were prepared by similar methodology as described for 1a and 1b, using the relevant intermediates:

Example 2a: N—((R)-2-ethoxy-1-(3-(trifluoromethoxy)phenyl)ethyl)-3-hydroxy-4,4-dimethylpentanamide

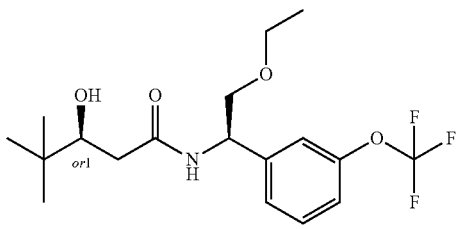 [SMILES: CCOC[C@H](NC(=O)C[C@H](O)C(C)(C)C)c1cccc(OC(F)(F)F)c1]

and Example 2b: N—((R)-2-ethoxy-1-(3-(trifluoromethoxy)phenyl)ethyl)-3-hydroxy-4,4-dimethylpentanamide

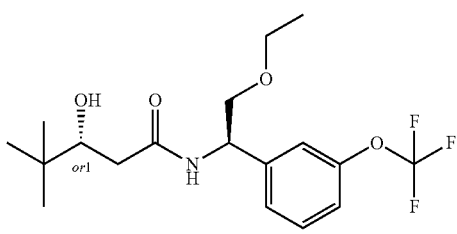 [SMILES: CCOC[C@H](NC(=O)C[C@@H](O)C(C)(C)C)c1cccc(OC(F)(F)F)c1]

Step 1: Preparation of N—((R)-2-ethoxy-1-(3-(trifluoromethoxy) phenyl)ethyl)-3-hydroxy-4,4-dimethylpentanamide

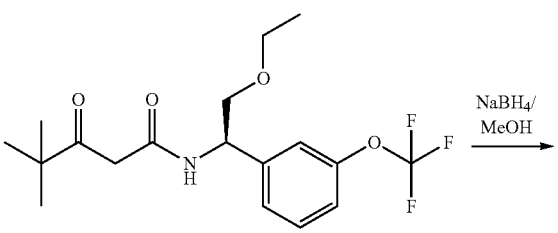

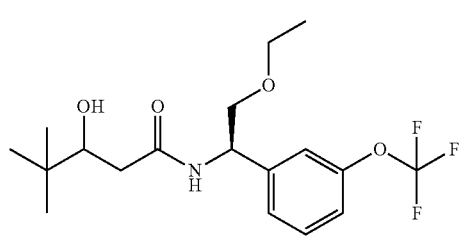

Prepared from Vb.

Step 2: Separation of (S)-3-hydroxy-4,4-dimethyl-N—((S)-1-(3-(2,2,2-trifluoroethoxy)phenyl)ethyl)pentanamide and (R)-3-hydroxy-4,4-dimethyl-N—((S)-1-(3-(2,2,2-trifluoroethoxy) phenyl)ethyl)pentanamide

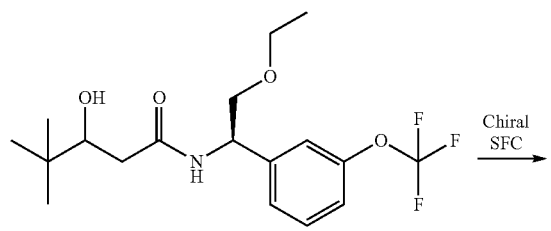

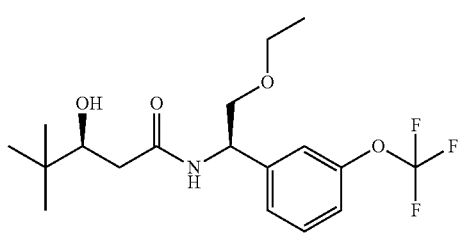

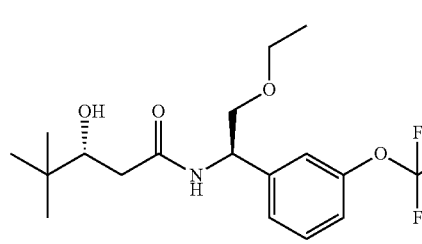

N—((R)-2-ethoxy-1-(3-(trifluoromethoxy)phenyl)ethyl)-3-hydroxy-4,4-dimethylpentanamide was separated by chromatography Example 2a ¹H NMR (DMSO-d6 300 MHz): δ 8.34 (d, 1H), 7.48-7.35 (m, 3H), 7.23 (d, 1H), 5.07 (d, 1H), 4.61 (d, 1H), 3.34-3.54 (m, 5H), 2.31-2.20 (m, 1H), 2.17-2.08 (m, 1H), 1.08 (t, 2H), 0.83 (s, 9H).

LC-MS: $t_R$=1.87 min (LC-MS Method 4), m/z=378.2 [M+H]⁺.

SFC: $t_R$=1.71 min (SFC Method 18), ee %=96.0%.

Example 2b

¹H NMR (DMSO-d6 300 MHz): δ 8.39 (d, 1H), 7.46 (t, J=7.8 Hz, 5H), 7.35 (t, 2H), 7.23 (d, 3H), 5.06 (d, 1H), 4.63 (d, 1H), 3.56-3.52 (m, 3H), 3.49-3.43 (m, 2H), 2.29-2.25 (m, 1H), 2.19-2.08 (m, 1H), 1.07 (t, 2H), 0.82 (s, 9H).

LC-MS: $t_R$=1.87 min (LC-MS Method 4), m/z=378.2 [M+H]⁺.

SFC: $t_R$=1.82 min (SFC Method 18), ee %=99.1%.

Example 3a: N—((R)-2-(difluoromethoxy)-1-(3-(difluoromethoxy)phenyl)ethyl)-3-hydroxy-3-(1-(trifluoromethyl)cyclopropyl)propanamide

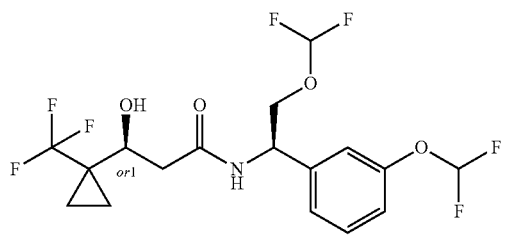 [SMILES: O=C(C[C@H](O)C1(C(F)(F)F)CC1)N[C@@H](COC(F)F)c1cccc(OC(F)F)c1]

and

Example 3b: N—((R)-2-(difluoromethoxy)-1-(3-(difluoromethoxy)phenyl)ethyl)-3-hydroxy-3-(1-(trifluoromethyl)cyclopropyl)propanamide

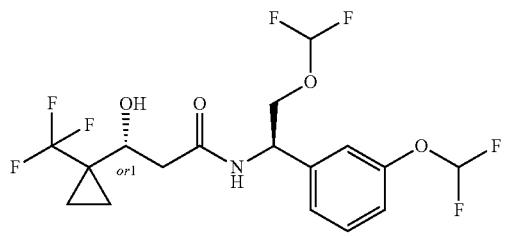 [SMILES: O=C(C[C@@H](O)C1(C(F)(F)F)CC1)N[C@@H](COC(F)F)c1cccc(OC(F)F)c1]

Step 1: Preparation of N—((R)-2-(difluoromethoxy)-1-(3-(difluoromethoxy)phenyl)ethyl)-3-hydroxy-3-(1-(trifluoro-methyl)cyclopropyl)propanamide

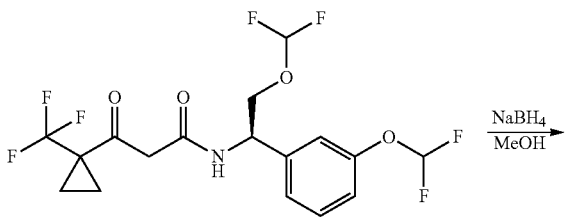

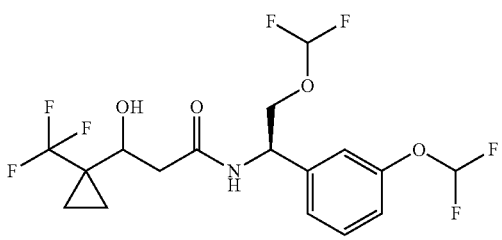

Prepared from Vc.

Step 2: Separation of (R)—N—((R)-2-(difluoromethoxy)-1-(3-(difluoromethoxy)phenyl)ethyl)-3-hydroxy-3-(1-(trifluoro-methyl)cyclopropyl)propanamide and (S)—N—((R)-2-(difluoromethoxy)-1-(3-(difluoromethoxy)phenyl)ethyl)-3-hydroxy-3-(1-(trifluoro-methyl)cyclopropyl)propanamide

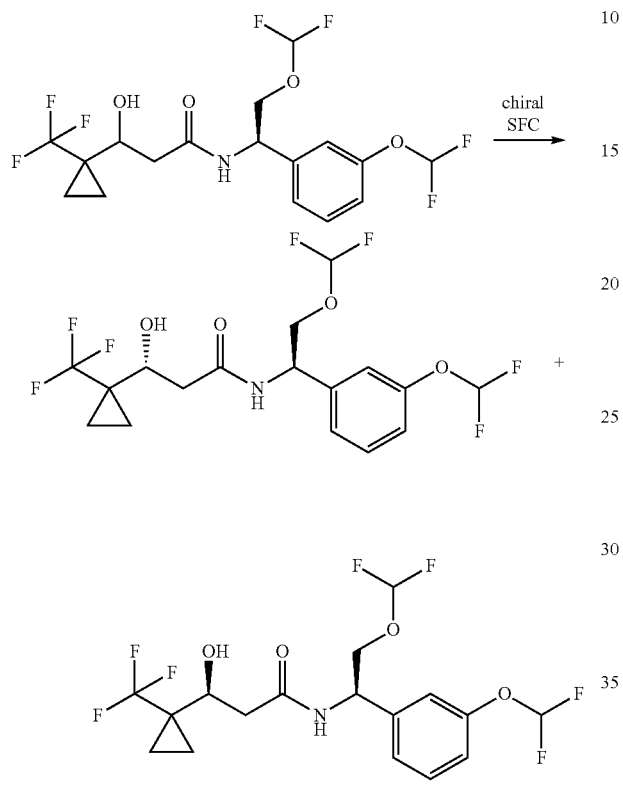

N—((R)-2-(difluoromethoxy)-1-(3-(difluoromethoxy)phenyl) ethyl)-3-hydroxy-3-(1-(trifluoromethyl)cyclopropyl)propanamide was separated by chiral SFC.

Example 3a

¹H NMR (CDCl₃ 400 MHz): δ 7.35 (t, 1H), 7.16 (d, 1H), 7.07-7.05 (m, 2H), 6.45 (t, 1H), 6.33 (s, 1H), 6.22 (t, 1H), 5.28-5.24 (m, 1H), 4.17-4.04 (m, 3H), 3.68 (s, 1H), 2.67 (dd, 1H), 2.55 (dd, 1H), 0.92-0.88 (m, 3H), 0.85-0.82 (m, 1H).

LC-MS: $t_R$=2.51 min (LCMS Method 1), m/z=434.1 [M+H]⁺.

SFC: $t_R$=1.95 min (SFC Method 3), ee %=100%.

Example 3b

¹H NMR (CDCl₃ 400 MHz): δ 7.36 (t, 1H), 7.16 (d, 1H), 7.06 (m, 2H), 6.50 (t, 1H), 6.38 (d, 1H), 6.21 (t, 1H), 5.27-5.23 (m, 1H), 4.13-4.04 (m, 3H), 3.76 (d, 1H), 2.67-2.56 (m, 2H), 0.98-0.87 (m, 4H).

LC-MS: $t_R$=2.51 min (LCMS Method 1), m/z=434.1 [M+H]⁺.

SFC: $t_R$=1.58 min (SFC Method 3), ee %=90.0%.

Example 4a: N—((R)-2-(difluoromethoxy)-1-(3-(trifluoromethoxy)phenyl)ethyl)-3-hydroxy-3-(1-(trifluoromethyl)cyclopropyl)propanamide

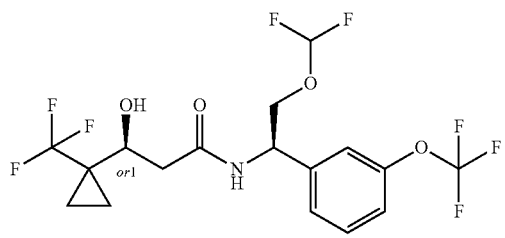 [SMILES: O=C(C[C@H](O)C1(C(F)(F)F)CC1)N[C@@H](COC(F)F)c1cccc(OC(F)(F)F)c1]

and

Example 4b: N—((R)-2-(difluoromethoxy)-1-(3-(trifluoromethoxy)phenyl)ethyl)-3-hydroxy-3-(1-(trifluoromethyl)cyclopropyl)propanamide

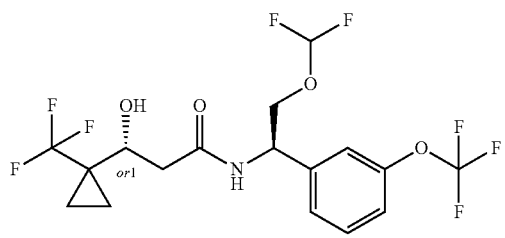 [SMILES: O=C(C[C@@H](O)C1(C(F)(F)F)CC1)N[C@@H](COC(F)F)c1cccc(OC(F)(F)F)c1]

Step 1: Preparation of N—((R)-2-(difluoromethoxy)-1-(3-(trifluoromethoxy)phenyl)ethyl)-3-hydroxy-3-(1-(trifluoro-methyl)cyclopropyl)propanamide

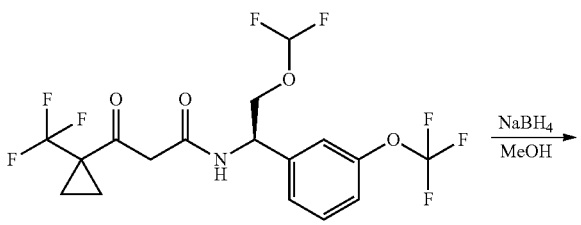

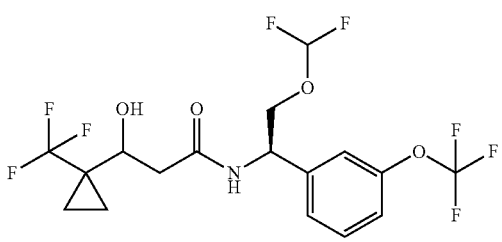

Prepared from Vd.

Step 2: Separation of (R)—N—((R)-2-(difluoromethoxy)-1-(3-(trifluoromethoxy)phenyl)ethyl)-3-hydroxy-3-(1-(trifluoromethyl)cyclopropyl)propanamide and (S)—N—((R)-2-(difluoromethoxy)-1-(3-(trifluoromethoxy)phenyl) ethyl)-3-hydroxy-3-(1-(trifluoromethyl)cyclopropyl) propanamide

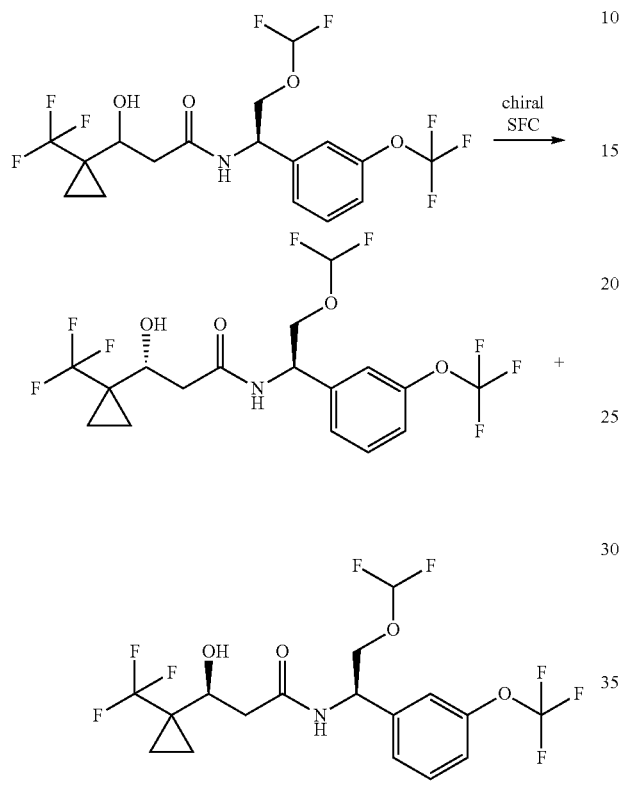

N—((R)-2-(difluoromethoxy)-1-(3-(trifluoromethoxy)phenyl)ethyl)-3-hydroxy-3-(1-(trifluoromethyl) cyclopropyl)propanamide was separated by chiral SFC.

Example 4a $^1$H NMR (CDCl$_3$ 400 MHz): δ 7.41 (t, 1H), 7.27 (s, 1H), 7.18 (m, 2H), 6.41 (s, 1H), 6.23 (t, 1H), 5.30 (s, 1H), 4.16-4.06 (m, 3H), 3.74 (s, 1H), 2.69-2.56 (m, 2H), 1.00-0.90 (m, 4H).

LC-MS: $t_R$=2.53 min (LCMS Method 2), m/z=452.1 [M+H]$^+$.

SFC: $t_R$=1.21 min (SFC Method 7), ee %=100%.

Example 4b $^1$H NMR (CDCl$_3$ 400 MHz): δ 7.40 (t, 1H), 7.27 (s, 1H), 7.18 (m, 2H), 6.42 (s, 1H), 6.24 (t, 1H), 5.30 (s, 1H), 4.19-4.05 (m, 3H), 3.69 (s, 1H), 2.71-2.55 (m, 2H), 0.93-0.83 (m, 4H).

LC-MS: $t_R$=2.63 min (LCMS Method 1), m/z=452.1 [M+H]$^+$.

SFC: $t_R$=1.57 min (SFC Method 7), ee %=99.8%.

Example 5a: 3-(3,3-difluorocyclobutyl)-N—((R)-2-(difluoromethoxy)-1-(3-(difluoromethoxy)phenyl)ethyl)-3-hydroxypropanamide

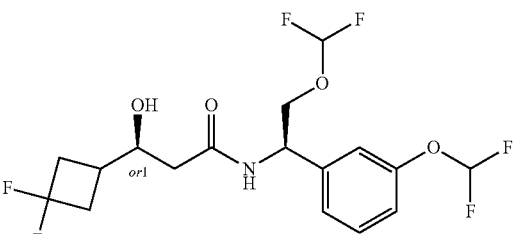

and

Example 5b: 3-(3,3-difluorocyclobutyl)-N—((R)-2-(difluoromethoxy)-1-(3-(difluoromethoxy)phenyl)ethyl)-3-hydroxypropanamide

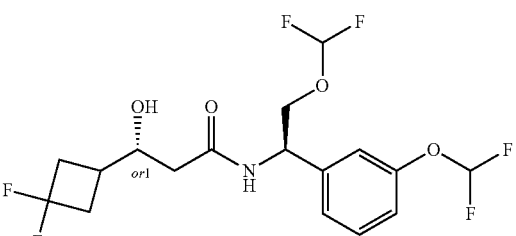

Step 1: Preparation of (R)-3-(3,3-difluorocyclobutyl)-N-(2-(difluoromethoxy)-1-(3-(difluoromethoxy) phenyl) ethyl)-3-oxopropanamide

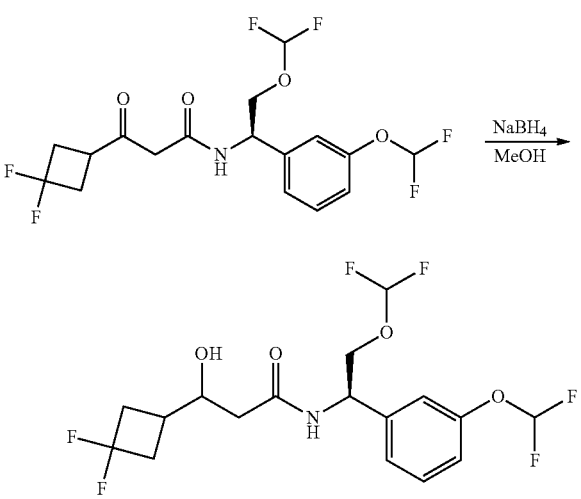 [SMILES: "MeOH" ; O=C(CC(=O)C1CC(F)(F)C1)N[C@@H](COC(F)F)c1cccc(OC(F)F)c1 ; "NaBH4" ; O=C(CC(O)C1CC(F)(F)C1)N[C@@H](COC(F)F)c1cccc(OC(F)F)c1]

Prepared from Ve.

Step 2: Separation of (R)-3-(3,3-difluorocyclobutyl)-N—((R)-2-(difluoromethoxy)-1-(3-(difluoromethoxy)phenyl)ethyl)-3-hydroxypropanamide and (S)-3-(3,3-difluorocyclobutyl)-N—((R)-2-(difluoromethoxy)-1-(3-(difluoromethoxy)phenyl)ethyl)-3-hydroxypropanamide

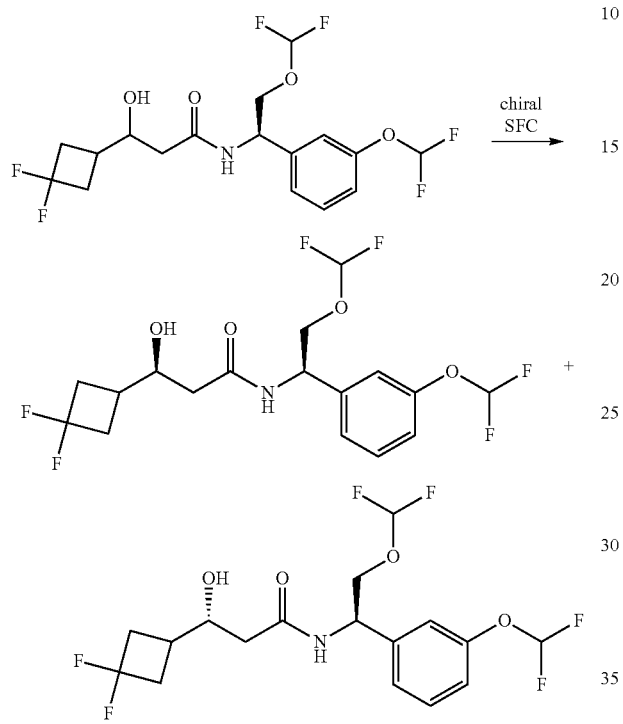

(R)-3-(3,3-difluorocyclobutyl)-N-(2-(trifluoromethoxy)-1-(3-(difluoromethoxy)phenyl)ethyl)-3-oxopropanamide was separated by chiral SFC.

Example 5a $^1$H NMR (CDCl$_3$ 400 MHz): δ 7.37 (t, 1H), 7.17 (d, 1H), 7.09-7.07 (m, 2H), 6.51 (t, 1H), 6.32 (m, 1H), 6.13 (t, 1H), 5.30-5.25 (m, 1H), 4.18-4.14 (m, 1H), 4.10-4.06 (m, 1H), 4.00-3.96 (m, 1H), 3.64 (d, 1H), 2.59-2.55 (m, 3H), 2.45-2.35 (m, 2H), 2.34-2.26 (m, 1H), 2.21-2.08 (m, 1H).

LC-MS: t$_R$=2.74 min (LCMS Method 1), m/z=416.1 [M+H]$^+$.

SFC: t$_R$=2.49 min (SFC Method 4), ee %=97.7%.

Example 5b $^1$H NMR (CDCl$_3$ 400 MHz): δ 7.37 (t, 1H), 7.17 (d, 1H), 7.08-7.07 (m, 2H), 6.51 (t, 1H), 6.32 (m, 1H), 6.23 (t, 1H), 5.30-5.26 (m, 1H), 4.18-4.15 (m, 1H), 4.11-4.07 (m, 1H), 4.02-3.98 (m, 1H), 2.64-2.51 (m, 3H), 2.45-2.36 (m, 2H), 2.33-2.25 (m, 1H), 2.21-2.16 (m, 1H).

LC-MS: t$_R$=2.73 min (LCMS Method 1), m/z=416.1 [M+H]$^+$.

SFC: t$_R$=2.59 min (SFC Method 4), ee %=96.1%.

Example 6a: 3-(3,3-difluorocyclobutyl)-N—((R)-2-(difluoromethoxy)-1-(3-(trifluoromethoxy)phenyl)ethyl)-3-hydroxypropanamide

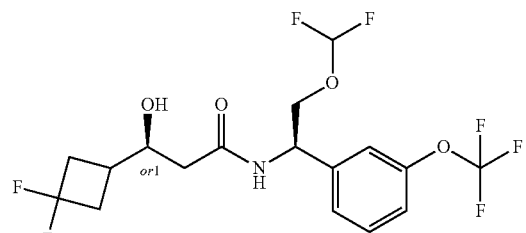

and

Example 6b: 3-(3,3-difluorocyclobutyl)-N—((R)-2-(difluoromethoxy)-1-(3-(trifluoromethoxy)phenyl)ethyl)-3-hydroxypropanamide

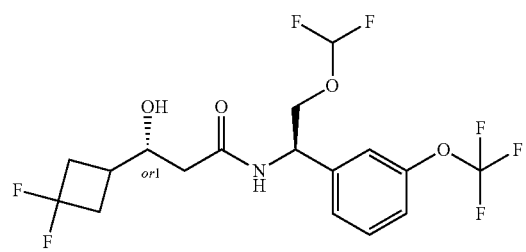 [SMILES: O=C(C[C@@H](O)C1CC(F)(F)C1)N[C@@H](COC(F)F)c1cccc(OC(F)(F)F)c1]

Step 1: Preparation of (R)-3-(3,3-difluorocyclobutyl)-N-(2-(difluoromethoxy)-1-(3-(trifluoromethoxy) phenyl) ethyl)-3-oxopropanamide

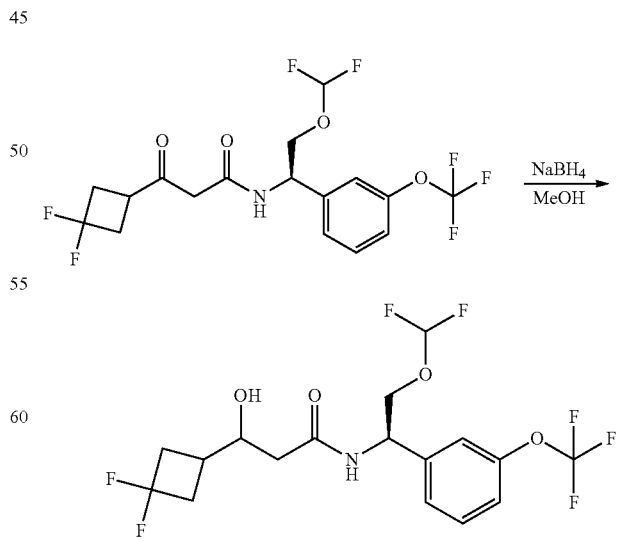

Prepared from Vf.

Step 2: Separation of (R)-3-(3,3-difluorocyclobutyl)-N—((R)-2-(difluoromethoxy)-1-(3-(trifluoromethoxy)phenyl) ethyl)-3-hydroxypropanamide and (S)-3-(3,3-difluorocyclobutyl)-N—((R)-2-(difluoromethoxy)-1-(3 (trifluoromethoxy)phenyl) ethyl)-3-hydroxypropanamide

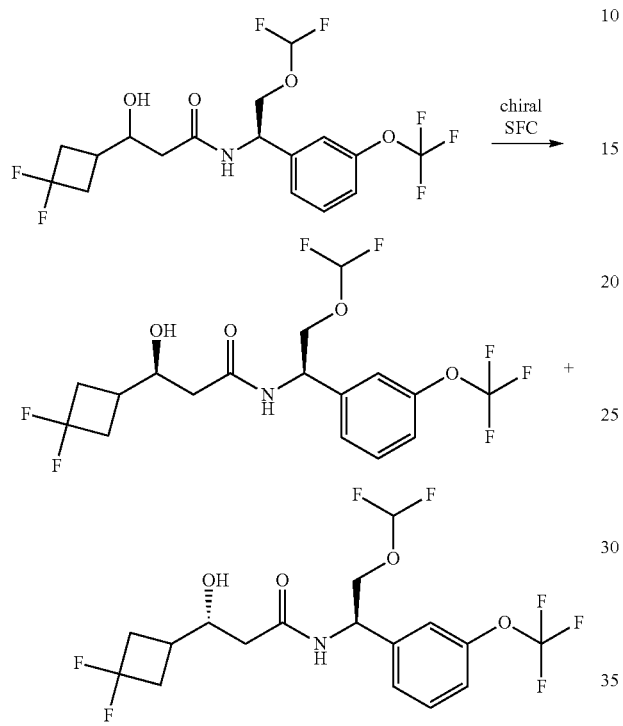

(R)-3-(3,3-difluorocyclobutyl)-N-(2-(difluoromethoxy)-1-(3-(trifluoromethoxy)phenyl)ethyl)-3-oxopropanamide was separated by chiral SFC.

Example 6a

¹H NMR (CDCl₃ 400 MHz): δ 7.41 (t, 1H), 7.26 (d, 1H), 7.19 (d, 2H), 6.38 (d, 1H), 6.24 (t, 1H), 5.33-5.28 (m, 1H), 4.20-4.16 (m, 1H), 4.13-4.10 (m, 1H), 4.01-4.00 (s, 1H), 3.56 (d, 2H), 2.61-2.54 (m, 3H), 2.44-2.39 (m, 2H), 2.39-2.32 (m, 1H), 2.18 (m, 1H).

LC-MS: $t_R$=2.53 min (LCMS Method 1), m/z=434.0 [M+H]⁺.

SFC: $t_R$=1.62 min (SFC Method 5), ee %=92.9%.

Example 6b

¹H NMR (CDCl₃ 400 MHz): δ 7.42 (t, 1H), 7.26 (d, 1H), 7.20-7.18 (m, 2H), 6.34 (d, 1H), 6.24 (t, 1H), 5.33-5.28 (m, 1H), 4.20-4.16 (m, 1H), 4.13-4.00 (m, 1H), 4.00 (m, 1H), 3.61 (s, 1H), 2.61-2.57 (m, 3H), 2.43-2.39 (m, 2H), 2.39-2.32 (m, 1H), 2.20 (m, 1H).

LC-MS: $t_R$=2.54 min (LCMS Method 1), m/z=434.0 [M+H]⁺.

SFC: $t_R$=1.71 min (SFC Method 5), ee %=97.9%.

Example 7a: 3-(3,3-difluorocyclobutyl)-N—((S)-1-(3-(difluoromethoxy)phenyl)butyl)-3-hydroxypropanamide

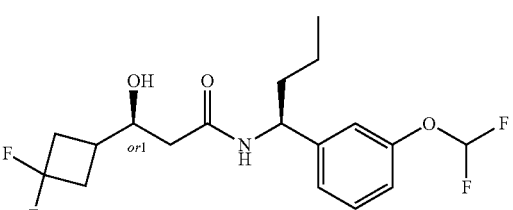

and

Example 7b: 3-(3,3-difluorocyclobutyl)-N—((S)-1-(3-(difluoromethoxy)phenyl)butyl)-3-hydroxypropanamide

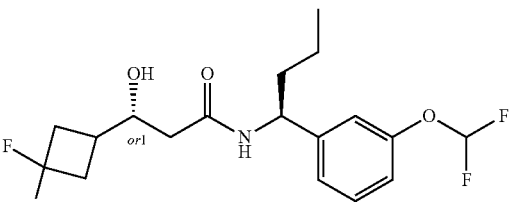

Step 1: Preparation of 3-(3,3-difluorocyclobutyl)-N—((S)-1-(3-(difluoromethoxy)phenyl)butyl)-3-hydroxypropanamide

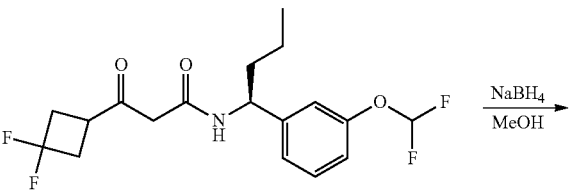

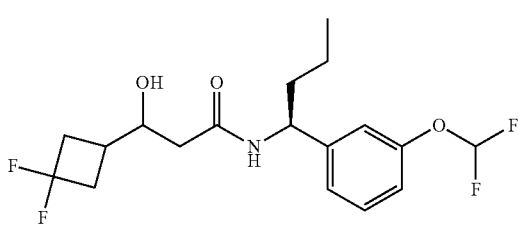

Prepared from Vg

Step 2: Separation of (S)-3-(3,3-difluorocyclobutyl)-N—((S)-1-(3-(difluoromethoxy)phenyl)butyl)-3-hydroxypropanamide and (R)-3-(3,3-difluorocyclobutyl)-N—((S)-1-(3-(difluoromethoxy)phenyl)butyl)-3-hydroxypropanamide

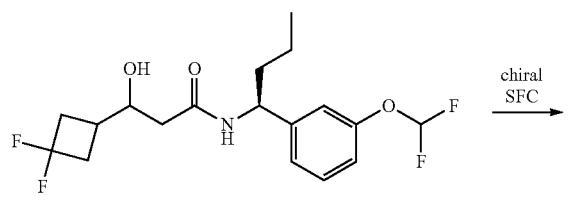

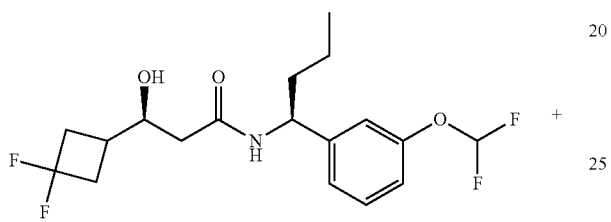

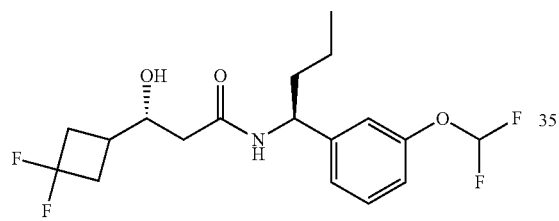

3-(3,3-difluorocyclobutyl)-N—((S)-1-(3-(difluoromethoxy) phenyl)butyl)-3-hydroxypropanamide was separated by chiral SFC.

Example 7a

¹H NMR (CDCl₃ 400 MHz): δ 7.32 (t, 1H), 7.11 (d, 1H), 7.01-7.00 (m, 2H), 6.49 (t, 1H), 5.85 (d, 1H), 4.93 (q, 1H), 3.94-3.91 (m, 1H), 3.81 (d, 1H), 2.56-2.21 (m, 7H), 1.74-1.69 (m, 2H), 1.33-1.28 (m, 2H), 0.91 (t, 3H).

LC-MS: $t_R$=2.41 min (LC-MS Method 1), m/z=378.0 [M+H]⁺.

SFC: $t_R$=2.37 min (SFC method 6), ee %=92.4%

Example 7b

¹H NMR (CDCl₃ 400 MHz): δ 7.31 (t, 1H), 7.10 (d, 1H), 7.01-7.00 (m, 2H), 6.49 (t, 1H), 5.86 (d, 1H), 4.93 (q, 1H), 3.96-3.92 (m, 1H), 3.77 (d, 1H), 2.54-2.14 (m, 7H), 1.74-1.70 (m, 2H), 1.33-1.28 (m, 2H), 0.91 (t, 3H).

LC-MS: $t_R$=2.45 min (LC-MS Method 1), m/z=378.0 [M+H]⁺.

SFC: $t_R$=2.49 min (SFC Method 6), ee %=99.5%

Example 8a: N—((R)-2-(difluoromethoxy)-1-(3-(difluoromethoxy)phenyl)ethyl)-3-(1-ethylcyclopropyl)-3-hydroxypropanamide

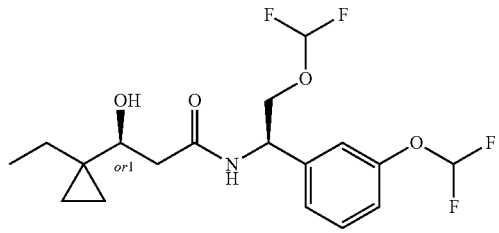 [SMILES: CCC1([C@@H](O)CC(=O)N[C@@H](COC(F)F)c2cccc(OC(F)F)c2)CC1]

and

Example 8b: N—((R)-2-(difluoromethoxy)-1-(3-(difluoromethoxy)phenyl)ethyl)-3-(1-ethylcyclopropyl)-3-hydroxypropanamide

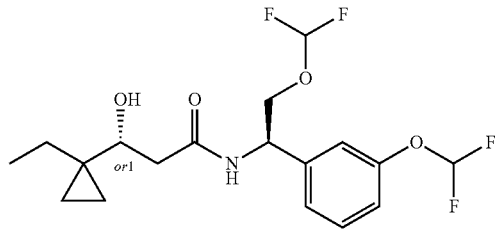 [SMILES: CCC1([C@H](O)CC(=O)N[C@@H](COC(F)F)c2cccc(OC(F)F)c2)CC1]

Step 1: Preparation of N—((R)-2-(difluoromethoxy)-1-(3-(difluoromethoxy)phenyl)ethyl)-3-(1-ethylcyclopropyl)-3-hydroxypropanamide Prepared from Vh Step 2: Separation of (S)—N—((R)-2-(difluoromethoxy)-1-(3-(difluoromethoxy)phenyl)ethyl)-3-(1-ethylcyclopropyl)-3-hydroxypropanamide and (R)—N—((R)-2-(difluoromethoxy)-1-(3-(difluoromethoxy)phenyl) ethyl)-3-(1-ethylcyclopropyl)-3-hydroxypropanamide

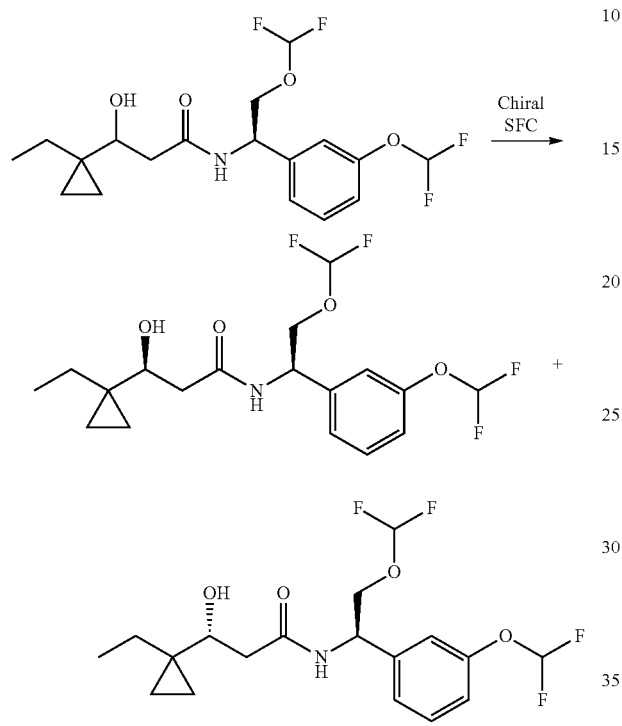

N—((R)-2-(difluoromethoxy)-1-(3-(difluoromethoxy)phenyl)ethyl)-3-(1-ethylcyclopropyl)-3-hydroxypropanamide was separated by chiral SFC Example 8a $^1$H NMR (CDCl$_3$ 400 MHz): δ 7.28 (t, 1H), 7.11 (d, 1H), 7.03 (s, 1H), 6.98 (d, 1H), 6.66 (d, 1H), 6.44 (t, 1H), 6.14 (t, 1H), 5.24-5.19 (m, 1H), 4.10-4.02 (m, 2H), 3.47-3.44 (m, 1H), 2.57 (d, 1H), 2.50-2.41 (m, 2H), 1.53-1.48 (m, 2H), 1.34-1.31 (m, 1H), 0.83-0.80 (m, 3H), 0.38-0.29 (m, 4H).

LC-MS: t$_R$=2.38 min (LCMS Method 1), m/z=394.0 [M+H]$^+$.

SFC: t$_R$=2.38 min (SFC Method 1), ee %=99.4%

Example 8b $^1$H NMR (CDCl$_3$ 400 MHz): δ 7.29 (t, 1H), 7.11 (d, 1H), 7.01-6.99 (m, 2H), 6.67 (d, 1H), 6.44 (t, 1H), 6.15 (t, 1H), 5.24-5.19 (m, 1H), 4.10-4.00 (m, 2H), 3.49-3.47 (d, 1H), 2.64 (d, 1H), 2.49-2.41 (m, 2H), 1.53-1.48 (m, 2H), 1.34-1.31 (m, 1H), 0.83-0.80 (m, 3H), 0.39-0.29 (m, 4H).

LC-MS: t$_R$=2.38 min (LCMS Method 1), m/z=394.0 [M+H]$^+$.

SFC: t=2.60 min (SFC Method 1), ee %=98.7%

Example 9a: N—((R)-2-(difluoromethoxy)-1-(3-(difluoromethoxy)phenyl)ethyl)-3-(1-fluorocyclopropyl)-3-hydroxybutanamide

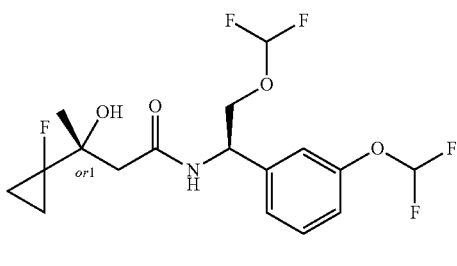 [SMILES: C[C@@](O)(CC(=O)N[C@@H](COC(F)F)c1cccc(OC(F)F)c1)C1(F)CC1]

and

Example 9b: N—((R)-2-(difluoromethoxy)-1-(3-(difluoromethoxy)phenyl)ethyl)-3-(1-fluorocyclopropyl)-3-hydroxybutanamide

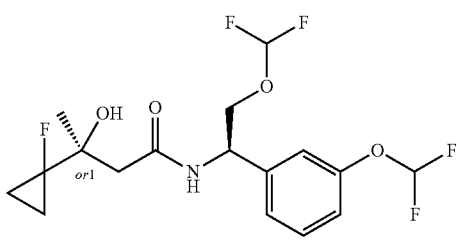 [SMILES: C[C@](O)(CC(=O)N[C@@H](COC(F)F)c1cccc(OC(F)F)c1)C1(F)CC1]

Step 1: Preparation of N—((R)-2-(difluoromethoxy)-1-(3-(difluoromethoxy)phenyl)ethyl)-3-(1-fluorocyclopropyl)-3-hydroxybutanamide

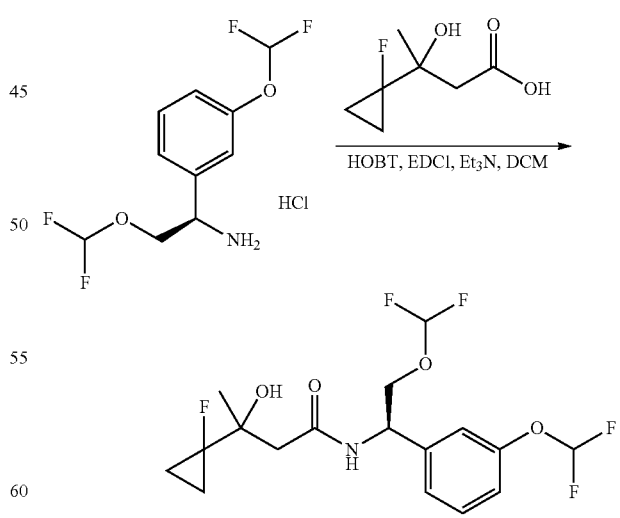

To a solution of (R)-2-(difluoromethoxy)-1-(3-(difluoromethoxy)phenyl)ethan-1-amine hydrochloride (IIa) (400 mg) and 3-(1-fluorocyclopropyl)-3-hydroxy-butanoic acid (IIIc) (307 mg) in DCM (20 mL) was added N-hydroxybenzotriazole (HOBt) (213 mg), 1-Ethyl-3-(3-dimethylaminopropyl)carbodiimide (EDCI) (363 mg) and Et₃N (320 mg). The mixture was stirred at 25° C. for 16 hours and then diluted with water (10 mL), and extracted with EtOAc (20 mL×3). The combined organic extracts were dried over Na₂SO₄, filtered and concentrated. The residue was purified by basic preparative HPLC to afford N—((R)-2-(difluoromethoxy)-1-(3-(difluoromethoxy)phenyl)ethyl)-3-(1-fluorocyclopropyl)-3-hydroxybutanamide (250 mg).

Step 2: Separation of (R)—N—((R)-2-(difluoromethoxy)-1-(3-(difluoromethoxy)phenyl)ethyl)-3-(1-fluorocyclopropyl)-3-hydroxybutanamide and (S)—N—((R)-2-(difluoromethoxy)-1-(3-(difluoromethoxy)phenyl) ethyl)-3-(1-fluorocyclopropyl)-3-hydroxybutanamide

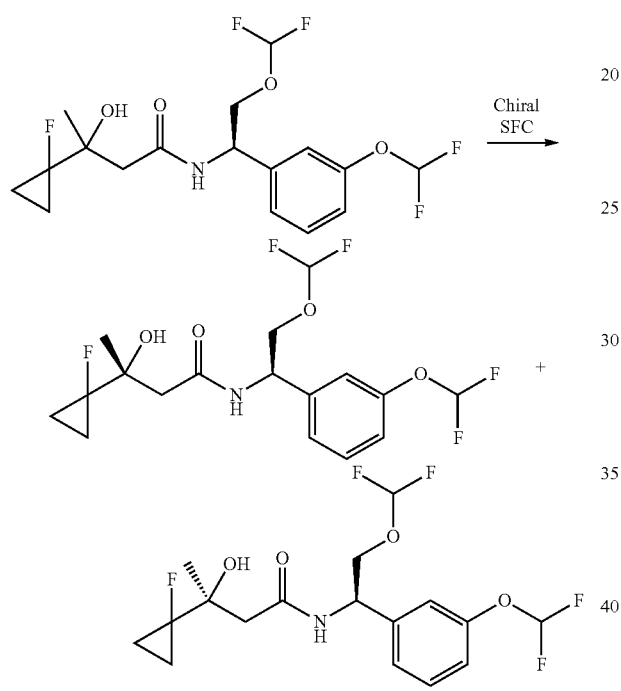

N—((R)-2-(difluoromethoxy)-1-(3-(difluoromethoxy)phenyl)ethyl)-3-(1-fluorocyclopropyl)-3-hydroxybutanamide was separated by chiral SFC.

Example 9a

¹H NMR (CDCl₃ 400 MHz): δ 7.38 (t, 1H), 7.20 (d, 1H), 7.10 (m, 2H), 6.52 (t, 1H), 6.39 (d, 1H), 6.25 (t, 1H), 5.31 (m, 1H), 4.80 (s, 1H), 4.15 (m, 2H), 2.71 (dd, 1H), 2.54 (dd, 1H), 1.36 (s, 3H), 0.85-0.55 (m, 4H).

LC-MS: $t_R$=2.48 min (LCMS Method 1), m/z=398.2 [M+H]⁺.

SFC: $t_R$=2.46 min (SFC Method 12), ee %=100%.

Example 9b

¹H NMR (CDCl³ 400 MHz): δ 7.39 (t, 1H), 7.19 (d, 1H), 7.10-7.08 (m, 2H), 6.52 (t, 1H), 6.42 (m, 1H), 6.24 (t, 1H), 5.33-5.28 (m, 1H), 4.71 (s, 1H), 4.19-4.10 (m, 2H), 2.72 (d, 1H), 2.52 (d, 1H), 1.36 (s, 3H), 0.99-0.85 (m, 4H).

LC-MS: $t_R$=2.47 min (LCMS Method 1), m/z=398.1 [M+H]⁺.

SFC: $t_R$=2.65 min (SFC Method 12), ee %=98.8%.

The following examples were prepared by similar methodology as described for Example 9a and Example 9b, using the relevant intermediates:

Example 10a: N—((R)-2-(difluoromethoxy)-1-(3-(trifluoromethoxy)phenyl)ethyl)-3-(1-fluorocyclopropyl)-3-hydroxybutanamide

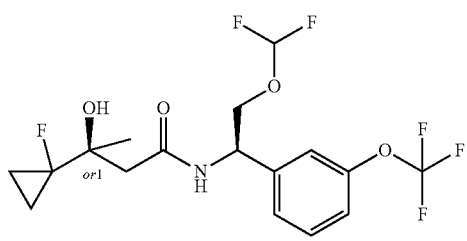 [SMILES: C[C@](O)(CC(=O)N[C@@H](COC(F)F)c1cccc(OC(F)(F)F)c1)C1(F)CC1]

And

Example 10b: N—((R)-2-(difluoromethoxy)-1-(3-(trifluoromethoxy)phenyl)ethyl)-3-(1-fluorocyclopropyl)-3-hydroxybutanamide

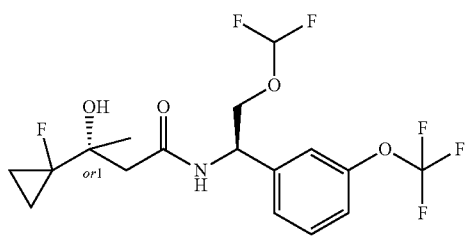 [SMILES: C[C@@](O)(CC(=O)N[C@@H](COC(F)F)c1cccc(OC(F)(F)F)c1)C1(F)CC1]

Step 1: Preparation of N—((R)-2-(difluoromethoxy)-1-(3-(trifluoromethoxy)phenyl)ethyl)-3-(1-fluorocyclopropyl)-3-hydroxybutanamide

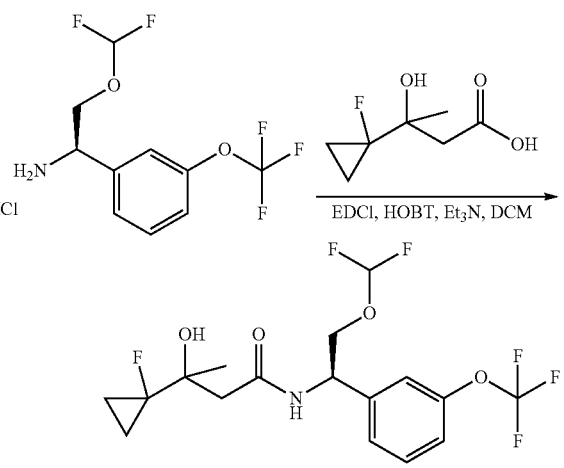

Prepared from IIb and IIIc

Step 2: Separation of (S)—N—((R)-2-(difluoromethoxy)-1-(3-(trifluoromethoxy)phenyl)ethyl)-3-(1-fluorocyclopropyl)-3-hydroxybutanamide and (R)—N—((R)-2-(difluoromethoxy)-1-(3-(trifluoromethoxy)phenyl) ethyl)-3-(1-fluorocyclopropyl)-3-hydroxybutanamide

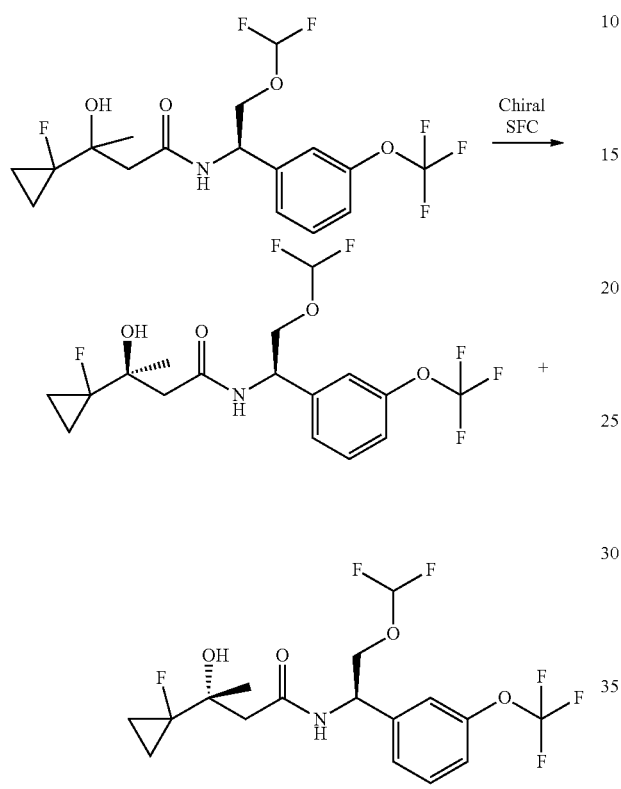

N—((R)-2-(difluoromethoxy)-1-(3-(trifluoromethoxy) phenyl)ethyl)-3-(1-fluorocyclopropyl)-3-hydroxybutanamide was separated using chiral SFC

Example 10a

1H NMR (CDCl3 400 MHz): δ 7.48 (t, 1H), 7.35 (d, 1H), 7.27-7.25 (m, 2H), 6.64 (d, 1H), 6.31 (t, 1H), 5.40-5.38 (m, 1H), 4.86 (s, 1H), 4.26-4.18 (m, 2H), 2.78 (d, 1H), 2.60 (d, 1H), 1.42 (s, 3H), 0.86-0.57 (m, 4H).

LC-MS: tR=2.64 min (LCMS Method 1), m/z=416.2 [M+H]$^+$.

SFC: tR=2.38 min (SFC Method 2), ee %=100%.

Example 10b

1H NMR (CDCl3 400 MHz): δ 7.42 (t, 1H), 7.29 (m, 1H), 7.20-7.19 (m, 2H), 6.44-6.06 (m, 2H), 5.35-5.31 (m, 1H), 4.67 (s, 1H), 4.20-4.12 (m, 2H), 2.73 (dd, 1H), 2.53 (dd, 1H), 1.36 (s, 3H), 0.99-0.86 (m, 4H).

LC-MS: tR=2.659 min (LCMS Method 1), m/z=416.2 [M+H]$^+$.

SFC: tR=2.561 min (SFC Method 6), ee %=95.9%.

Example 11a: 3-cyclopropyl-N—((R)-2-(difluoromethoxy)-1-(3-(trifluoromethoxy)phenyl) ethyl)-3-hydroxybutanamide

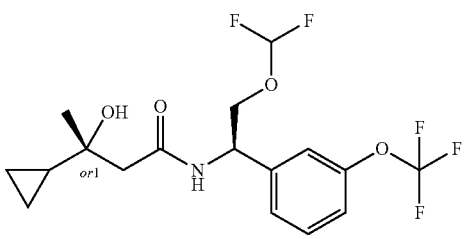 [SMILES: C[C@@](O)(CC(=O)N[C@@H](COC(F)F)c1cccc(OC(F)(F)F)c1)C1CC1]

and

Example 11b: 3-cyclopropyl-N—((R)-2-(difluoromethoxy)-1-(3-(trifluoromethoxy)phenyl)ethyl)-3-hydroxybutanamide

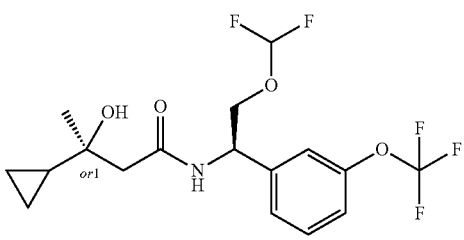 [SMILES: C[C@](O)(CC(=O)N[C@@H](COC(F)F)c1cccc(OC(F)(F)F)c1)C1CC1]

Step 1: Preparation of 3-cyclopropyl-N—((R)-2-(difluoromethoxy)-1-(3-(trifluoromethoxy)phenyl) ethyl)-3-hydroxybutanamide

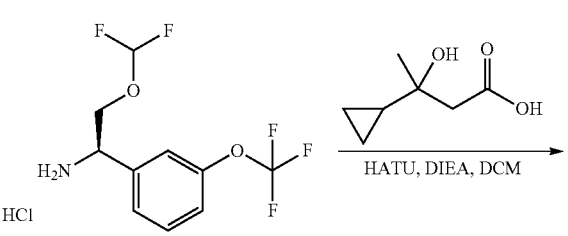

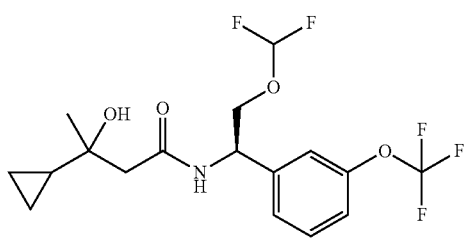

Prepared from IIb and IIId

Step 2: Separation of (R)-3-cyclopropyl-N—((R)-2-(difluoromethoxy)-1-(3-(trifluoromethoxy)phenyl)ethyl)-3-hydroxybutanamide and (S)-3-cyclopropyl-N—((R)-2-(difluoromethoxy)-1-(3-(trifluoromethoxy) phenyl)ethyl)-3-hydroxybutanamide Example 12a: N—((R)-2-(difluoromethoxy)-1-(3-(difluoromethoxy)phenyl)ethyl)-5,5,5-trifluoro-3-hydroxy-3-methylpentanamide

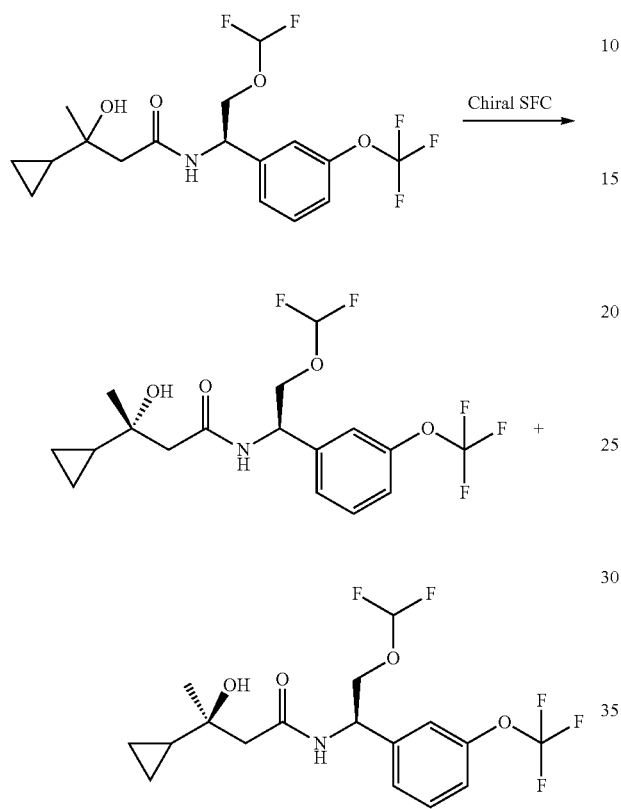

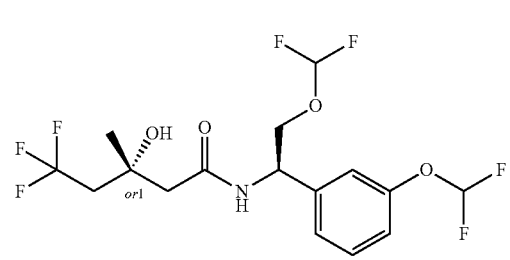 [SMILES: C[C@@](O)(CC(=O)N[C@@H](COC(F)F)c1cccc(OC(F)F)c1)CC(F)(F)F]

And

Example 12b: N—((R)-2-(difluoromethoxy)-1-(3-(difluoromethoxy)phenyl)ethyl)-5,5,5-trifluoro-3-hydroxy-3-methylpentanamide

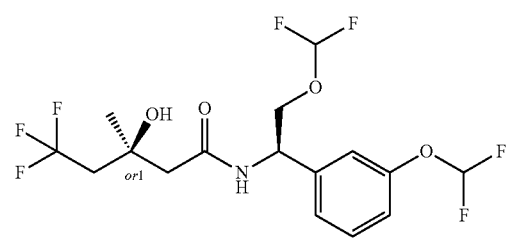 [SMILES: C[C@](O)(CC(=O)N[C@@H](COC(F)F)c1cccc(OC(F)F)c1)CC(F)(F)F]

3-cyclopropyl-N—((R)-2-(difluoromethoxy)-1-(3-(trifluoromethoxy)phenyl)ethyl)-3-hydroxybutanamide was separated by chiral SFC Step 1: Preparation of N—((R)-2-(difluoromethoxy)-1-(3-(difluoromethoxy)phenyl)ethyl)-5,5,5-trifluoro-3-hydroxy-3-methylpentanamide

Example 11a $^1$H NMR (CDCl$_3$ 400 MHz): δ 7.38 (t, 1H), 7.26 (d, 1H), 7.17-7.15 (m, 2H), 6.72 (d, 1H), 6.21 (t, 1H), 5.35-5.31 (m, 1H), 4.17-4.09 (m, 2H), 3.36 (s, 1H), 2.52-2.42 (m, 2H), 1.18 (s, 3H), 0.90-0.88 (m, 1H), 0.43-0.34 (m, 4H).

LC-MS: t$_R$=2.42 min (LCMS Method 1), m/z=420.1 [M+Na]+.

SFC: t$_R$=2.17 min (SFC Method 13), ee %=100%.

Example 11b $^1$H NMR (CDCl$_3$ 400 MHz): δ 7.39 (t, 1H), 7.29-7.20 (m, 1H), 7.21-7.16 (m, 2H), 6.74 (d, 1H), 6.23 (t, 1H), 5.36-5.32 (m, 1H), 4.19-4.10 (m, 2H), 3.40 (s, 1H), 2.49 (s, 2H), 1.18 (s, 3H), 0.90-0.87 (m, 1H), 0.41-0.27 (m, 4H).

LC-MS: t$_R$=2.95 min (LCMS Method 1), m/z=420.1 [M+Na]+.

SFC: t$_R$=2.48 min (SFC Method 13), ee %=100%.

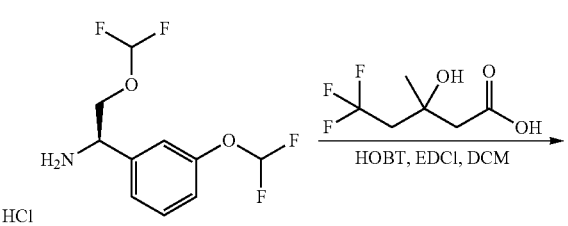

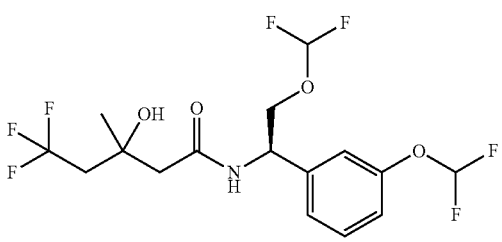

Prepared from IIa and IIIe

Step 2: Separation of (R)—N—((R)-2-(difluoromethoxy)-1-(3-(difluoromethoxy)phenyl)ethyl)-5,5,5-trifluoro-3-hydroxy-3-methylpentanamide and (S)—N—((R)-2-(difluoromethoxy)-1-(3-(difluoromethoxy)phenyl)ethyl)-5,5,5-trifluoro-3-hydroxy-3-methylpentanamide

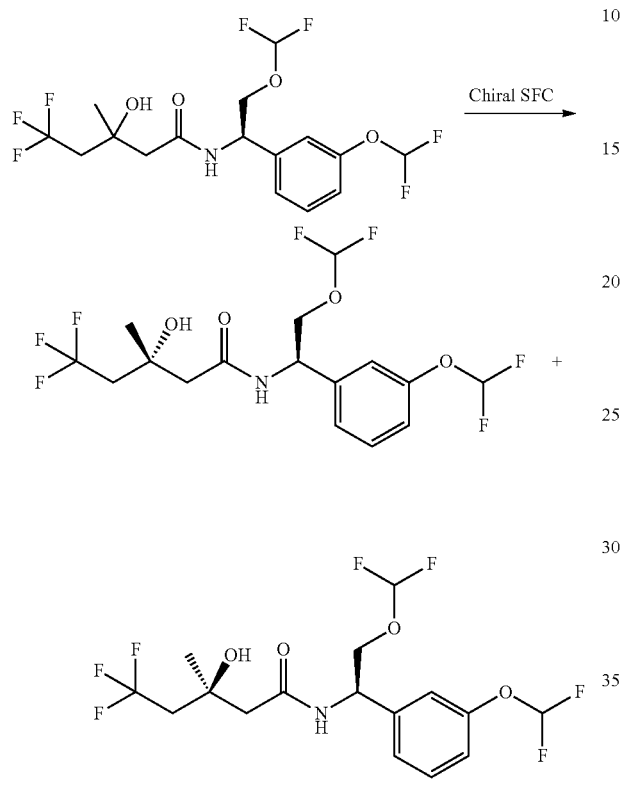

N—((R)-2-(difluoromethoxy)-1-(3-(difluoromethoxy)phenyl) ethyl)-5,5,5-trifluoro-3-hydroxy-3-methylpentanamide was separated by chiral SFC

Example 12a $^1$H NMR (CDCl$_3$ 400 MHz): δ 7.38 (t, 1H), 7.17 (d, 1H), 7.10-7.08 (m, 2H), 6.51 (t, 1H), 6.37 (d, 1H), 6.25 (t, 1H), 5.32-5.27 (m, 1H), 4.68 (s, 1H), 4.18 (dd, 1H), 2.52 (dd, 1H), 2.61-2.52 (m, 2H), 2.47-2.41 (m, 2H), 1.40 (s, 3H).

LC-MS: t$_R$=2.52 min (LCMS Method 1), m/z=422.1 [M+H]$^+$.

SFC: t$_R$=1.10 min (SFC Method 14), ee %=100%.

Example 12b $^1$H NMR (CDCl$_3$ 400 MHz): δ 7.39 (t, 1H), 7.18 (d, 1H), 7.10-7.08 (m, 2H), 6.52 (t, 1H), 6.36 (d, 1H), 6.24 (t, 1H), 5.33-5.29 (m, 1H), 4.68 (s, 1H), 4.18 (dd, 1H), 2.52 (dd, 1H), 2.61-2.42 (m, 4H), 1.39 (s, 3H).

LC-MS: t$_R$=2.52 min (LCMS Method 1), m/z=422.1 [M+H]$^+$.

SFC: t$_R$=1.24 min (SFC Method 14), ee %=95.8%.

Example 13a: N—((R)-2-(difluoromethoxy)-1-(3-(difluoromethoxy)phenyl)ethyl)-3-hydroxy-3,5-dimethylhexanamide

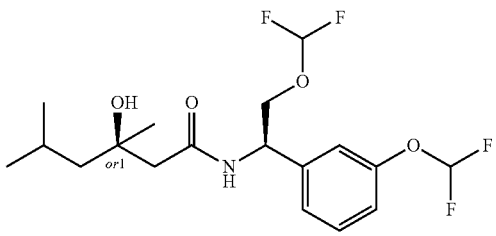 [SMILES: CC(C)C[C@@](C)(O)CC(=O)N[C@@H](COC(F)F)c1cccc(OC(F)F)c1]

And

Example 13b: N—((R)-2-(difluoromethoxy)-1-(3-(difluoromethoxy)phenyl)ethyl)-3-hydroxy-3,5-dimethylhexanamide

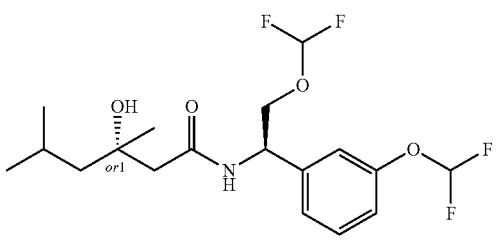

Step 1: Preparation of N—((R)-2-(difluoromethoxy)-1-(3-(difluoromethoxy)phenyl)ethyl)-3-hydroxy-3,5-dimethylhexanamide

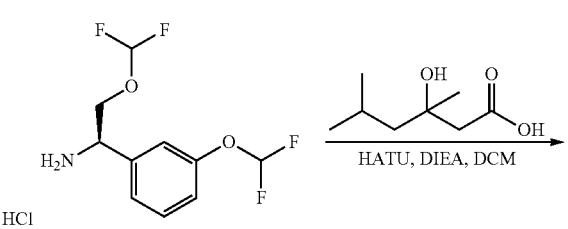

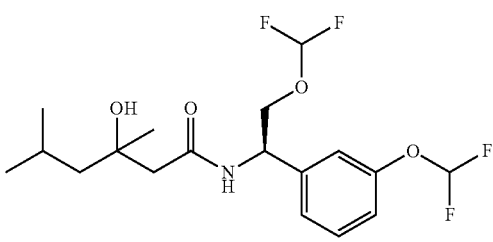 [SMILES: CC(C)C[C@](C)(O)CC(=O)N[C@@H](COC(F)F)c1cccc(OC(F)F)c1]

Prepared from IIa and IIIg

Step 2: Separation of (R)—N—((R)-2-(difluoromethoxy)-1-(3-(difluoromethoxy)phenyl)ethyl)-3-hydroxy-3,5-dimethylhexanamide and (S)—N—((R)-2-(difluoromethoxy)-1-(3-(difluoromethoxy)phenyl)ethyl)-3-hydroxy-3,5-dimethylhexanamide

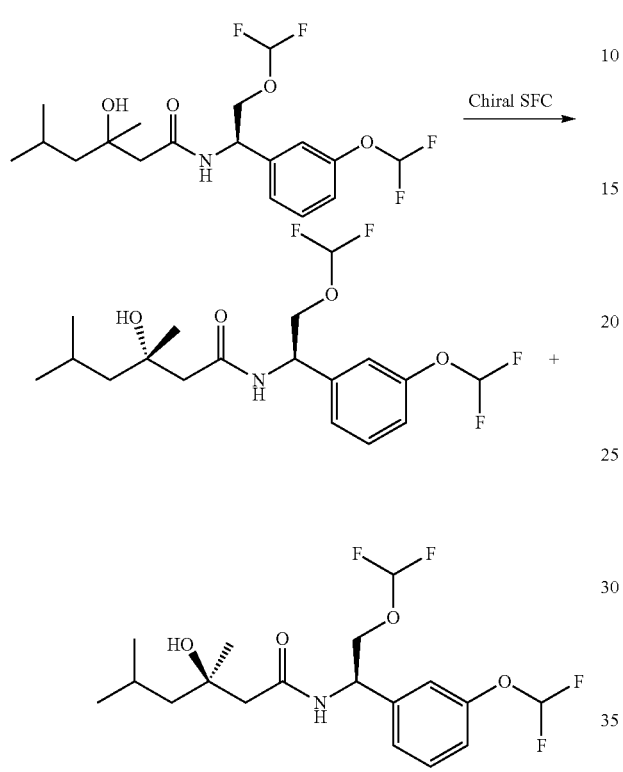

N—((R)-2-(difluoromethoxy)-1-(3-(difluoromethoxy)phenyl) ethyl)-3-hydroxy-3,5-dimethylhexanamide was separated by chiral SFC Example 13a $^1$H NMR (CDCl$_3$ 400 MHz): δ 7.37 (t, 1H), 7.19 (d, 1H), 7.10-7.07 (m, 2H), 6.76 (d, 1H), 6.51 (t, 1H), 6.23 (t, 1H), 5.35-5.30 (m, 1H), 4.19-4.08 (m, 2H), 3.39 (s, 1H), 2.51-2.34 (m, 2H), 1.84-1.76 (m, 1H), 1.43 (d, 2H), 1.27 (s, 3H), 0.98-0.95 (m, 6H).

LC-MS: tR=2.54 min (LCMS Method 1), m/z=396.1 [M+H]$^+$.

SFC: tR=2.40 min (SFC Method 15), ee %=99.3%.

Example 13b $^1$H NMR (CDCl$_3$ 400 MHz): δ 7.37 (t, 1H), 7.19 (d, 1H), 7.10 (s, 1H), 7.07 (d, 1H), 6.73 (d, 1H), 6.51 (t, 1H), 6.23 (t, 1H), 5.35-5.31 (m, 1H), 4.19-4.09 (m, 2H), 3.37 (s, 1H), 2.50-2.34 (m, 2H), 1.85-1.76 (m, 1H), 1.45 (d, 2H), 1.26 (s, 3H), 1.00-0.94 (m, 6H).

LC-MS: t$_R$=2.54 min (LC-MS Method 1), m/z=396.1 [M+H]$^+$.

SFC: t$_R$=2.66 min (SFC Method 15), ee %=98.8%.

Example 14a: N—((R)-2-(difluoromethoxy)-1-(3-(difluoromethoxy)phenyl)ethyl)-3-hydroxy-3,4-dimethylpentanamide

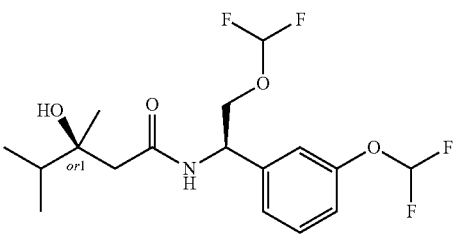 [SMILES: CC(C)[C@@](C)(O)CC(=O)N[C@@H](COC(F)F)c1cccc(OC(F)F)c1]

And

Example 14b: N—((R)-2-(difluoromethoxy)-1-(3-(difluoromethoxy)phenyl)ethyl)-3-hydroxy-3,4-dimethylpentanamide

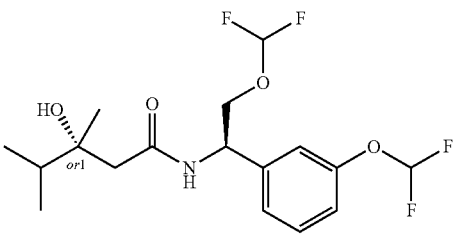 [SMILES: CC(C)[C@](C)(O)CC(=O)N[C@@H](COC(F)F)c1cccc(OC(F)F)c1]

Step 1: Preparation of N—((R)-2-(difluoromethoxy)-1-(3-(difluoromethoxy)phenyl)ethyl)-3-hydroxy-3,4-dimethylpentanamide

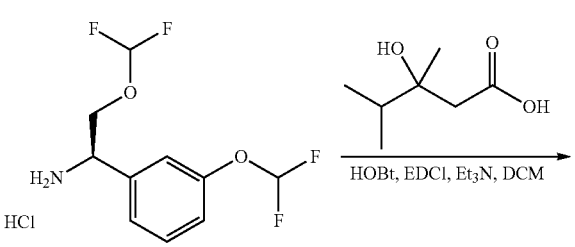

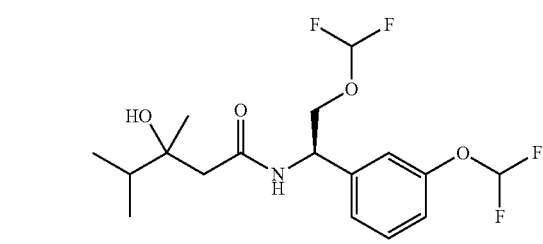

Prepared from IIa and IIIf

Step 2: Separation of (S)—N—((R)-2-(difluoromethoxy)-1-(3-(difluoromethoxy)phenyl)ethyl)-3-hydroxy-3,4-dimethylpentanamide and (R)—N—((R)-2-(difluoromethoxy)-1-(3-(difluoromethoxy)phenyl)ethyl)-3-hydroxy-3,4-dimethylpentanamide Example 15a: N—((R)-2-(difluoromethoxy)-1-(3-(difluoromethoxy)phenyl)ethyl)-3-(3,3-dimethylcyclobutyl)-3-hydroxypropanamide

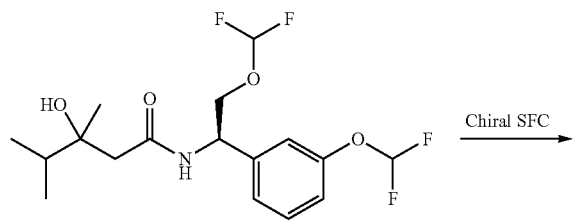

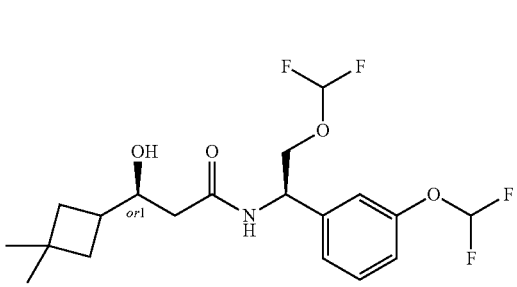 [SMILES: CC1(C)CC([C@@H](O)CC(=O)N[C@@H](COC(F)F)c2cccc(OC(F)F)c2)C1]

and

Example 15b: N—((R)-2-(difluoromethoxy)-1-(3-(difluoromethoxy)phenyl)ethyl)-3-(3,3-dimethylcyclobutyl)-3-hydroxypropanamide

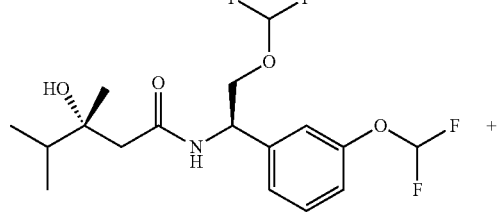

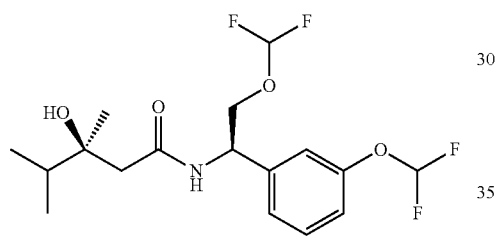

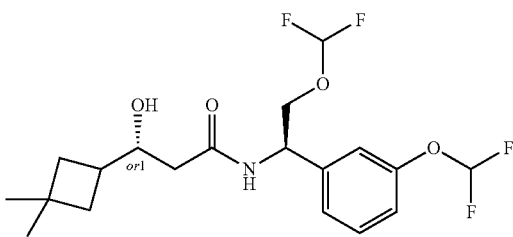 [SMILES: CC1(C)CC([C@H](O)CC(=O)N[C@@H](COC(F)F)c2cccc(OC(F)F)c2)C1]

N—((R)-2-(difluoromethoxy)-1-(3-(difluoromethoxy)phenyl)ethyl)-3-hydroxy-3,4-dimethylpentanamide was separated using chiral SFC.

Step 1: Preparation of N—((R)-2-(difluoromethoxy)-1-(3-(difluoromethoxy)phenyl)ethyl)-3-(3,3-dimethylcyclobutyl)-3-hydroxypropanamide Example 14a $^1$H NMR (CDCl$_3$ 400 MHz): δ 7.34 (t, 1H), 7.16 (d, 1H), 7.07 (s, 1H), 7.04 (d, 1H), 6.76 (d, 1H), 6.48 (t, 1H), 6.20 (t, 1H), 5.32-5.27 (m, 1H), 4.16-4.12 (m, 1H), 4.09-4.04 (m, 1H), 3.39 (s, 1H), 2.49-2.28 (m, 2H), 1.77-1.70 (m, 1H), 1.15 (s, 3H), 0.93-0.89 (m, 6H).

LC-MS: t$_R$=2.41 min (LCMS Method 1), m/z=382.0 [M+H]$^+$.

SFC: t$_R$=2.44 min (SFC Method 15), ee %=100%.

Example 14b $^1$H NMR (CDCl$_3$ 400 MHz): δ 7.35 (t, 1H), 7.16 (d, 1H), 7.08 (s, 1H), 7.04 (d, 1H), 6.79 (d, 1H), 6.48 (t, 1H), 6.19 (t, 1H), 5.31-5.26 (m, 1H), 4.14-4.10 (m, 1H), 4.08-4.04 (m, 1H), 3.43 (s, 1H), 2.48-2.28 (m, 2H), 1.75-1.69 (m, 1H), 1.12 (s, 3H), 0.92-0.88 (m, 6H).

LC-MS: t$_R$=2.41 min (LCMS Method 1), m/z=382.0 [M+H]$^+$.

SFC: t$_R$=2.68 min (SFC Method 15), ee %=97.4%.

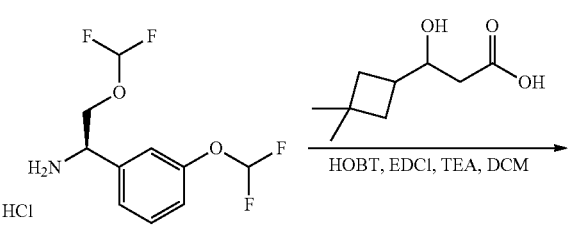

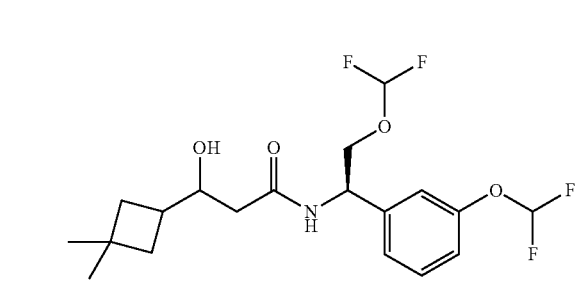

Prepared from IIa and IIIh

Step 2: Separation of (S)—N—((R)-2-(difluoromethoxy)-1-(3-(difluoromethoxy)phenyl)ethyl)-3-(3,3-dimethylcyclobutyl)-3-hydroxypropanamide and (R)—N—((R)-2-(difluoromethoxy)-1-(3-(difluoromethoxy)phenyl)ethyl)-3-(3,3-dimethylcyclobutyl)-3-hydroxypropanamide

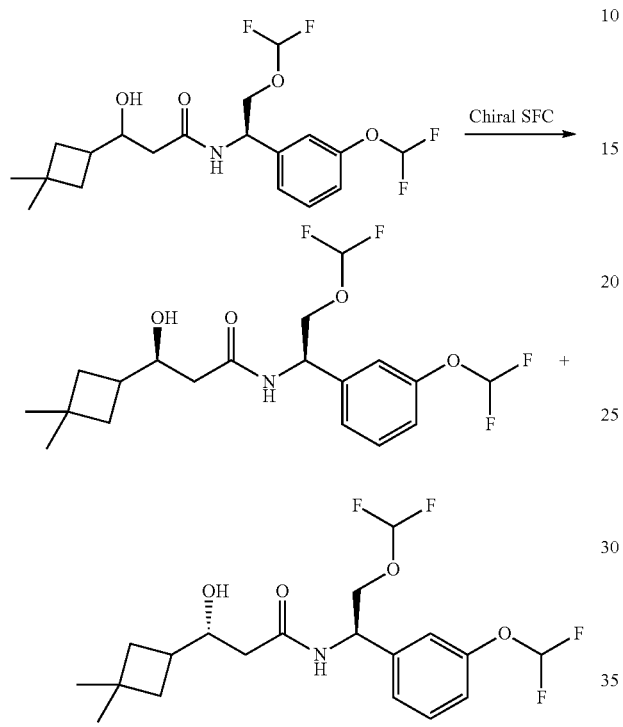

N—((R)-2-(difluoromethoxy)-1-(3-(difluoromethoxy)phenyl)ethyl)-3-(3,3-dimethylcyclobutyl)-3-hydroxypropanamide was separated by chiral SFC

Example 15a $^1$H NMR (DMSO-d6 400 MHz): δ 8.41 (d, 1H), 7.40 (t, 1H), 7.26 (d, 1H), 7.21 (t, 1H), 7.20 (s, 1H), 7.09 (d, 1H), 6.67 (t, 1H), 5.17-5.12 (m, 1H), 4.61 (d, 1H), 3.98-3.97 (m, 2H), 3.70-3.67 (m, 1H), 2.16-2.11 (m, 3H), 1.64-1.52 (m, 4H), 1.09 (s, 3H), 0.99 (s, 3H).

LC-MS: $t_R$=2.35 min (LC-MS Method 3), m/z=408.1[M+H]$^+$.

SFC: $t_R$=2.32 min (SFC Method 16), ee %=99.7

Example 15b $^1$H NMR (DMSO-d6 400 MHz): δ 8.43 (d, 1H), 7.40 (t, 1H), 7.24 (d, 1H), 7.22 (t, 1H), 7.18 (s, 1H), 7.08 (d, 1H), 6.67 (t, 1H), 5.14-5.10 (m, 1H), 4.63 (d, 1H), 3.99-3.96 (m, 2H), 3.70-3.67 (m, 1H), 2.13-2.08 (m, 3H), 1.64-1.49 (m, 4H), 1.06 (s, 3H), 0.97 (s, 3H).

LC-MS: tR=2.34 min (LCMS Method 3), m/z=408.1[M+H]$^+$.

SFC: $t_R$=2.64 min (SFC Method 16), ee %=98.7%.

Example 16a: 3-cyclopentyl-N—((R)-2-(difluoromethoxy)-1-(3-(difluoromethoxy)phenyl)ethyl)-3-hydroxypropanamide

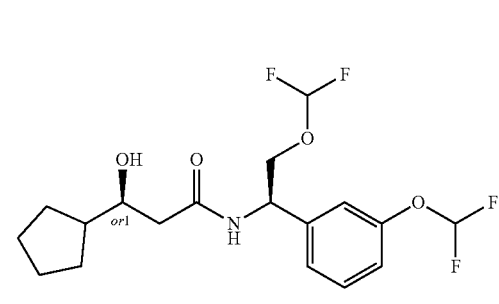 [SMILES: O=C(C[C@H](O)C1CCCC1)N[C@@H](COC(F)F)c1cccc(OC(F)F)c1]

and

Example 16b: 3-cyclopentyl-N—((R)-2-(difluoromethoxy)-1-(3-(difluoromethoxy)phenyl)ethyl)-3-hydroxypropanamide

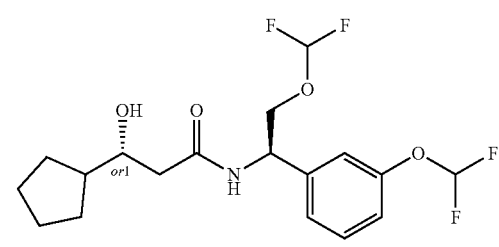

Step 1: Preparation of 3-cyclopentyl-N—((R)-2-(difluoromethoxy)-1-(3-(difluoromethoxy)phenyl)ethyl)-3-hydroxypropanamide

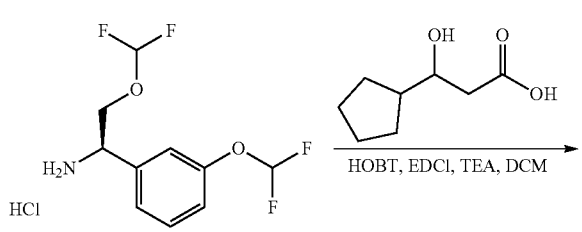

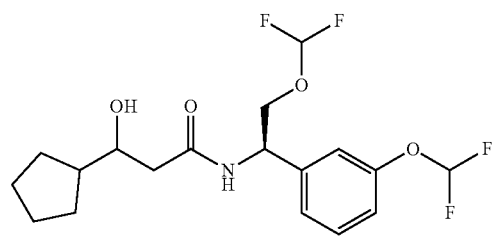 [SMILES: O=C(C[C@@H](O)C1CCCC1)N[C@@H](COC(F)F)c1cccc(OC(F)F)c1]

Prepared from IIa and IIIi

Step 2: Separation of (S)-3-cyclopentyl-N—((R)-2-(difluoromethoxy)-1-(3-(difluoromethoxy)phenyl)ethyl)-3-hydroxypropanamide and (R)-3-cyclopentyl-N—((R)-2-(difluoromethoxy)-1-(3-(difluoromethoxy)phenyl)ethyl)-3-hydroxypropanamide

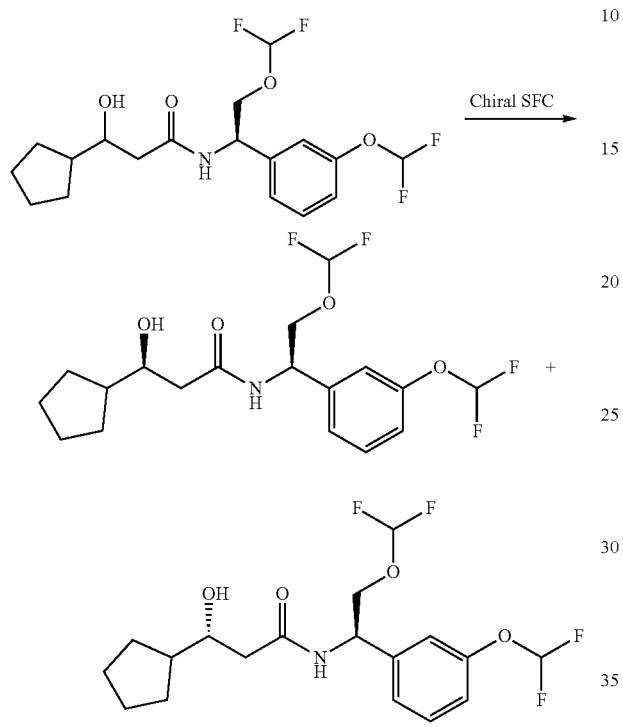

3-cyclopentyl-N—((R)-2-(difluoromethoxy)-1-(3-(difluoromethoxy)phenyl)ethyl)-3-hydroxypropanamide was separated by chiral SFC Example 16a $^{1}$H NMR (DMSO-d6 400 MHz) δ 8.43 (d, 1H), 7.39 (t, 1H), 7.27-7.25 (m, 1H), 7.20 (s, 1H), 7.20 (t, 1H), 7.08 (d, 1H), 6.66 (t, 1H), 5.16-5.14 (m, 1H), 4.61 (d, 1H), 3.99-3.97 (m, 2H), 3.69-3.65 (m, 1H), 2.26-2.25 (m, 2H), 1.80-1.76 (m, 1H), 1.64-1.22 (m, 8H).

LC-MS: $t_R$=2.48 min (LC-MS Method 1), m/z=394.1[M+H]$^{+}$.

SFC: $t_R$=2.64 min (SFC Method 17), ee %=98.8%.

Example 16b $^{1}$H NMR (DMSO-d6 400 MHz): δ 8.41 (d, 1H), 7.36 (d, 1H), 7.20 (d, 1H), 7.18 (t, 1H), 7.15 (s, 1H), 7.04 (m, 1H), 6.63 (t, 1H), 5.13-5.07 (m, 1H), 4.59 (d, 1H), 3.98-3.91 (m, 2H), 3.66-3.62 (m, 1H), 2.23-2.19 (m, 2H), 1.73-1.69 (m, 1H), 1.60-1.33 (m, 8H).

LC-MS: $t_R$=2.27 min (LC-MS Method 2), m/z=394.2[M+H]$^{+}$.

SFC: $t_R$=3.08 min (SFC Method 17), ee %=100%

Example 36a: 3-(1-fluorocyclopropyl)-3-hydroxy-N—((R)-2-methoxy-1-(3-(trifluoromethoxy)phenyl)ethyl) butanamide

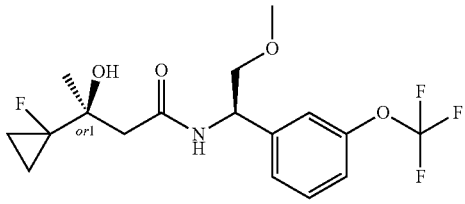 [SMILES: COC[C@H](NC(=O)C[C@](C)(O)C1(F)CC1)c1cccc(OC(F)(F)F)c1]

and

Example 36b: 3-(1-fluorocyclopropyl)-3-hydroxy-N—((R)-2-methoxy-1-(3-(trifluoromethoxy)phenyl)ethyl) butanamide

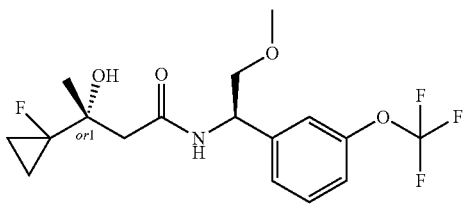 [SMILES: COC[C@H](NC(=O)C[C@@](C)(O)C1(F)CC1)c1cccc(OC(F)(F)F)c1]

Step 1: Preparation of 3-(1-fluorocyclopropyl)-3-hydroxy-N—((R)-2-methoxy-1-(3-(trifluoromethoxy)phenyl)ethyl)butanamide

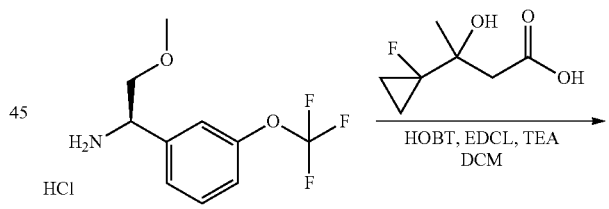

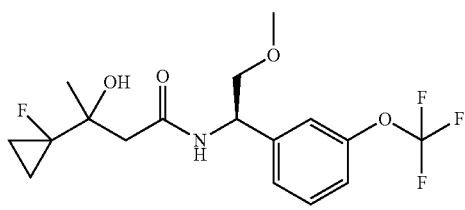

Prepared from IIp and IIIc

Step 2: Separation of (R)-3-(1-fluorocyclopropyl)-3-hydroxy-N—((R)-2-methoxy-1-(3-(trifluoromethoxy) phenyl) ethyl)butanamide and (S)-3-(1-fluorocyclopropyl)-3-hydroxy-N—((R)-2-methoxy-1-(3-(trifluoromethoxy) phenyl) ethyl)butanamide Example 17: (S)—N—((R)-2-cyclopropoxy-1-(3-(difluoromethoxy) phenyl)ethyl)-3-hydroxy-4,4-dimethylpentanamide

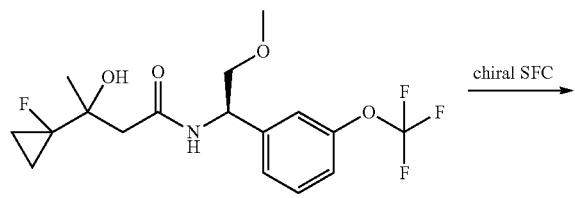

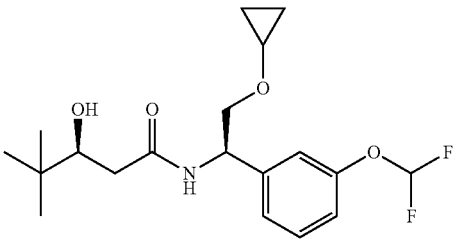 [SMILES: CC(C)(C)[C@@H](O)CC(=O)N[C@@H](COC1CC1)c1cccc(OC(F)F)c1]

Step 1: Preparation of (S)—N—((R)-2-cyclopropoxy-1-(3-(difluoromethoxy) phenyl)ethyl)-3-hydroxy-4,4-dimethylpentanamide

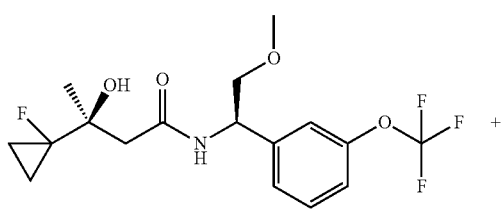

+

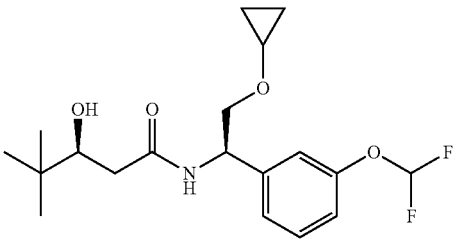 [SMILES: CC(C)(C)[C@@H](O)CC(=O)N[C@@H](COC1CC1)c1cccc(OC(F)F)c1]

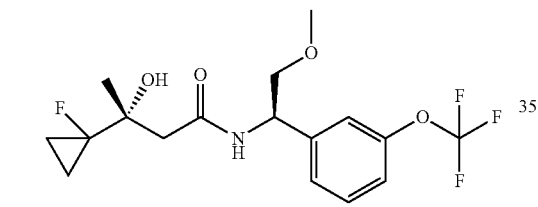

3-(1-fluorocyclopropyl)-3-hydroxy-N—((R)-2-methoxy-1-(3-(trifluoromethoxy)phenyl)ethyl)butanamide was separated using chiral SFC.

Example 36a $^1$H NMR (CDCl$_3$ 400 MHz): δ 7.38 (t, 1H), 7.29 (d, 1H), 7.22 (s, 1H), 7.16 (d, 1H), 6.58 (d, 1H), 5.18-5.13 (m, 1H), 5.04 (s, 1H), 3.70-3.62 (m, 2H), 3.38 (s, 3H), 2.72-2.68 (m, 1H), 2.54-2.50 (m, 1H), 1.36 (s, 3H), 0.81-0.53 (m, 4H).

LC-MS: $t_R$=2.43 min (LCMS Method 1), m/z=380.0 [M+H]$^+$.

SFC: tR=1.29 min (SFC Method 21), ee %=99.6%.

Example 36b $^1$H NMR (CDCl$_3$ 400 MHz): δ 7.38 (t, 1H), 7.28-7.27 (m, 1H), 7.20 (s, 1H), 7.15 (d, 1H), 6.58 (d, 1H), 5.18-5.14 (m, 1H), 4.93 (s, 1H), 3.70-3.62 (m, 2H), 3.38 (s, 3H), 2.71 (dd, 1H), 2.52 (dd, 1H), 1.35 (s, 3H), 1.00-0.86 (m, 4H).

LC-MS: $t_R$=2.53 min (LCMS Method 1), m/z=380.0 [M+H]$^+$.

SFC: $t_R$=1.76 min (SFC Method 22), ee %=81.4%.

To a solution of (R)-2-cyclopropoxy-1-(3-(difluoromethoxy)phenyl)ethan-1-amine hydrochloride (IIc) (0.2 g), (3S)-3-hydroxy-4,4-dimethyl-pentanoic acid (IIIa) (144 mg) and HATU (375 mg) in DCM (10 mL) was added DIEA (319 mg). The mixture was stirred at 20° C. for 16 hours and concentrated. The crude was purified to give (S)—N—((R)-2-cyclopropoxy-1-(3-(difluoromethoxy) phenyl)ethyl)-3-hydroxy-4,4-dimethylpentanamide.

$^1$H NMR (CDCl$_3$ 400 MHz): δ 7.33 (t, 1H), 7.17 (d, 1H), 7.08 (s, 1H), 7.03 (d, 1H), 6.49 (m, 1H), 6.51 (t, 1H), 5.18-5.14 (m, 1H), 3.80-3.78 (m, 1H), 3.72-3.66 (m, 2H), 3.42 (d, 1H), 3.35-3.25 (m, 1H), 2.44-2.26 (m, 2H), 0.93 (s, 9H), 0.57-0.45 (m, 4H).

LC-MS: $t_R$=2.40 min (LCMS Method 1), m/z=372.1 [M+H]$^+$.

SFC: $t_R$=1.988 min (SFC Method 7), ee %=97.5%.

The following examples were prepared by similar methodology as described for example 17, using the relevant intermediates:

Example 18: (S)—N—((R)-1-(3-(difluoromethoxy)phenyl)-2-(trifluoromethoxy)ethyl)-3-hydroxy-4,4-dimethylpentanamide

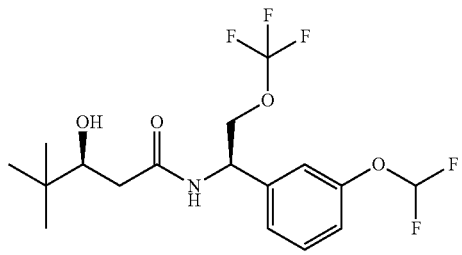 [SMILES: CC(C)(C)[C@@H](O)CC(=O)N[C@@H](COC(F)(F)F)c1cccc(OC(F)F)c1]

Prepared from IIe and IIIa
¹H NMR (CDCl₃ 400 MHz): δ 7.41-7.36 (m, 1H), 7.18 (d, 1H), 7.10-7.08 (m, 2H), 6.67 (d, 1H), 6.52 (t, 1H), 5.37-5.32 (m, 1H), 4.28-4.20 (m, 1H), 3.69 (d, 1H), 2.93 (s, 1H), 2.47-2.43 (m, 1H), 2.36-2.29 (m, 1H), 0.93 (s, 9H).
LC-MS: $t_R$=2.38 min (LCMS Method 3), m/z=400.0 [M+H]⁺.
SFC: $t_R$=2.11 min, (SFC Method 4), ee %=96.4%.

Example 19: (S)—N—((R)-1-(3-(trifluoromethoxy)phenyl)-2-(trifluoromethoxy)ethyl)-3-hydroxy-4,4-dimethylpentanamide

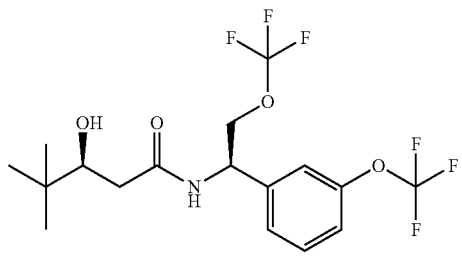 [SMILES: CC(C)(C)[C@@H](O)CC(=O)N[C@@H](COC(F)(F)F)c1cccc(OC(F)(F)F)c1]

¹H NMR (CDCl₃ 400 MHz): δ 7.35 (t, 1H), 7.21-7.19 (m, 1H), 7.13-7.11 (m, 2H), 6.65 (d, 1H), 5.32-5.27 (m, 1H), 4.21-4.13 (m, 1H), 3.64-3.61 (m, 1H), 2.83 (d, 1H), 2.41-2.36 (m, 1H), 2.29-2.25 (m, 1H), 0.86 (s, 9H).
LC-MS: $t_R$=2.56 min (LCMS Method 3), m/z=418.0 [M+H]⁺.
HPLC: $t_R$=13.54 min (HPLC Method 2), ee %=65.9%

Example 20: (S)—N—((S)-1-(3-(difluoromethoxy)phenyl)butyl)-3-hydroxy-4,4-dimethylpentanamide

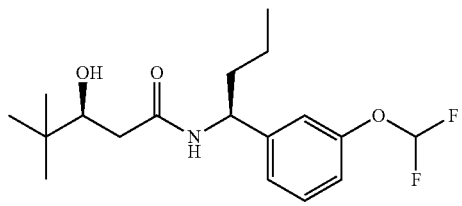 [SMILES: CCC[C@H](NC(=O)C[C@H](O)C(C)(C)C)c1cccc(OC(F)F)c1]

Prepared from IIg an IIa.
¹H NMR (CDCl₃ 400 MHz): δ 7.33 (t, 1H), 7.14 (d, 1H), 7.03-7.00 (m, 2H), 6.52 (t, 1H), 6.22-6.20 (m, 1H), 4.97 (q, 1H), 3.68-3.64 (m, 1H), 3.31 (d, 1H), 2.39-2.24 (m, 2H), 1.75-1.72 (m, 2H), 1.36-1.29 (m, 2H), 0.95-0.91 (m, 12H).
LC-MS: $t_R$=2.30 min (LCMS Method 3), m/z=344.1 [M+H]⁺.
SFC: $t_R$=2.13 min (SFC Method 1), ee %=98.7%.

Example 21: (S)—N—((S)-1-(3-(difluoromethoxy)phenyl)-4,4-difluorobutyl)-3-hydroxy-4,4-dimethylpentanamide

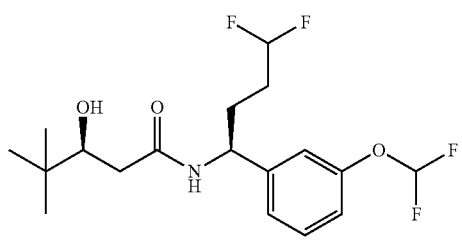

Prepared from IIh and IIIa.
¹H NMR (CDCl₃ 400 MHz): δ 7.36 (t, 1H), 7.14 (d, 1H), 7.05 (m, 2H), 6.52 (t, 1H), 6.25 (d, 1H), 5.84 (tt, 1H), 5.03 (q, 1H), 3.68 (m, 1H), 2.97 (d, 1H), 2.40-2.21 (2H), 1.98-1.77 (4H), 0.91 (s, 9H).
LC-MS: $t_R$=2.43 min (LCMS Method 1), m/z=380.0 [M+H]⁺.
HPLC: $t_R$=14.01 min (HPLC Method 3), ee %=95.7%.

Example 22: (S)—N—((S)-1-(3-(difluoromethoxy)phenyl)-3,3-difluoropropyl)-3-hydroxy-4,4-dimethylpentanamide

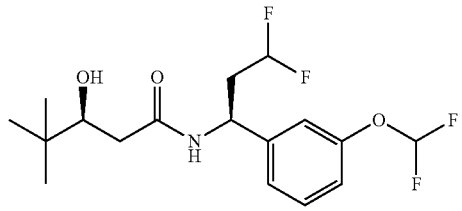 [SMILES: CC(C)(C)[C@@H](O)CC(=O)N[C@@H](CC(F)F)c1cccc(OC(F)F)c1]

Prepared from IIi and IIIa.
¹H NMR (CDCl₃ 400 MHz): δ 7.35 (t, 1H), 7.14 (d, 1H), 7.05-7.03 (m, 2H), 6.50 (t, 1H), 6.53-6.50 (m, 1H), 5.80 (tt, 1H), 5.30-5.24 (m, 1H), 3.66 (dd, 1H), 2.89 (s, 1H), 2.40-2.22 (m, 4H), 0.89 (s, 9H).
LC-MS: $t_R$=2.63 min (LCMS Method 1), m/z=366.2 [M+H]⁺.
HPLC: $t_R$=13.43 min (HPLC Method 1), ee %=96.7%.

Example 23: (S)—N—((S)-1-(3-(difluoromethoxy)phenyl)ethyl)-3-hydroxy-4,4-dimethylpentanamide

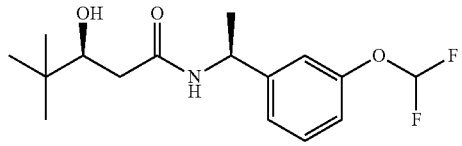 [SMILES: C[C@H](NC(=O)C[C@H](O)C(C)(C)C)c1cccc(OC(F)F)c1]

Prepared from IIj and IIIa.

¹H NMR (CDCl₃ 400 MHz): δ 7.34-7.30 (m, 1H), 7.16-7.12 (m, 1H), 7.04-6.97 (m, 2H), 6.31 (t, 1H), 6.14 (brs, 1H), 5.12-5.06 (m, 1H), 3.67-3.62 (m, 1H), 3.29 (s, 1H), 2.37-2.31 (m, 1H), 2.26-2.19 (m, 1H), 1.47-1.43 (m, 3H), 0.98 (s, 9H).

LC-MS: $t_R$=2.155 min (LCMS Method 2), m/z=316.1 [M+H]⁺.

SFC: $t_R$=2.416 min (SFC Method 8), ee %=100%.

Example 24: (S)—N—((S)-2-cyano-1-(3-(trifluoromethoxy)phenyl)ethyl)-3-hydroxy-4,4-dimethylpentanamide

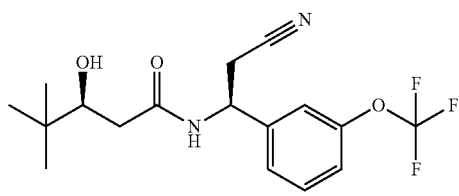 [SMILES: CC(C)(C)[C@@H](O)CC(=O)N[C@@H](CC#N)c1cccc(OC(F)(F)F)c1]

Prepared from IIm and IIIa.

¹H NMR (400 MHz, DMSO-d6): δ 8.66 (d, 1H), 7.51 (t, 1H), 7.45-7.43 (m, 2H), 7.30 (d, 1H), 5.25-5.23 (m, 1H), 4.62 (d, 1H), 3.57-3.51 (m, 1H), 3.00 (dd, 2H), 2.31-2.11 (m, 2H), 0.81 (s, 9H).

LC-MS: $t_R$=2.42 min (LSMS Method 1), m/z=359.2 [M+H]⁺.

HPLC: $t_R$=12.56 min (HPLC Method 4), ee %=100%.

Example 25: (S)—N—((S)-3-cyano-1-(3-(trifluoromethoxy)phenyl) propyl)-3-hydroxy-4,4-dimethylpentanamide

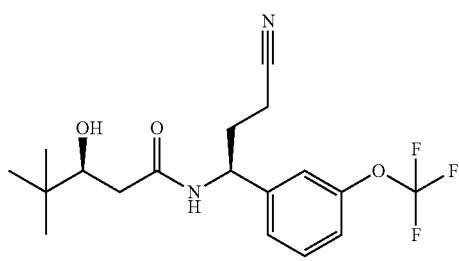 [SMILES: CC(C)(C)[C@@H](O)CC(=O)N[C@@H](CCC#N)c1cccc(OC(F)(F)F)c1]

Prepared from IIn and IIIa.

¹H NMR (CDCl₃ 400 MHz): δ 7.42 (t, 1H), 7.24 (m, 1H), 7.18 (d, 1H), 7.13 (s, 1H), 6.49 (d, 1H), 5.19-5.13 (m, 1H), 3.75-3.71 (m, 1H), 2.82 (d, 1H), 2.45-2.40 (m, 3H), 2.30-2.27 (m, 1H), 2.23-2.16 (m, 2H), 0.92 (s, 9H).

LC-MS: $t_R$=2.44 min (LCMS Method 1), m/z=373.2 [M+H]⁺.

SFC: $t_R$=1.47 min (SFC Method 9), ee %=95.8%.

Example 26: (R)-2-(3,3-difluoro-1-hydroxycyclobutyl)-N-(2-(difluoromethoxy)-1-(3-(difluoromethoxy)phenyl) ethyl)acetamide

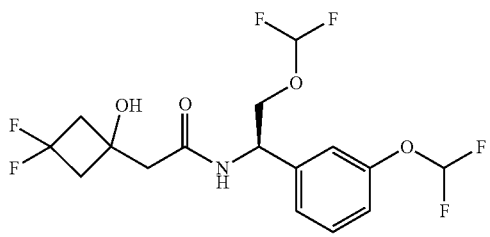 [SMILES: O=C(CC1(O)CC(F)(F)C1)N[C@@H](COC(F)F)c1cccc(OC(F)F)c1]

Prepared from IIa and IIIb.

¹H NMR (CDCl₃ 400 MHz): δ 7.37 (t, 1H), 7.15 (d, 1H), 7.09-7.06 (m, 2H), 6.50 (t, 1H), 6.32 (t, 1H), 6.23 (m, 1H), 5.29-5.24 (m, 1H), 4.74 (s, 1H), 4.17 (dd, 1H), 4.08 (dd, 1H), 2.75-2.72 (m, 2H), 2.68 (s, 2H), 2.62-2.56 (m, 2H).

LC-MS: $t_R$=2.39 min (LCMS Method 1), m/z=402.1 [M+H]⁺.

SFC: $t_R$=1.87 min (SFC Method 1), ee %=100%

Example 27: (R)-2-(3,3-difluoro-1-hydroxycyclobutyl)-N-(2-(difluoromethoxy)-1-(3-(trifluoromethoxy)phenyl)ethyl)acetamide

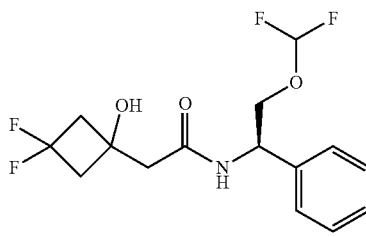

Prepared from IIb and IIIb.

¹H NMR (CDCl₃ 400 MHz): δ 7.35 (t, 1H), 7.14-7.09 (m, 3H), 6.18 (t, 1H), 6.21 (d, 1H), 5.23 (m, 1H), 4.66 (br s, 1H), 4.13 (dd, 1H), 4.04 (dd, 1H), 2.72-2.66 (m, 2H), 2.64 (s, 2H), 2.56-2.50 (m, 2H).

LC-MS: $t_R$=2.53 min (LC-MS Method 1), m/z=420.2 [M+H]⁺.

HPLC: $t_R$=12.77 min (HPLC Method 2), ee %=86.7%.

Example 28: (R)—N-(2-cyclopropoxy-1-(3-(trifluoromethoxy)phenyl)ethyl)-2-(3,3-difluoro-1-hydroxycyclobutyl)acetamide

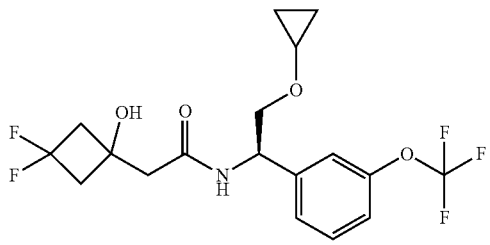 [SMILES: O=C(CC1(O)CC(F)(F)C1)N[C@@H](COC1CC1)c1cccc(OC(F)(F)F)c1]

Prepared from IId and IIIb.

¹H NMR (CDCl₃ 400 MHz): δ 7.37 (t, 1H), 7.22 (d, 1H), 7.15 (m, 2H), 6.40 (d, 1H), 5.13 (m, 1H), 4.92 (s, 1H), 3.81 (m, 1H), 3.69 (m, 1H), 3.29 (m, 1H), 2.78-2.52 (6H), 0.57-0.44 (4H).

LC-MS: $t_R$=2.53 min (LC-MS Method 1), m/z=410.0 [M+H]⁺.

SFC: $t_R$=1.50 min (SFC Method 7), ee %=99.7%

Example 29: (R)—N-(2-cyclopropoxy-1-(3-(difluoromethoxy)phenyl)ethyl)-2-(3,3-difluoro-1-hydroxycyclobutyl)acetamide

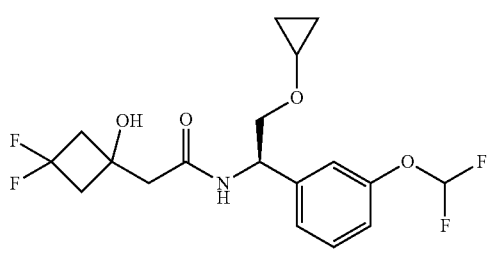 [SMILES: O=C(CC1(O)CC(F)(F)C1)N[C@@H](COC1CC1)c1cccc(OC(F)F)c1]

Prepared from IIe and IIIb.

¹H NMR (CDCl₃ 400 MHz): δ 7.35 (d, 1H), 7.15 (d, 1H), 7.06 (s, 1H), 7.05 (d, 1H), 6.51 (t, 1H), 6.39 (d, 1H), 5.15-5.10 (m, 1H), 4.98 (m, 1H), 3.83-3.67 (m, 2H), 3.31-3.30 (m, 1H), 2.79-2.75 (m, 2H), 2.68 (d, 2H), 2.64-2.52 (m, 2H), 0.60-0.46 (m, 4H).

LC-MS: $t_R$=2.40 min (LC-MS Method 1), m/z=392.1[M+H]⁺.

SFC: $t_R$=2.32 min (SFC Method 6), ee %=100.00%

Example 30: (R)-2-(3,3-difluoro-1-hydroxycyclobutyl)-N-(1-(3-(difluoromethoxy)phenyl)-2-(trifluoromethoxy)ethyl)acetamide

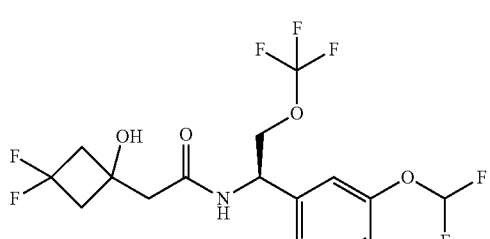

Prepared form IIe and IIIb.

¹H NMR (CDCl₃ 400 MHz): δ 7.39 (t, 1H), 7.15 (d, 1H), 7.08 (m, 2H), 6.51 (t, 1H), 6.30 (m, 1H), 5.32 (m, 1H), 4.63 (s, 1H), 4.23 (m, 2H), 2.76-2.57 (6H).

LC-MS: $t_R$=2.48 min (LC-MS Method 1), m/z=420.0 [M+H]⁺.

SFC: $t_R$=12.96 min (HPLC Method 2), ee %=75.5%

Example 31: (S)-2-(3,3-difluoro-1-hydroxycyclobutyl)-N-(1-(3-(difluoromethoxy)phenyl)butyl)acetamide

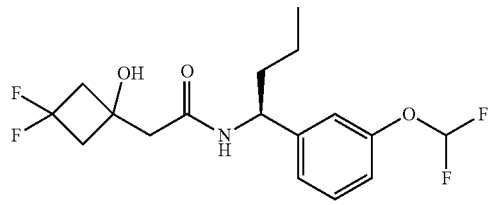 [SMILES: CCC[C@H](NC(=O)CC1(O)CC(F)(F)C1)c1cccc(OC(F)F)c1]

Prepared form IIg and IIIb.

¹H NMR (CDCl₃ 400 MHz): δ 7.35 (t, 1H), 7.13 (d, 1H), 7.04 (m, 2H), 6.52 (t, 1H), 5.91 (m, 1H), 5.04 (s, 1H), 4.96 (q, 1H), 2.78-2.56 (6H), 1.76 (m, 2H), 1.34 (m, 2H), 0.95 (t, 3H).

LC-MS: $t_R$=2.44 min (LC-MS Method 1), m/z=364.0 [M+H]⁺.

SFC: $t_R$=1.71 min (SFC Method 10), ee %=94.8%.

Example 32: (S)-2-(3,3-difluoro-1-hydroxycyclobutyl)-N-(1-(3-(difluoromethoxy)phenyl)-4,4-difluorobutyl)acetamide

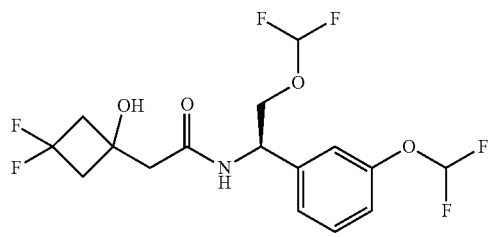 [SMILES: O=C(CC1(O)CC(F)(F)C1)N[C@@H](COC(F)F)c1cccc(OC(F)F)c1]

Prepared from IIh and IIIb.

¹H NMR (CDCl₃ 400 MHz): δ 7.38 (t, 1H), 7.13 (d, 1H), 7.08 (d, 1H), 7.04 (s, 1H), 6.52 (t, 1H), 5.90 (d, 1H), 5.85 (tt, 1H), 5.00 (q, 1H), 4.82 (s, 1H), 2.78-2.54 (6H), 2.00 (m, 2H), 1.86 (m, 2H).

LC-MS: $t_R$=2.50 min (LCMS Method 1), m/z=400.1 [M+H]⁺.

HPLC: $t_R$=12.48 min (HPLC Method 2), ee %=98.3%.

Example 33: (S)-2-(3,3-difluoro-1-hydroxycyclobutyl)-N-(1-(3-(trifluoromethoxy)-phenyl)propy)acetamide

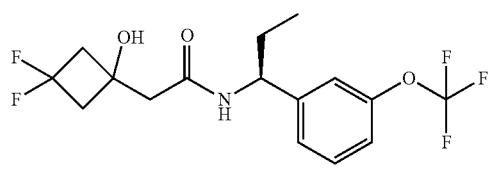 [SMILES: CC[C@H](NC(=O)CC1(O)CC(F)(F)C1)c1cccc(OC(F)(F)F)c1]

Prepared from Il and IIIb.

¹H NMR (CDCl₃ 400 MHz): δ 7.38 (t, 1H), 7.20 (d, 1H), 7.14 (d, 1H), 7.10 (s, 1H), 5.89 (d, 1H), 4.99 (brs, 1H), 4.89 (q, 1H), 2.77-2.70 (m, 2H), 2.63 (d, 2H), 2.60-2.50 (m, 2H), 1.87-1.80 (m, 2H), 0.92 (t, 3H).

LC-MS: $t_R$=2.57 min (LCMS Method 1), m/z=368.1 [M+H]+.

SFC: $t_R$=13.09 min (SFC Method 1), ee %=100%

Example 34: (S)—N-(2-cyano-1-(3-(trifluoromethoxy) phenyl)ethyl)-2-(3,3-difluoro-1-hydroxycyclobutyl)acetamide

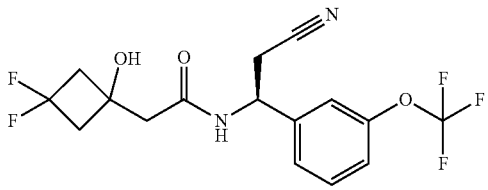 [SMILES: N#CC[C@H](NC(=O)CC1(O)CC(F)(F)C1)c1cccc(OC(F)(F)F)c1]

Prepared from IIm and IIIb.

$^1$H NMR (CDCl$_3$ 400 MHz): δ 7.46 (t, 1H), 7.30 (d, 1H), 7.24 (m, 1H), 7.19 (s, 1H), 6.51 (s, 1H), 5.34-5.29 (m, 1H), 4.44 (s, 1H), 3.09-3.03 (m, 1H), 2.91-2.89 (m, 1H), 2.77-2.73 (m, 2H), 2.70-2.53 (m, 4H).

LC-MS: $t_R$=2.257 min (LC-MS Method 1), m/z=379.0 [M+H]+.

SFC: $t_R$=2.60 min (SFC Method 11), ee %=100%.

Example 35: (S)—N-(3,3-difluoro-1-(3-(trifluoromethoxy)phenyl)propyl)-2-(3,3-difluoro-1-hydroxycyclobutyl)acetamide

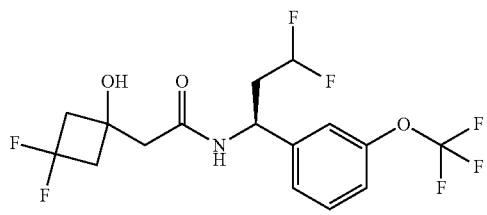 [SMILES: O=C(CC1(O)CC(F)(F)C1)N[C@@H](CC(F)F)c1cccc(OC(F)(F)F)c1]

Prepared from IIo and IIIb $^1$H NMR (CDCl$_3$ 400 MHz): δ 7.44 (t, 1H), 7.23 (m, 2H), 7.15 (s, 1H), 6.15 (br d, 1H), 5.83 (tt, 1H), 5.32 (m, 1H), 4.69 (s, 1H), 2.73 (m, 2H), 2.66 (s, 2H), 2.62-2.34 (4H).

LC-MS: $t_R$=2.53 min (LC-MS Method 1), m/z=404.1 [M+H]+.

SFC: $t_R$=1.66 min (SFC Method 19), ee %=98.5%

The invention claimed is:

1. A compound of Formula I

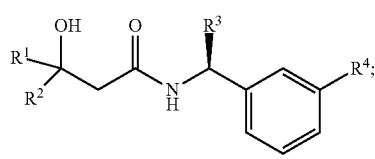

Formula I wherein

R1 is selected from the group consisting of $C_1$-$C_6$ alkyl, $CF_3$, $CH_2CF_3$, $CF_2CHF_2$, and $C_3$-$C_8$ cycloalkyl, wherein said $C_3$-$C_8$ cycloalkyl may be substituted with 1 or 2 substituents selected from the group consisting of $C_1$-$C_3$ alkyl, F, $CHF_2$ and $CF_3$; and R2 is H, $C_1$-$C_6$ alkyl or $CF_3$; or R1 and R2 combine to form $C_3$-$C_5$ cycloalkyl optionally substituted with 1 or 2 F, $CHF_2$ or $CF_3$; and R3 is $C_1$-$C_3$ alkyl, $CH_2O$—$C_{1-3}$ alkyl, or $CH_2O$-cyclopropyl, wherein said $C_1$-$C_3$ alkyl or $CH_2O$—$C_1$-$C_3$ alkyl is substituted with C≡N or $C_3$-$C_5$ cycloalkyl; and R4 is selected from the group consisting of $OCF_3$, or $OCHF_2$;

or a pharmaceutically acceptable salt thereof.

2. The compound according to claim 1, or a pharmaceutically acceptable salt thereof, wherein R4 is $OCF_3$.

3. The compound according to claim 1, or a pharmaceutically acceptable salt thereof, wherein R3 is selected from the group consisting of $CH_2$—O— cyclopropyl and $CH_2$—C≡N.

4. The compound according to claim 1 or a pharmaceutically acceptable salt thereof, wherein R1 is $C_3$-$C_4$ cycloalkyl optionally substituted with 1 or 2 $C_1$-$C_3$ alkyl, F, $CHF_2$ or $CF_3$.

5. The compound according to claim 1, or a pharmaceutically acceptable salt thereof, wherein R1 and R2 combine to form cyclobutyl optionally substituted with 1 or 2 F and R4 is $OCF_3$ or $OCHF_2$.

6. The compound of claim 1, wherein the compound is selected from the group consisting of:

(S)—N—((R)-2-cyclopropoxy-1-(3-(difluoromethoxy) phenyl)ethyl)-3-hydroxy-4,4-dimethylpentanamide;

(S)—N—((S)-2-cyano-1-(3-(trifluoromethoxy)phenyl) ethyl)-3-hydroxy-4,4-dimethylpentanamide;

(S)—N—((S)-3-cyano-1-(3-(trifluoromethoxy)phenyl) propyl)-3-hydroxy-4,4-dimethylpentanamide;

(R)—N-(2-cyclopropoxy-1-(3-(trifluoromethoxy)phenyl) ethyl)-2-(3,3-difluoro-1-hydroxycyclobutyl)acetamide;

(R)—N-(2-cyclopropoxy-1-(3-(difluoromethoxy)phenyl) ethyl)-2-(3,3-difluoro-1-hydroxycyclobutyl)acetamide; and (S)—N-(2-cyano-1-(3-(trifluoromethoxy)phenyl)ethyl)-2-(3,3-difluoro-1-hydroxycyclobutyl)acetamide, or a pharmaceutically acceptable salt thereof.

7. A pharmaceutical composition comprising a compound of claim 1, or a pharmaceutically acceptable salt thereof, and one or more pharmaceutically acceptable excipients.

8. A method for the manufacture of a pharmaceutical composition comprising combining a compound according to claim 1, or a pharmaceutically acceptable salt thereof, with a pharmaceutically acceptable excipient.

9. The compound according to claim 1, or a pharmaceutically acceptable salt thereof, wherein R4 is $OCHF_2$.

* * * * *